US011497600B2

(12) United States Patent
Ganesan et al.

(10) Patent No.: US 11,497,600 B2
(45) Date of Patent: *Nov. 15, 2022

(54) SYSTEMS AND METHODS FOR HEART VALVE THERAPY

(71) Applicant: Caisson Interventional LLC, Maple Grove, MN (US)

(72) Inventors: Kavitha Ganesan, Maple Grove, MN (US); Ramji T. Venkatasubramanian, Maple Grove, MN (US); Cyril J. Schweich, Jr., Maple Grove, MN (US); Todd J. Mortier, Mound, MN (US)

(73) Assignee: CAISSON INTERVENTIONAL, LLC, Maple Grove, MN (US)

( * ) Notice: Subject to any disclaimer, the term of this patent is extended or adjusted under 35 U.S.C. 154(b) by 366 days.

This patent is subject to a terminal disclaimer.

(21) Appl. No.: 16/590,215

(22) Filed: Oct. 1, 2019

(65) Prior Publication Data

US 2020/0038177 A1    Feb. 6, 2020

Related U.S. Application Data

(63) Continuation of application No. 15/072,588, filed on Mar. 17, 2016, now Pat. No. 10,449,039.

(60) Provisional application No. 62/135,276, filed on Mar. 19, 2015.

(51) Int. Cl.
*A61F 2/24*    (2006.01)

(52) U.S. Cl.
CPC .......... *A61F 2/2409* (2013.01); *A61F 2/2418* (2013.01); *A61F 2/2436* (2013.01); *A61F 2/2439* (2013.01); *A61F 2250/006* (2013.01)

(58) Field of Classification Search
CPC .... A61F 2/2409; A61F 2/2418; A61F 2/2436; A61F 2/2439; A61F 2250/006
See application file for complete search history.

(56) References Cited

U.S. PATENT DOCUMENTS

| 4,680,031 A | 7/1987 | Alonso |
| 5,423,887 A | 6/1995 | Love et al. |
| 5,662,704 A | 9/1997 | Gross |
| 5,855,601 A | 1/1999 | Bessler et al. |
| 5,984,959 A | 11/1999 | Robertson et al. |

(Continued)

FOREIGN PATENT DOCUMENTS

| EP | 3270827 A1 | 1/2018 |
| JP | 2014-230797 A | 12/2014 |

(Continued)

OTHER PUBLICATIONS

European Search Report and Search Opinion Received for EP Application No. 16765717.0, dated Oct. 31, 2018, 7 pages.

(Continued)

*Primary Examiner* — George J Ulsh

(57) ABSTRACT

Prosthetic mitral valves described herein can be deployed using a transcatheter mitral valve delivery system and technique to interface and anchor in cooperation with the anatomical structures of a native mitral valve. This document describes prosthetic heart valve designs and techniques to manage blood flow through the left ventricular outflow tract. For example, this document describes prosthetic heart valve designs and techniques that reduce or prevent obstructions of the left ventricular outflow tract that may otherwise result from systolic anterior motion of an anterior leaflet of the native mitral valve.

16 Claims, 29 Drawing Sheets

(56) References Cited

U.S. PATENT DOCUMENTS

| | | |
|---|---|---|
| 6,113,631 A | 9/2000 | Jansen |
| 6,296,662 B1 | 10/2001 | Caffey |
| 6,309,417 B1 | 10/2001 | Spence et al. |
| 6,332,893 B1 | 12/2001 | Mortier et al. |
| 6,358,277 B1 | 3/2002 | Duran |
| 6,425,916 B1 | 7/2002 | Garrison et al. |
| 6,530,952 B2 | 3/2003 | Vesely |
| 6,569,196 B1 | 5/2003 | Vesely |
| 6,582,462 B1 | 6/2003 | Andersen et al. |
| 6,629,534 B1 | 10/2003 | St et al. |
| 6,730,121 B2 | 5/2004 | Ortiz et al. |
| 6,767,362 B2 | 7/2004 | Schreck |
| 6,769,434 B2 | 8/2004 | Liddicoat et al. |
| 6,790,229 B1 | 9/2004 | Berreklouw |
| 6,883,522 B2 | 4/2005 | Spence et al. |
| 6,893,459 B1 | 5/2005 | Macoviak |
| 6,908,481 B2 | 6/2005 | Cribier |
| 6,949,122 B2 | 9/2005 | Adams et al. |
| 7,011,681 B2 | 3/2006 | Vesely |
| 7,018,406 B2 | 3/2006 | Seguin et al. |
| 7,044,966 B2 | 5/2006 | Svanidze et al. |
| 7,101,396 B2 | 9/2006 | Artof et al. |
| 7,147,663 B1 | 12/2006 | Berg et al. |
| 7,160,322 B2 | 1/2007 | Gabbay |
| 7,217,287 B2 | 5/2007 | Wilson et al. |
| 7,252,682 B2 | 8/2007 | Seguin |
| 7,320,704 B2 | 1/2008 | Lashinski et al. |
| 7,329,278 B2 | 2/2008 | Seguin et al. |
| 7,381,218 B2 | 6/2008 | Schreck |
| 7,381,220 B2 | 6/2008 | Macoviak et al. |
| 7,442,204 B2 | 10/2008 | Schwammenthal et al. |
| 7,503,930 B2 | 3/2009 | Sharkawy et al. |
| 7,524,330 B2 | 4/2009 | Berreklouw |
| 7,524,331 B2 | 4/2009 | Birdsall |
| 7,578,843 B2 | 8/2009 | Shu |
| 7,585,321 B2 | 9/2009 | Cribier |
| 7,597,711 B2 | 10/2009 | Drews et al. |
| 7,618,446 B2 | 11/2009 | Andersen et al. |
| 7,625,403 B2 | 12/2009 | Krivoruchko |
| 7,632,308 B2 | 12/2009 | Loulmet |
| 7,708,775 B2 | 5/2010 | Rowe et al. |
| 7,717,955 B2 | 5/2010 | Lane et al. |
| 7,727,276 B2 | 6/2010 | Machiraju |
| 7,748,389 B2 | 7/2010 | Salahieh et al. |
| 7,776,083 B2 | 8/2010 | Vesely |
| 7,780,725 B2 | 8/2010 | Haug et al. |
| 7,785,364 B2 | 8/2010 | Styrc |
| 7,896,915 B2 | 3/2011 | Guyenot et al. |
| 7,914,569 B2 | 3/2011 | Nguyen et al. |
| 7,935,144 B2 | 5/2011 | Robin et al. |
| 7,947,072 B2 | 5/2011 | Yang et al. |
| 7,947,075 B2 | 5/2011 | Goetz et al. |
| 7,959,672 B2 | 6/2011 | Salahieh et al. |
| 7,981,153 B2 | 7/2011 | Fogarty et al. |
| 7,988,725 B2 | 8/2011 | Gross et al. |
| 8,016,882 B2 | 9/2011 | Macoviak et al. |
| 8,025,695 B2 | 9/2011 | Fogarty et al. |
| 8,048,153 B2 | 11/2011 | Salahieh et al. |
| 8,052,749 B2 | 11/2011 | Salahieh et al. |
| 8,055,360 B2 | 11/2011 | Park et al. |
| 8,057,540 B2 | 11/2011 | Letac et al. |
| 8,062,355 B2 | 11/2011 | Figulla et al. |
| 8,092,518 B2 | 1/2012 | Schreck |
| 8,092,521 B2 | 1/2012 | Figulla et al. |
| 8,092,524 B2 | 1/2012 | Nugent et al. |
| 8,123,801 B2 | 2/2012 | Milo |
| 8,133,270 B2 | 3/2012 | Kheradvar et al. |
| 8,142,492 B2 | 3/2012 | Forster et al. |
| 8,157,852 B2 | 4/2012 | Bloom et al. |
| 8,157,853 B2 | 4/2012 | Laske et al. |
| 8,163,011 B2 | 4/2012 | Rankin |
| 8,172,898 B2 | 5/2012 | Alferness et al. |
| 8,182,528 B2 | 5/2012 | Salahieh et al. |
| 8,182,530 B2 | 5/2012 | Huber |
| 8,206,437 B2 | 6/2012 | Bonhoeffer et al. |
| 8,231,670 B2 | 7/2012 | Salahieh et al. |
| 8,236,049 B2 | 8/2012 | Rowe et al. |
| 8,246,677 B2 | 8/2012 | Ryan |
| 8,252,051 B2 | 8/2012 | Chau et al. |
| 8,262,724 B2 | 9/2012 | Seguin et al. |
| 8,273,120 B2 | 9/2012 | Dolan |
| 8,277,502 B2 | 10/2012 | Miller et al. |
| 8,282,051 B2 | 10/2012 | Nutaro et al. |
| 8,287,591 B2 | 10/2012 | Keidar et al. |
| 8,292,938 B2 | 10/2012 | Case |
| 8,308,796 B2 | 11/2012 | Lashinski et al. |
| 8,308,798 B2 | 11/2012 | Pintor et al. |
| 8,317,858 B2 | 11/2012 | Straubinger et al. |
| 8,323,332 B2 | 12/2012 | Agnew |
| 8,323,335 B2 | 12/2012 | Rowe et al. |
| 8,348,998 B2 | 1/2013 | Pintor et al. |
| 8,403,983 B2 | 3/2013 | Quadri et al. |
| 8,449,599 B2 | 5/2013 | Chau et al. |
| 8,454,686 B2 | 6/2013 | Alkhatib |
| 8,460,366 B2 | 6/2013 | Rowe |
| 8,500,798 B2 | 8/2013 | Rowe et al. |
| 8,512,398 B2 | 8/2013 | Alkhatib |
| 8,568,477 B2 | 10/2013 | Lashinski et al. |
| 8,579,964 B2 | 11/2013 | Lane et al. |
| 8,585,755 B2 | 11/2013 | Chau et al. |
| 8,623,080 B2 | 1/2014 | Fogarty et al. |
| 8,628,569 B2 | 1/2014 | Benichou et al. |
| 8,628,571 B1 | 1/2014 | Hacohen et al. |
| 8,641,757 B2 | 2/2014 | Pintor et al. |
| 8,652,203 B2 | 2/2014 | Quadri et al. |
| 8,657,872 B2 | 2/2014 | Seguin |
| 8,685,085 B2 | 4/2014 | Guyenot et al. |
| 8,685,086 B2 | 4/2014 | Navia et al. |
| 8,696,742 B2 | 4/2014 | Pintor et al. |
| 8,728,155 B2 | 5/2014 | Montorfano et al. |
| 8,795,355 B2 | 8/2014 | Alkhatib |
| 8,795,356 B2 | 8/2014 | Quadri et al. |
| 8,808,371 B2 | 8/2014 | Cartledge |
| 8,834,564 B2 | 9/2014 | Tuval et al. |
| 8,840,662 B2 | 9/2014 | Salahieh et al. |
| 8,840,663 B2 | 9/2014 | Salahieh et al. |
| 8,852,272 B2 | 10/2014 | Gross et al. |
| 8,858,620 B2 | 10/2014 | Salahieh et al. |
| 8,870,948 B1 | 10/2014 | Erzberger et al. |
| 8,870,949 B2 | 10/2014 | Rowe |
| 8,876,895 B2 | 11/2014 | Tuval et al. |
| 8,894,702 B2 | 11/2014 | Quadri et al. |
| 8,911,493 B2 | 12/2014 | Rowe et al. |
| 8,926,690 B2 | 1/2015 | Kovalsky |
| 8,926,691 B2 | 1/2015 | Chau et al. |
| 8,932,358 B1 | 1/2015 | Nehls |
| 8,961,595 B2 | 2/2015 | Alkhatib |
| 8,968,395 B2 | 3/2015 | Hauser et al. |
| 8,986,370 B2 | 3/2015 | Annest |
| 8,986,373 B2 | 3/2015 | Chau et al. |
| 9,005,277 B2 | 4/2015 | Pintor et al. |
| 9,005,278 B2 | 4/2015 | Pintor et al. |
| 9,017,399 B2 | 4/2015 | Gross et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,050,188 B2 | 6/2015 | Schweich et al. |
| 9,066,801 B2 | 6/2015 | Kovalsky et al. |
| 9,072,604 B1 | 7/2015 | Melnick et al. |
| 9,084,676 B2 | 7/2015 | Chau et al. |
| 9,155,617 B2 | 10/2015 | Carpentier et al. |
| 9,168,133 B2 | 10/2015 | Spenser et al. |
| 9,173,738 B2 | 11/2015 | Murray et al. |
| 9,192,466 B2 | 11/2015 | Kovalsky et al. |
| 9,226,826 B2 | 1/2016 | Rust |
| 9,241,792 B2 | 1/2016 | Benichou et al. |
| 9,259,315 B2 | 2/2016 | Zhou et al. |
| 9,289,293 B2 | 3/2016 | Murad et al. |
| 9,295,547 B2 | 3/2016 | Costello et al. |
| 9,295,548 B2 | 3/2016 | Drews et al. |
| 9,295,550 B2 | 3/2016 | Nguyen et al. |
| 9,301,843 B2 | 4/2016 | Richardson et al. |

(56) References Cited

U.S. PATENT DOCUMENTS

| | | |
|---|---|---|
| 9,301,863 B2 | 4/2016 | Punga et al. |
| 10,449,039 B2 | 10/2019 | Ganesan et al. |
| 2001/0007956 A1 | 7/2001 | Letac et al. |
| 2001/0021872 A1 | 9/2001 | Bailey et al. |
| 2002/0151970 A1 | 10/2002 | Garrison et al. |
| 2003/0130726 A1 | 7/2003 | Thorpe et al. |
| 2005/0137689 A1 | 6/2005 | Salahieh et al. |
| 2005/0137690 A1 | 6/2005 | Salahieh et al. |
| 2005/0165479 A1 | 7/2005 | Drews et al. |
| 2007/0027533 A1 | 2/2007 | Douk |
| 2008/0004697 A1 | 1/2008 | Lichtenstein et al. |
| 2008/0015671 A1 | 1/2008 | Bonhoeffer |
| 2008/0086164 A1 | 4/2008 | Rowe |
| 2008/0103586 A1 | 5/2008 | Styrc et al. |
| 2008/0109059 A1 | 5/2008 | Gordon et al. |
| 2008/0140189 A1 | 6/2008 | Nguyen et al. |
| 2008/0221672 A1 | 9/2008 | Lamphere et al. |
| 2009/0005863 A1 | 1/2009 | Goetz et al. |
| 2010/0049315 A1 | 2/2010 | Kirson |
| 2010/0100173 A1 | 4/2010 | Lafontaine |
| 2010/0217382 A1 | 8/2010 | Chau et al. |
| 2010/0262232 A1 | 10/2010 | Annest |
| 2010/0280606 A1 | 11/2010 | Naor |
| 2010/0312333 A1 | 12/2010 | Navia et al. |
| 2011/0004296 A1 | 1/2011 | Lutter et al. |
| 2011/0022168 A1 | 1/2011 | Cartledge |
| 2011/0137397 A1 | 6/2011 | Chau et al. |
| 2011/0137410 A1 | 6/2011 | Hacohen |
| 2011/0166636 A1 | 7/2011 | Rowe |
| 2011/0208293 A1 | 8/2011 | Tabor |
| 2011/0218619 A1 | 9/2011 | Benichou et al. |
| 2011/0224785 A1 | 9/2011 | Hacohen |
| 2011/0245911 A1 | 10/2011 | Quill et al. |
| 2011/0257721 A1 | 10/2011 | Tabor |
| 2011/0282438 A1 | 11/2011 | Drews et al. |
| 2011/0295363 A1 | 12/2011 | Girard et al. |
| 2011/0301702 A1 | 12/2011 | Rust et al. |
| 2011/0319988 A1 | 12/2011 | Schankereli et al. |
| 2011/0319989 A1 | 12/2011 | Lane et al. |
| 2012/0010697 A1 | 1/2012 | Shin et al. |
| 2012/0016464 A1 | 1/2012 | Seguin |
| 2012/0035722 A1 | 2/2012 | Tuval |
| 2012/0053675 A1 | 3/2012 | Borck |
| 2012/0059458 A1 | 3/2012 | Buchbinder et al. |
| 2012/0101571 A1 | 4/2012 | Thambar et al. |
| 2012/0136430 A1 | 5/2012 | Sochman et al. |
| 2012/0310328 A1 | 12/2012 | Olson et al. |
| 2013/0172992 A1 | 7/2013 | Gross et al. |
| 2013/0184811 A1 | 7/2013 | Rowe et al. |
| 2013/0211508 A1 | 8/2013 | Lane et al. |
| 2013/0282110 A1 | 10/2013 | Schweich et al. |
| 2013/0282114 A1 | 10/2013 | Schweich et al. |
| 2013/0304200 A1 | 11/2013 | McLean et al. |
| 2014/0005778 A1 | 1/2014 | Buchbinder et al. |
| 2014/0012372 A1 | 1/2014 | Chau et al. |
| 2014/0012373 A1 | 1/2014 | Chau et al. |
| 2014/0039611 A1 | 2/2014 | Lane et al. |
| 2014/0052237 A1 | 2/2014 | Lane et al. |
| 2014/0094904 A1 | 4/2014 | Salahieh et al. |
| 2014/0200662 A1 | 7/2014 | Eftel et al. |
| 2014/0214156 A1 | 7/2014 | Navia et al. |
| 2014/0222136 A1 | 8/2014 | Geist et al. |
| 2014/0228946 A1 | 8/2014 | Chau et al. |
| 2014/0236291 A1 | 8/2014 | Schweich et al. |
| 2014/0257467 A1 | 9/2014 | Lane et al. |
| 2014/0343669 A1 | 11/2014 | Lane et al. |
| 2014/0358223 A1 | 12/2014 | Rafiee et al. |
| 2015/0039083 A1 | 2/2015 | Rafiee |
| 2015/0094802 A1 | 4/2015 | Buchbinder et al. |
| 2015/0112433 A1 | 4/2015 | Schweich et al. |
| 2015/0127096 A1 | 5/2015 | Rowe et al. |
| 2015/0150678 A1 | 6/2015 | Brecker |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0216657 A1 | 8/2015 | Braido |
| 2015/0238312 A1 | 8/2015 | Lashinski |
| 2015/0238313 A1 | 8/2015 | Spence et al. |
| 2015/0265402 A1 | 9/2015 | Centola et al. |
| 2015/0320553 A1 | 11/2015 | Chau et al. |
| 2015/0327995 A1 | 11/2015 | Morin et al. |
| 2015/0327996 A1 | 11/2015 | Fahim et al. |
| 2015/0327999 A1 | 11/2015 | Board et al. |
| 2015/0335421 A1 | 11/2015 | Figulla et al. |
| 2015/0342733 A1 | 12/2015 | Alkhatib et al. |
| 2015/0351906 A1 | 12/2015 | Hammer et al. |
| 2016/0000564 A1 | 1/2016 | Buchbinder et al. |
| 2016/0008131 A1 | 1/2016 | Christianson et al. |
| 2016/0022417 A1 | 1/2016 | Karapetian et al. |
| 2016/0045307 A1 | 2/2016 | Yohanan et al. |
| 2016/0045309 A1 | 2/2016 | Valdez et al. |
| 2016/0051362 A1 | 2/2016 | Cooper et al. |
| 2016/0074160 A1 | 3/2016 | Christianson et al. |

FOREIGN PATENT DOCUMENTS

| | | |
|---|---|---|
| WO | 2010/037141 A1 | 4/2010 |
| WO | 2011/119101 A1 | 9/2011 |
| WO | 2012/031141 A2 | 3/2012 |
| WO | 2012/103204 A2 | 8/2012 |
| WO | 2013/114214 A2 | 8/2013 |
| WO | 2014/194178 A1 | 12/2014 |
| WO | 2015/191839 A1 | 12/2015 |
| WO | 2016/149453 A1 | 9/2016 |

OTHER PUBLICATIONS

International Preliminary Report on Patentability received for PCT Patent Application No. PCT/US2016/022774, dated Sep. 28, 2017, 11 pages.

International Search Report and Written Opinion in Application No. PCT/US2016/022774, dated Jun. 9, 2016, 12 pages.

U.S. Appl. filed Dec. 16, 2009, Chau et al., U.S. Appl. No. 61/266,774.

U.S. Appl. filed Dec. 4, 2009, Chau et al., U.S. Appl. No. 61/287,099.

SYSTEMS AND METHODS FOR HEART VALVE THERAPY

CROSS-REFERENCE TO RELATED APPLICATIONS

This application is a continuation of U.S. patent application Ser. No. 15/072,588, filed Mar. 17, 2016, which claims the benefit of U.S. Provisional Application Ser. No. 62/135,276, filed Mar. 19, 2015. The disclosure of the prior applications are considered part of (and are incorporated by reference in) the disclosure of this application.

TECHNICAL FIELD

This document relates to prosthetic heart valves, such as prosthetic mitral valves that can be implanted using transcatheter techniques.

BACKGROUND

The long-term clinical effect of valve regurgitation is recognized as a significant contributor to cardiovascular related morbidity and mortality. Thus, for many therapies intended to treat the mitral valve, one primary goal is to significantly reduce or eliminate regurgitation. By eliminating the regurgitation at the mitral valve, the destructive volume overload effects on the left ventricle can be attenuated. The volume overload of mitral regurgitation (MR) relates to the excessive kinetic energy required during isotonic contraction to generate overall stroke volume in an attempt to maintain forward stroke volume and cardiac output. It also relates to the pressure potential energy dissipation of the leaking valve during the most energy-consuming portion of the cardiac cycle, isovolumetric contraction. Additionally, therapies for MR reduction can have the effect of reducing the elevated pressures in the left atrium and pulmonary vasculature reducing pulmonary edema (congestion) and shortness of breath symptomatology. Such therapies for MR reduction may also have a positive effect on the filling profile of the left ventricle (LV) and the restrictive LV physiology that can result with MR. These pathophysiologic issues indicate the potential benefits of MR therapy, but also indicate the complexity of the system and the need for a therapy to focus beyond the MR level or grade.

Some therapies for treating MR may worsen other (non-MR) existing pathologic conditions or create new pathologic conditions. One of the conditions to be managed is left ventricular outflow tract (LVOT) obstruction, or creation of high LVOT pressure gradients. Some implementations of prosthetic valve systems may physically obstruct the LVOT, and some benefits of MR reduction may thereby be dissipated or lost. Further, in some implementations of prosthetic valve systems, systolic anterior motion (SAM) of the native mitral valve leaflet(s) may cause LVOT obstruction or the creation of high LVOT pressure gradients. For example, in some cases SAM is the incursion of an anterior leaflet of the native mitral valve into the LVOT during systole.

When a prosthetic valve is implanted in a native mitral valve without removal or other restraint of the native valve leaflets, the anterior leaflet may be exposed to different flow conditions which may actually "pull" the anterior leaflet, via Bernoulli forces, toward and into the LVOT. If the anterior leaflet is drawn too far into the LVOT, there is risk of it significantly interfering with the outflow, creating a significant clinical concern. There is therefore a potential benefit to incorporating features on a prosthetic valve system to minimize the potential for SAM.

SUMMARY

This document describes prosthetic heart valves, such as prosthetic mitral valves that can be implanted using transcatheter techniques. For example, some embodiments of a transcatheter mitral valve delivery system and method described herein can be deployed to interface and anchor in cooperation with the native anatomical structures of a mitral valve. In addition, this document describes prosthetic heart valve systems and techniques that, in particular embodiments, are configured to reduce or prevent the potential for full or partial blockages of the LVOT by SAM of the anterior leaflet of the native mitral valve.

In some implementations, a prosthetic mitral valve includes a valve assembly and an anchor assembly. The anchor assembly may be configured to selectively couple with the valve assembly. The valve assembly may comprise an expandable valve frame and an occluder attached to the expandable valve frame. The anchor assembly may comprise an expandable anchor frame comprising a systolic anterior motion (SAM) containment member. The SAM containment member may be configured to be at least partially disposed behind (on an aortic side of) an anterior leaflet of a native mitral valve when the expandable anchor frame is engaged with the native mitral valve.

Such a prosthetic mitral valve may optionally include one or more of the following features. In some embodiments, the anchor assembly comprises a plurality of sub-annular projections configured to engage tissue proximate to an annulus of the native mitral valve. A space may be defined between an outwardly facing periphery of the valve assembly and the SAM containment member. Such a space may be configured to loosely contain the anterior leaflet when the prosthetic mitral valve system is engaged with the native mitral valve. In particular embodiments, SAM containment member comprises an elongate member with a first end that extends from a first portion of the expandable anchor frame and a second end that extends from a second portion of the expandable anchor frame. In various embodiments, the SAM containment member further comprises an attachment element. The prosthetic mitral valve system may further comprise a delivery system for deploying the anchor assembly. The delivery system may comprise a catheter configured to engage with the attachment element. In some embodiments, the prosthetic mitral valve system may further comprise a delivery system for deploying the anchor assembly. The delivery system may comprise a control wire configured to engage with the attachment element. In various embodiments, the SAM containment member comprises an elongate member that extends from a hub of the expandable anchor frame, and wherein the elongate member defines a first width. Optionally, the SAM containment member may include an end portion extending from the elongate member. The end portion may define a second width that is greater than the first width of the elongate member, and the end portion may be configured to be disposed behind the anterior leaflet when the expandable anchor frame is engaged with the native mitral valve. In particular embodiments of the prosthetic mitral valve system, the expandable anchor frame may include a single SAM containment member.

In another implementation, a prosthetic mitral valve system comprises an expandable frame with an occluder coupled thereto, and a delivery system for transcatheter deployment of the expandable frame within a native mitral valve. The expandable frame may comprise a systolic anterior motion (SAM) containment member that is configured to be at least partially disposed behind an anterior leaflet of the native mitral valve when the expandable frame is engaged with the native mitral valve. The SAM containment member may comprise an attachment element. The delivery system may be releasably coupleable with the attachment element.

Such a prosthetic mitral valve system may optionally include one or more of the following features. In some embodiments, the attachment element comprises an eyelet. Optionally, the eyelet includes eyelet threads. In some embodiments, the delivery system comprises a member with threads that are complementary with the eyelet threads. In particular embodiments, the delivery system comprises a control wire that engages with the eyelet. In various embodiments, the SAM containment member comprises an elongate member that extends from a hub of the expandable frame. The elongate member defines a first width. In particular embodiments, the SAM containment member includes an end portion extending from the elongate member, and the end portion defines a second width that is greater than the first width of the elongate member. The end portion may be configured to be disposed behind the anterior leaflet when the expandable anchor frame is engaged with the native mitral valve. Optionally, the expandable frame includes a single SAM containment member.

In another implementation, a method for deploying a prosthetic mitral valve system within a native mitral valve of a patient includes: navigating a delivery sheath of a prosthetic mitral valve delivery system within the patient such that a distal end of the delivery sheath is positioned adjacent the native mitral valve; expressing an anchor assembly of the prosthetic mitral valve system from the distal end of the delivery sheath such that the anchor assembly at least partially expands, the anchor assembly configured to selectively mate with a valve assembly of the prosthetic mitral valve system; engaging the anchor assembly with the native mitral valve; and after engaging the anchor assembly with the native mitral valve, deploying a systolic anterior motion (SAM) containment member such that the SAM containment member becomes at least partially disposed behind an anterior leaflet of the native mitral valve.

Such a method may optionally include one or more of the following features. The method may further comprise, after deploying the SAM containment member, mating the valve assembly with the anchor assembly. In some embodiments, the method may further comprise, prior to deploying the SAM containment member, mating the valve assembly with the anchor assembly. In particular implementations, when the anchor assembly is engaged with the native mitral valve, and prior to deploying the SAM containment member, native leaflets of the native mitral valve continue to function without significant interference from the anchor assembly. In various implementations, wherein when the anchor assembly is engaged with the native mitral valve, and after deploying the SAM containment member, native leaflets of the native mitral valve continue to function without significant interference from the anchor assembly. Optionally, the anchor assembly comprises one or more sub-annular support arms each having an anchor foot. In some implementations, engaging the anchor assembly with the native mitral valve comprises disposing each anchor foot within a sub-annular gutter of the native mitral valve. In some embodiments, the method may further comprise mating the valve assembly with the anchor assembly, wherein the anterior leaflet is loosely contained between the SAM containment member and an exterior surface of the valve assembly. Optionally, the SAM containment member is biased to be at least partially disposed behind the anterior leaflet. Deploying the SAM containment member may comprise detaching the SAM containment member from a member of the prosthetic mitral valve delivery system such that the SAM containment member is free to self-reconfigure to become at least partially disposed behind the anterior leaflet. In some embodiments, deploying the SAM containment member comprises using a member of the prosthetic mitral valve delivery system to deflect the SAM containment member to be at least partially disposed behind the anterior leaflet.

In another implementation, a method for transcatheter deployment of a prosthetic mitral valve within a native mitral valve of a patient includes engaging the prosthetic mitral valve with the native mitral valve, and after engaging the prosthetic mitral valve with the native mitral valve, deploying a systolic anterior motion (SAM) containment member of the prosthetic mitral valve such that the SAM containment member becomes at least partially disposed behind an anterior leaflet of the native mitral valve. In some implementations of the method, the anterior leaflet is loosely contained between the SAM containment member and an exterior surface of the prosthetic mitral valve. Optionally, the SAM containment member is biased to be at least partially disposed behind the anterior leaflet. Deploying the SAM containment member may comprise detaching the SAM containment member from a delivery system member such that the SAM containment member is free to self-reconfigure to become at least partially disposed behind the anterior leaflet. In some implementations, portions of the SAM containment member engage one or more lateral edges of the anterior leaflet or chordae to spread or widen the anterior leaflet to thereby restricting movement of the anterior leaflet.

In another implementation, an anchor assembly of a prosthetic mitral valve system includes an expandable anchor frame that is adjustable between a radially compressed delivery condition and a radially expanded deployed condition in which the expandable anchor frame is configured to engage with a native mitral valve. The anchor assembly may be configured to selectively mate with a subsequently deliverable valve assembly of a prosthetic mitral valve system. The expandable anchor frame may include a systolic anterior motion (SAM) containment member that is configured to be at least partially disposed behind an anterior leaflet of the native mitral valve when the expandable anchor frame is engaged with the native mitral valve.

Such an anchor assembly may optionally include one or more of the following features. In some embodiments, the SAM containment member comprises an elongate member with a first end that extends from a first portion of the expandable anchor frame and a second end that extends from a second portion of the expandable anchor frame. Optionally, the SAM containment member further comprises an attachment element configured to releasably engage with a portion of a delivery system. In particular embodiments, the attachment element comprises an eyelet. In various embodiments, the SAM containment member comprises an elongate member that extends from a generally central, lower hub of the expandable anchor frame. The elongate member defines a first width. In some embodiments, the SAM containment member includes an end portion extending from the elongate member. In particular embodiments, the end portion defines a second width that is greater than the first width of the elongate member. Optionally, the end portion is configured to be disposed behind the anterior leaflet when the expandable anchor frame is engaged with the native mitral valve. In some embodiments, the expandable anchor frame includes a single SAM containment member.

Some or all of the embodiments described herein may provide one or more of the following advantages. First, some embodiments of the prosthetic mitral valve systems provided herein can be used in a completely percutaneous/transcatheter mitral replacement procedure that is safe, reliable, and repeatable by surgeons and/or interventional cardiologists of a variety of different skill levels. For example, in some implementations the prosthetic mitral valve system can establish a reliable and consistent anchor/substrate to which the valve/occluder structure subsequently engages. Thus, the prosthetic mitral valve system can be specifically designed to make use of the geometry/mechanics of the native mitral valve to create sufficient holding capability. In one particular aspect, the anatomical gutter found below a native mitral valve annulus can be utilized as a site for anchoring the prosthetic mitral valve system, yet the anchoring structure can be deployed in a matter that maintains native leaflet function of the mitral valve, thereby providing the ability to completely separate and stage the implantation of the components of the prosthetic mitral valve system. Accordingly, some embodiments of the prosthetic mitral valve systems described herein are configured to be implanted in a reliable, repeatable, and simplified procedure that is broadly applicable to a variety of patients and physicians, while also employing a significantly less invasive method.

Second, in particular embodiments, the prosthetic mitral valve system can include two different expandable components (e.g., an anchor assembly and a valve assembly) that are separately delivered to the implantation site, and both components can abut and engage with native heart tissue at the mitral valve. For example, the first component (e.g., the anchor assembly) can be configured to engage with the heart tissue that is at or proximate to the annulus of the native mitral valve, and the second component (e.g., the valve assembly) can be configured to provide a seal interface with native valve leaflets of the mitral valve.

Third, some embodiments of the prosthetic mitral valve systems described herein are configured with a SAM containment member feature. Multiple types of SAM containment members are described herein. SAM containment members can reduce or prevent the potential for a natural mitral valve anterior leaflet to "flop" outward and/or from being drawn by a Venturi effect into the LVOT. Accordingly, the SAM containment members can reduce the risk of full or partial blockages of the LVOT. In some patient scenarios, the potential for suffering future adverse health events, such as heart failure, is thereby reduced.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

This disclosure describes embodiments of a prosthetic heart valve system, such as prosthetic mitral valve systems, and transcatheter systems and methods for implanting prosthetic heart valve systems. In some embodiments, the prosthetic mitral valve system can be deployed to interface and anchor in cooperation with the native anatomical structures of a mitral valve (and, optionally, in a manner that permits the continued natural function of the chordae tendineae of the native mitral valve leaflets even after the anchor component is deployed). As described in more detail below, FIGS. 1-7 and 15-34 describe a transcatheter mitral valve delivery system and method by which the prosthetic mitral valve system can be deployed to interface and anchor in cooperation with the anatomical structures of a native mitral valve. Also, in FIGS. 9-12 and 20-34, multiple embodiments of prosthetic mitral valve SAM containment members are described by which the prosthetic valves prevent a native anterior leaflet from "flopping" or being drawn outward into the LVOT to create an obstruction of the LVOT.

Figure 1:
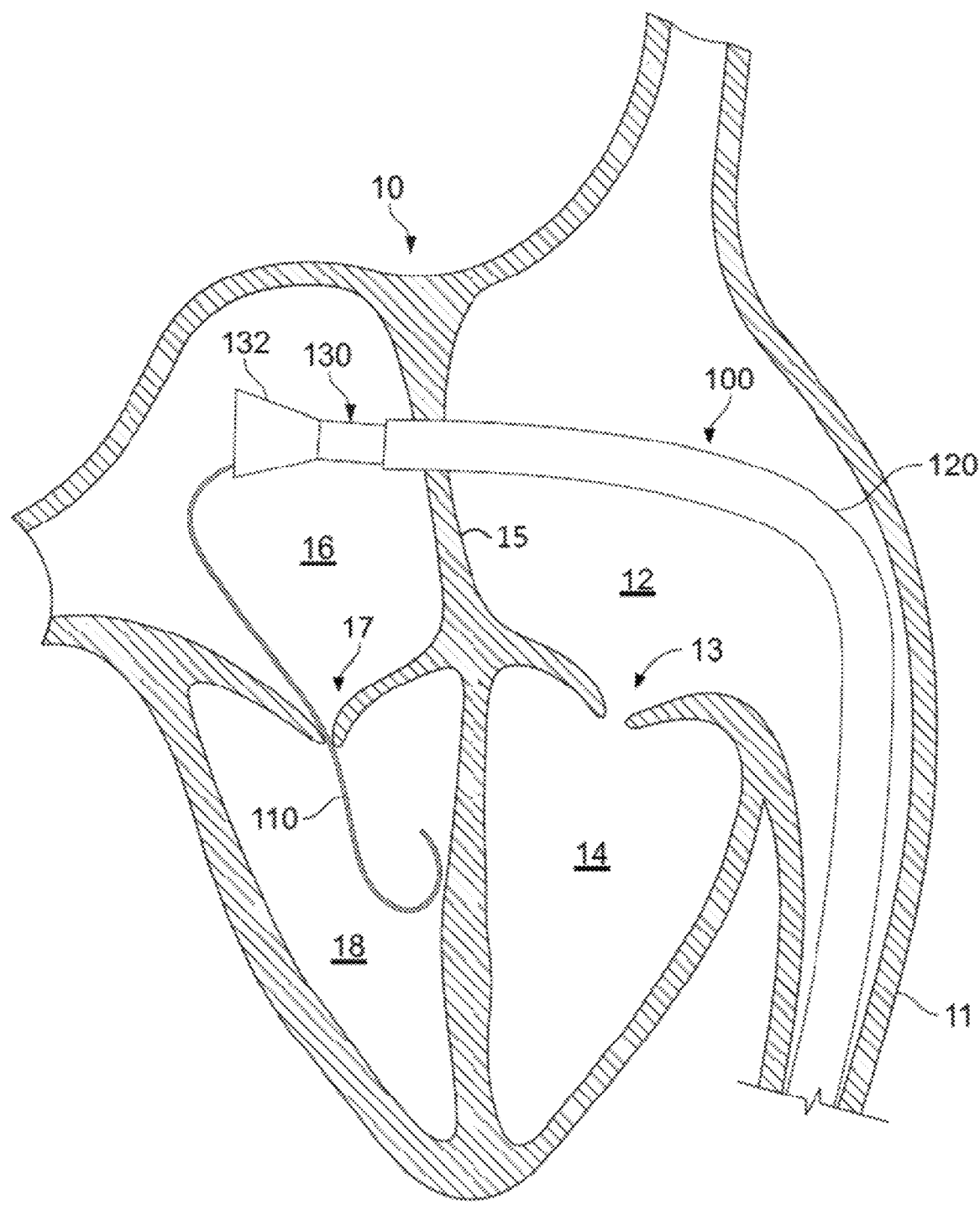
FIG. 1 is a perspective view of a portion of a prosthetic mitral valve deployment system in a cross-sectional view of a native human heart, in accordance with some embodiments.

Referring to FIG. 1, an example transcatheter mitral valve delivery system 100 can be navigated through a patient's vasculature to obtain access to the patient's heart 10. The transcatheter delivery system 100 facilitates implantation of a prosthetic mitral valve in a beating heart 10 using a percutaneous, vessel cutdown, or minimally invasive technique (without open-chest surgery). In some implementations, the transcatheter delivery system 100 is used in conjunction with one or more imaging modalities such as x-ray fluoroscopy, echocardiography, magnetic resonance imaging, computed tomography (CT), and the like.

The heart 10 (depicted in cross-section from a posterior perspective) includes a right atrium 12, a right ventricle 14, a left atrium 16, and a left ventricle 18. A tricuspid valve 13 separates the right atrium 12 from the right ventricle 14. A mitral valve 17 separates the left atrium 16 from the left ventricle 18. An atrial septum 15 separates the right atrium 12 from the left atrium 16. An inferior vena cava 11 is confluent with the right atrium 12. It should be understood that this depiction of the heart 10 is somewhat stylized. The same is true for FIGS. 2-4. FIGS. 1-4 provide general depictions of the approach to the mitral valve 17 that is used in some implementations. But, the commissural cross-sectional views of FIG. 5 and thereafter more accurately depict the orientation of the prosthetic mitral valves in relation to the heart 10.

In the depicted embodiment, the delivery system 100 includes a guidewire 110, a primary deflectable catheter 120, and an anchor delivery sheath 130. Additional components of the delivery system 100 will be described further below. The anchor delivery sheath 130 is slidably (and rotationally) disposed within a lumen of the primary deflectable catheter 120. The guidewire 110 is slidably disposed within a lumen of the anchor delivery sheath 130. In this depiction, the anchor delivery sheath 130 has been partially extended relative to the primary deflectable catheter 120, allowing a flared portion 132 to expand outward, as described further below.

In the depicted implementation, the guidewire 110 is installed into the heart 10 prior to the other components of the delivery system 100. In some embodiments, the guidewire 110 has a diameter of about 0.035 inches (about 0.89 mm). In some embodiments, the guidewire 110 has a diameter in a range of about 0.032 inches to about 0.038 inches (about 0.8 mm to about 0.97 mm). In some embodiments, the guidewire 110 has a diameter smaller than 0.032 inches (about 0.80 mm) or larger than 0.038 inches (about 0.97 mm). In some embodiments, the guidewire 110 is made of materials such as, but not limited to, nitinol, stainless steel, high-tensile-strength stainless steel, and the like, and combinations thereof. The guidewire 110 may include various tip designs (e.g., J-tip, straight tip, etc.), tapers, coatings, covers, radiopaque (RO) markers, and other features. In some embodiments, the guidewire 110 has one or more portions with differing lateral stiffnesses, column strengths, lubricity, and/or other physical properties in comparison to other portions of the guidewire 110.

In some implementations, the guidewire 110 is percutaneously inserted into a femoral vein of the patient. The guidewire 110 is routed to the inferior vena cava 11 and into the right atrium 12. After creating an opening in the atrial septum 15 (e.g., a trans-septal puncture of the fossa ovalis), the guidewire 110 is routed into the left atrium 16. Lastly, the guidewire 110 is routed through the mitral valve 17 and into the left ventricle 18. In some implementations, the guidewire 110 can be installed into the heart 10 along other anatomical pathways. The guidewire 110 thereafter serves as a rail over which other components of the delivery system 100 are passed.

In the depicted implementation, the primary deflectable catheter 120 is installed by pushing it over the guidewire 110. In some implementations, a dilator tip is used in conjunction with the primary deflectable catheter 120 as the primary deflectable catheter 120 is advanced over the guidewire 110. Alternatively, a balloon catheter could be used as the initial dilation means. After the distal end of the primary deflectable catheter 120 reaches the left atrium 16, the dilator tip can be withdrawn. In some embodiments, the distal end portion of the primary deflectable catheter 120 is steerable. Using steering, the distal end portion of the primary deflectable catheter 120 can be oriented as desired in order to navigate the patient's anatomy. For example, the primary deflectable catheter 120 can be angled within the right atrium 12 to navigate the primary deflectable catheter 120 from the inferior vena cava 11 to the atrial septum 15.

In some embodiments, the primary deflectable catheter 120 has an outer diameter of about 28 Fr (about 9.3 mm), or about 30 Fr (about 10.0 mm). In some embodiments, the primary deflectable catheter 120 has an outer diameter in the range of about 26 Fr to about 34 Fr (about 8.7 mm to about 11.3 mm). In some embodiments, the primary deflectable catheter 120 has an outer diameter in the range of about 20 Fr to about 28 Fr (about 6.7 mm to about 9.3 mm).

The primary deflectable catheter 120 can comprise a tubular polymeric or metallic material. For example, in some embodiments the primary deflectable catheter 120 can be made from polymeric materials such as, but not limited to, polytetrafluoroethylene (PTFE), fluorinated ethylene propylene (FEP), HYTREL®, nylon, PICOFLEX®, PEBAX®, TECOFLEX®, and the like, and combinations thereof. In alternative embodiments, the primary deflectable catheter 120 can be made from metallic materials such as, but not limited to, nitinol, stainless steel, stainless steel alloys, titanium, titanium alloys, and the like, and combinations thereof. In some embodiments, the primary deflectable catheter 120 can be made from combinations of such polymeric and metallic materials (e.g., polymer layers with metal braid, coil reinforcement, stiffening members, and the like, and combinations thereof). In some embodiments, the primary deflectable catheter 120 can comprise a slotted tube.

The example delivery system 100 also includes the anchor delivery sheath 130. In some implementations, after the primary deflectable catheter 120 is positioned with its distal end in the left atrium 16, the anchor delivery sheath 130 is installed into a lumen of the primary deflectable catheter 120 (over the guidewire 110) and advanced through the primary deflectable catheter 120. As described further below, in some embodiments the anchor delivery sheath 130 is preloaded with a prosthetic valve anchor assembly and other components of the delivery system 100.

In some embodiments, the anchor delivery sheath 130 can be made from the materials described above in reference to the primary deflectable catheter 120. In some embodiments, the anchor delivery sheath 130 has an outer diameter in the range of about 20 Fr to about 28 Fr (about 6.7 mm to about 9.3 mm). In some embodiments, the anchor delivery sheath 130 has an outer diameter in the range of about 14 Fr to about 24 Fr (about 4.7 mm to about 8.0 mm).

In the depicted embodiment, the anchor delivery sheath 130 includes a flared distal end portion 132. In some embodiments, no such flared distal end portion 132 is included. The flared distal end portion 132 can collapse to a lower profile when constrained within the primary deflectable catheter 120. When the flared distal end portion 132 is expressed from the primary deflectable catheter 120, the flared distal end portion 132 can self-expand to the flared shape. In some embodiments, the material of the flared distal end portion 132 includes pleats or folds, may be a continuous flared end or may be separated into sections such as flower petals, and may include one or more resilient elements that bias the flared distal end portion 132 to assume the flared configuration in the absence of restraining forces (such as from containment within the primary deflectable catheter 120). The flared distal end portion 132 can be advantageous, for example, for recapturing the anchor assembly within the lumen of the anchor delivery sheath 130 after the anchor assembly has been expressed from the flared distal end portion 132.

In some embodiments, the maximum outer diameter of the flared distal end portion 132 is in a range of about 30 Fr to about 34 Fr (about 10.0 mm to about 11.3 mm). In some embodiments, the maximum outer diameter of the flared distal end portion 132 is in a range of about 32 Fr to about 44 Fr (about 10.7 mm to about 14.7 mm). In some embodiments, the maximum outer diameter of the flared distal end portion 132 is in a range of about 24 Fr to about 30 Fr (about 8.0 mm to about 10.0 mm). In some embodiments, the maximum outer diameter of the flared distal end portion 132 is less than about 24 Fr (about 8.0 mm) or greater than about 44 Fr (about 14.7 mm).

Figure 2:
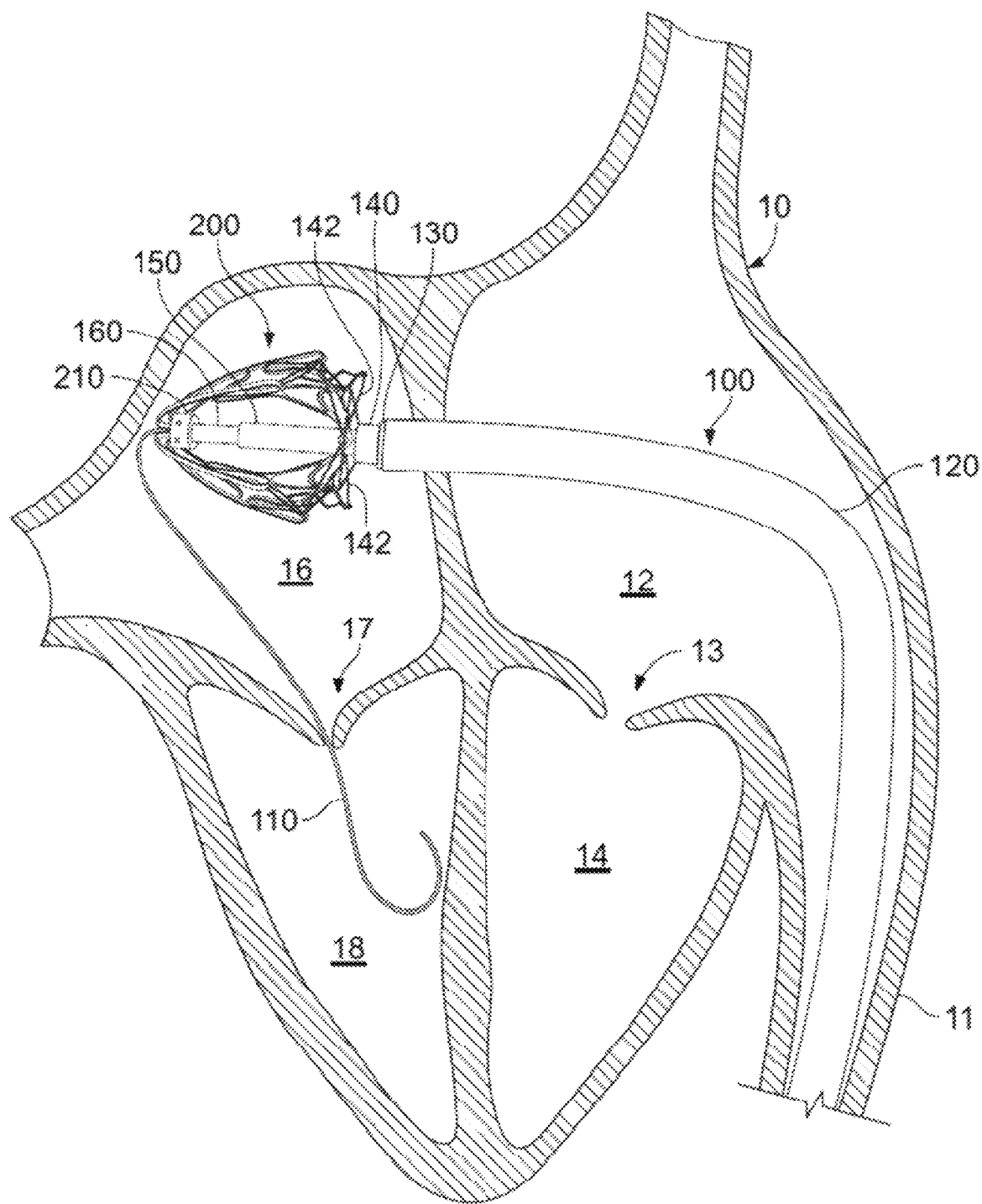
FIG. 2 shows a perspective view of a prosthetic mitral valve anchor assembly in the left atrium of the heart after the anchor assembly has emerged from an anchor delivery sheath of the deployment system of FIG. 1

Referring to FIG. 2, additional components of the example delivery system 100 can include a proximal control sheath 140, a secondary deflectable catheter 150, and a distal pusher catheter 160. The proximal control sheath 140 is slidably disposed within a lumen of the anchor delivery sheath 130. The secondary deflectable catheter 150 is slidably disposed within a lumen of the proximal control sheath 140. The distal pusher catheter 160 is slidably disposed within a lumen of the secondary deflectable catheter 150. These components of the delivery system 100 can be manipulated by a clinician operator to control the position and orientation of an anchor assembly 200. The anchor assembly 200 is slidably disposed over the guidewire 110.

In some implementations of delivery system 100, one or more of the proximal control sheath 140, the secondary deflectable catheter 150, the distal pusher catheter 160, and the anchor assembly 200 have been loaded into the anchor delivery sheath 130 prior to the advancement of the anchor delivery sheath 130 into the primary deflectable catheter 120 as shown in FIG. 1. That is, in some cases the proximal control sheath 140, the secondary deflectable catheter 150, the distal pusher catheter 160, and/or the anchor assembly 200 are already installed in the anchor delivery sheath 130 as the anchor delivery sheath 130 is distally advanced into the primary deflectable catheter 120 to attain the arrangement shown in FIG. 1. In other implementations, one or more of the proximal control sheath 140, the secondary deflectable catheter 150, the distal pusher catheter 160, and the anchor assembly 200 are distally advanced into the anchor delivery sheath 130 after the anchor delivery sheath 130 has been advanced into the primary deflectable catheter 120 to attain the arrangement shown in FIG. 1.

The distal pusher catheter 160 is releasably coupled with a hub 210 of the anchor assembly 200. A proximal end of the anchor assembly 200 is also releasably coupled to the proximal control sheath 140 by one or more control wires 142. While the depicted embodiment includes one control wire 142, in some embodiments two, three, four, five, or more than five control wires are included.

In some embodiments, the position of the anchor assembly 200 can be controlled by manipulating the positions of the distal pusher catheter 160 and/or the proximal control sheath 140. For example, in the depicted embodiment the anchor assembly 200 can be expressed out from the anchor delivery sheath 130 (as shown in FIG. 2) by moving the distal pusher catheter 160 and/or the proximal control sheath 140 distally in relation to the anchor delivery sheath 130. In some implementations, the expression of the anchor assembly 200 is caused by proximally pulling back the anchor delivery sheath 130 while generally maintaining the positions of the distal pusher catheter 160 and/or the proximal control sheath 140. In some implementations, the expression of the anchor assembly 200 is caused by a combination of proximally pulling back the anchor delivery sheath 130 while distally extending the positions of the distal pusher catheter 160 and/or the proximal control sheath 140.

As the anchor assembly 200 emerges from the confines of the anchor delivery sheath 130, the anchor assembly 200 expands from a low-profile delivery configuration to a partially expanded configuration (as shown in FIG. 2). The extent of expansion of the anchor assembly 200 can be at least partially controlled by the relative positioning of the proximal control sheath 140 in relation to the distal pusher catheter 160. For instance, as the proximal control sheath 140 is moved proximally in relation to the distal pusher catheter 160, the anchor assembly 200 is axially elongated and radially contracted. Conversely, as the proximal control sheath 140 is moved distally in relation to the distal pusher catheter 160, the anchor assembly 200 is axially shortened and radially expanded. In some implementations, this control of the radial size of the anchor assembly 200 is used by a clinician during the process of deploying the anchor assembly 200 within the native mitral valve 17, as described further below. As described further below, the control wire 142 can also be used to control some radial expansion of the anchor assembly 300 (without changing the relative distance of the proximal control sheath 140 in relation to the distal pusher catheter 160).

Figure 37:
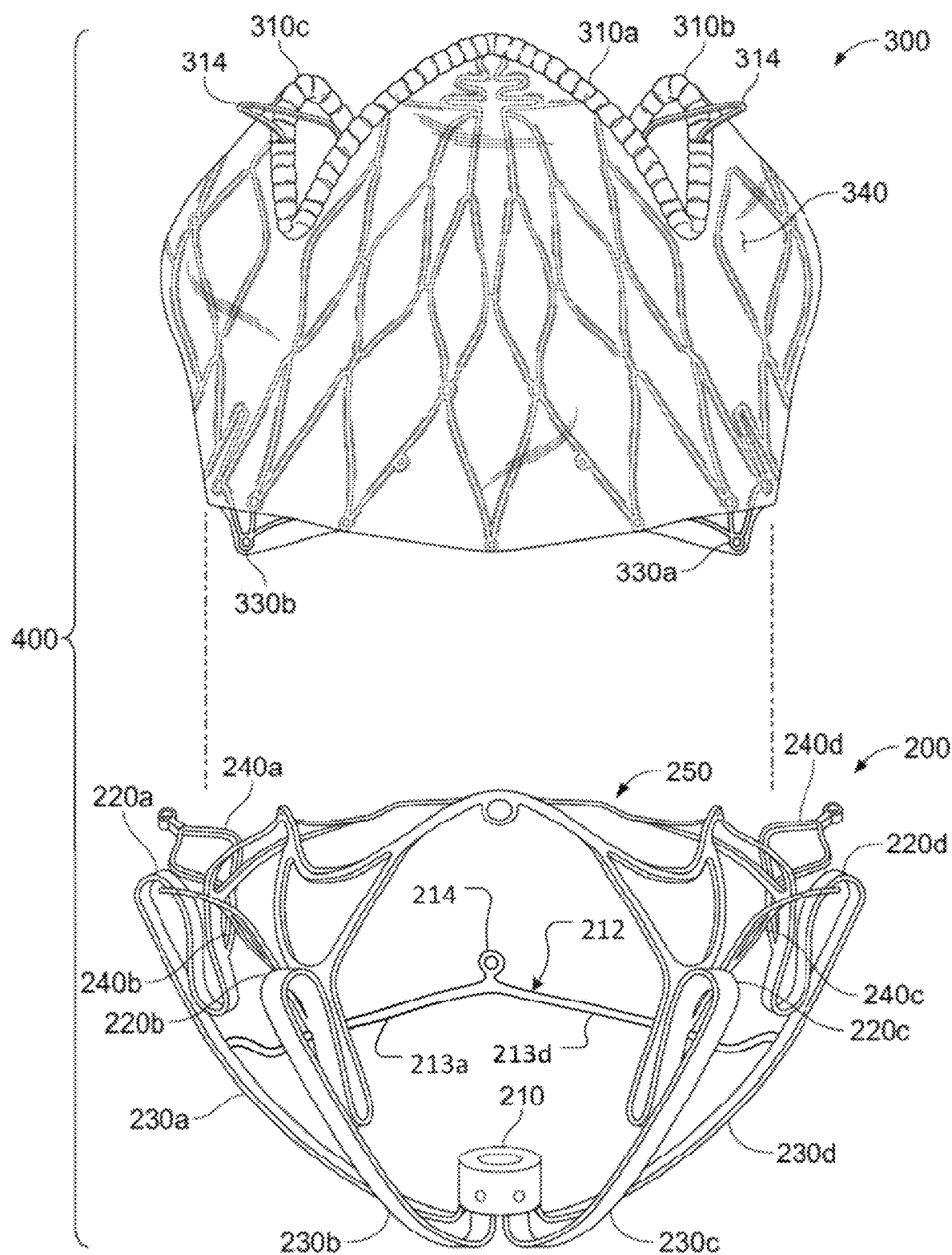
FIG. 37 is an exploded posterior side view of an anchor assembly and valve assembly of FIGS. 16-19, in accordance with some embodiments.

It should be understood that the prosthetic mitral valves provided herein are comprised of an anchor assembly 200 and a separable valve assembly (e.g., refer to FIG. 37). The anchor assembly 200 is deployed to an arrangement interfacing within the native mitral valve 17 prior to deployment of the valve assembly. Said differently, after implanting the anchor assembly 200 within the native mitral valve 17, the valve assembly can then be deployed within the anchor assembly 200 and within the native mitral valve 17 (as described further below). Therefore, it can be said that the prosthetic mitral valves provided herein are deployed using a staged implantation method. That is, the anchor assembly 200 is deployed in one stage, and the valve assembly is deployed in a subsequent stage. In some embodiments, as described further below, a SAM containment member is deployed as part of the deployment method. In some implementations, the deployment of the valve assembly takes place right after the deployment of the anchor assembly 200 (e.g., during the same medical procedure). In some implementations, the deployment of the valve assembly takes place hours, days, weeks, or even months after the deployment of the anchor assembly 200 (e.g., during a subsequent medical procedure).

The staged implantation method of the prosthetic mitral valves provided herein is facilitated by the fact that when the anchor assembly 200 itself is implanted within the native mitral valve 17, the native mitral valve 17 continues to function essentially as before the implantation of the anchor assembly 200 without a significant impact on cardiovascular physiology. That is the case because, as described further below, the anchor assembly 200 interfaces and anchors within structural aspects of the native mitral valve 17 without substantially interfering with the leaflets or chordae tendineae of the native mitral valve 17.

Still referring to FIG. 2, in the depicted arrangement the distal end portion of the secondary deflectable catheter 150 is located at least partially internally within the anchor assembly 200. The secondary deflectable catheter 150 can be manipulated by a clinician operator to reversibly bend the distal end portion of the secondary deflectable catheter 150. As the secondary deflectable catheter 150 is bent by the clinician, other components of the delivery system 100 may bend along with the secondary deflectable catheter 150. For example, one or more of the distal pusher 160 and the proximal control sheath 140 may bend in response to the bending of the deflectable catheter 150. Because the anchor assembly 200 is coupled to the distal pusher 160 and the proximal control sheath 140, the anchor assembly 200 can, in turn, be rotated by bending the secondary deflectable catheter 150.

Figure 3:
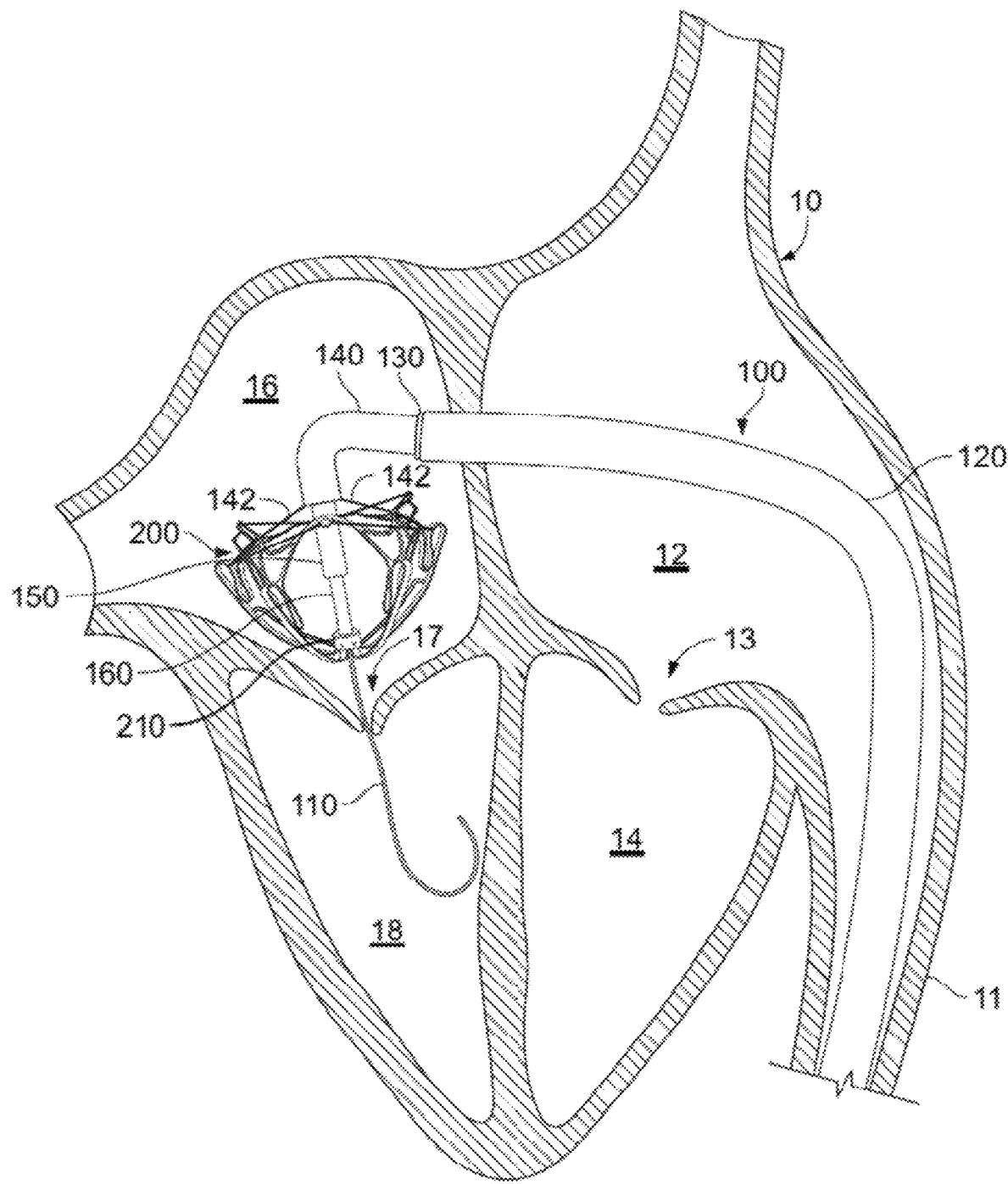
FIG. 3 shows a perspective view of the anchor assembly of FIG. 2 after being rotated in the left atrium so as to orient the anchor assembly generally perpendicular to the native mitral valve.

Referring to FIG. 3, as described above, the secondary deflectable catheter 150 can be articulated (also referred to as steered, deflected, bent, curved, etc.) to pivot laterally (pan, rotate, etc.) the anchor assembly 200 while the anchor assembly 200 is within the left atrium 16. Such rotation of the anchor assembly 200 is advantageous, for example, to orient the anchor assembly 200 in a desired relationship to the native mitral valve 17 in preparation for implanting the anchor assembly 200 within the native mitral valve 17. In some implementations, it is desirable to orient the anchor assembly 200 so that its longitudinal axis is generally perpendicular to the native mitral valve 17. The lateral pivoting of the partially or fully expanded anchor assembly 200 within the atrium 16 may be advantageous versus having to pivot laterally the anchor assembly 200 while it is still constrained within a delivery sheath, as the latter assembly is a relatively large and stiff catheter assembly.

In preparation for engaging the anchor assembly 200 with the native mitral valve 17, the clinician operator may manipulate the radial size of the anchor frame 200 so that the anchor frame 200 can be passed through the native mitral valve 17 without damaging the native mitral valve 17. For example, the clinician can move the proximal control sheath 140 proximally in relation to the distal pusher catheter 160 to radially contract the anchor assembly 200. With the anchor assembly 200 radially contracted, the anchor frame 200 can be safely passed through the native mitral valve 17 without damaging the native mitral valve 17.

Figure 4:
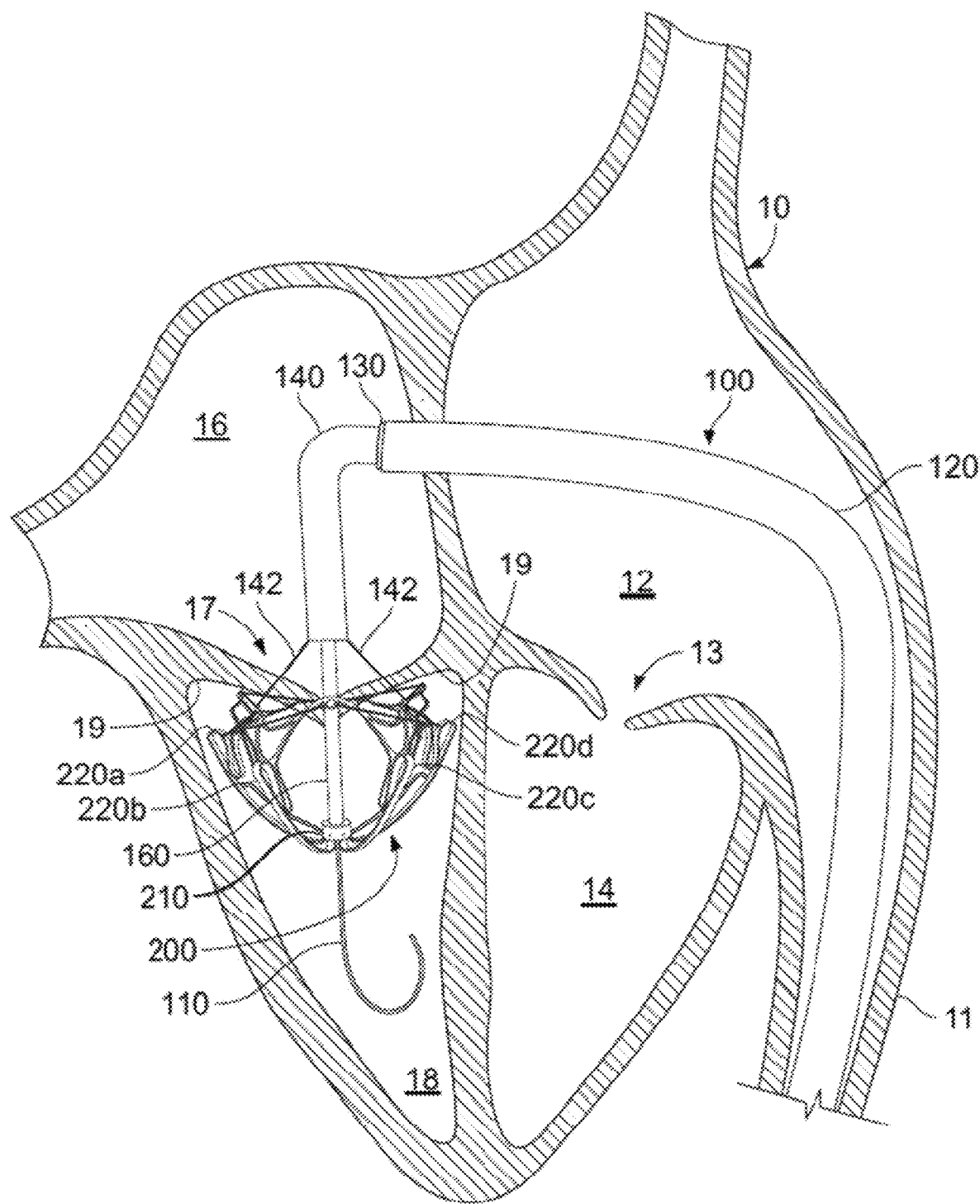
FIG. 4 shows a perspective view of the anchor assembly of FIG. 3 after being partially advanced through the native mitral valve so as to position projections of the anchor assembly below a sub-annular gutter of the native mitral valve.

Referring to FIG. 4, while the secondary deflectable catheter 150 is retained in its bent configuration as described in reference to FIG. 3, the distal pusher catheter 160 and the proximal control sheath 140 can be simultaneously advanced. Because the distal pusher catheter 160 is releasably coupled to the hub 210 of the anchor assembly 200, and because the proximal control sheath 140 is releasably coupled to the proximal end of the anchor assembly 200 via the one or more wires 142a and 142b, generally simultaneous advancement of the distal pusher catheter 160 and the proximal control sheath 140 results in advancement of the anchor assembly 200. The anchor assembly 200 is advanced such that the distal end of anchor assembly 200 is within the left ventricle 18 while the proximal end of the anchor assembly 200 is within the left atrium 16. Hence, some portions of the anchor assembly 200 are on each side of the native mitral valve 17.

In the depicted embodiment, the anchor assembly 200 includes four anchor feet: a lateral anterior foot 220a, a lateral posterior foot 220b, a medial posterior foot 220c, and a medial anterior foot 220d. In some embodiments, fewer or more anchor feet may be included (e.g., two, three, five, six, or more than six). In some embodiments, the anchor feet 220a, 220b, 220c, and 220d are portions of the anchor assembly 200 that are configured for contact with a sub-annular gutter 19 of the native mitral valve 17, without penetrating tissue of the native mitral valve 17. Accordingly, the anchor feet 220a, 220b, 220c, and 220d have atraumatic surfaces that are generally comparable to feet. However, in some embodiments one or more of the anchor feet 220a, 220b, 220c, and 220d are configured to penetrate tissue and may have anchor features such as barbs, coils, hooks, and the like.

In the arrangement of FIG. 4, the anchor feet 220a, 220b, 220c, and 220d are positioned below the sub-annular gutter 19. In this arrangement, the radial size of the anchor assembly 200 can be increased to align the anchor feet 220a, 220b, 220c, and 220d with the sub-annular gutter 19. For example, the clinician can move the proximal control sheath 140 distally in relation to the distal pusher catheter 160 to radially expand the anchor assembly 200 to align the anchor feet 220a, 220b, 220c, and 220d with the sub-annular gutter 19. Such alignment can be performed in preparation for seating the anchor feet 220a, 220b, 220c, and 220d within the sub-annular gutter 19.

Figure 5:
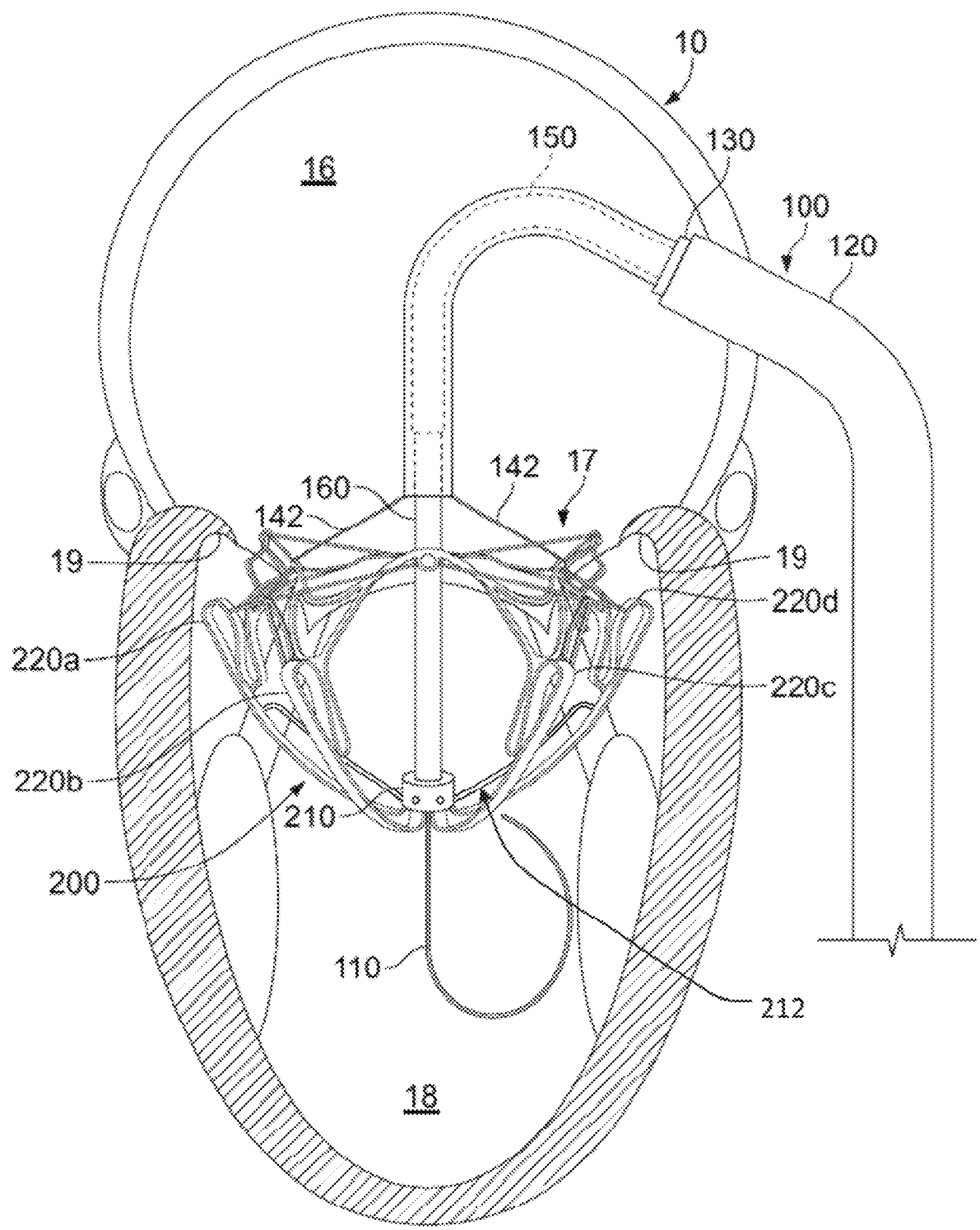
FIG. 5 shows a perspective view of the anchor assembly in a similar arrangement as shown in FIG. 4, but in a commissural cross-sectional view of the heart (from the left side of the heart).

Referring to FIG. 5, a commissural cross-sectional view of the heart 10 provides another perspective of the anchor assembly 200 in the same arrangement in relation to the native mitral valve 17 as shown in FIG. 4. This commissural cross-sectional view of the heart 10 is a cross-sectional view taken through the mitral valve 17 along a plane through the left atrium 16 and left ventricle 18 that is parallel to the line that intersects the two commissures of the mitral valve 17 (as described further in reference to FIG. 8 below). In the following FIGS. 5-7 and 13-17, the commissural cross-sectional view of the heart 10 will be used to describe the delivery system 100 and methods for deploying the prosthetic mitral valves provided herein. The view in FIGS. 5-7 and 13-17 is slightly tilted so that better visualization of the anchor assembly 200 is provided.

The anchor feet 220a, 220b, 220c, and 220d are positioned below the sub-annular gutter 19. In this position, the anchor feet 220a, 220b, 220c, and 220d are positioned under the systolic and diastolic excursions of the leaflets of the native mitral valve 17. In this orientation, the anchor feet 220a, 220b, 220c, and 220d can be aligned with the sub-annular gutter 19 in preparation for seating the anchor feet 220a, 220b, 220c, and 220d within the sub-annular gutter 19.

In this figure, portions of an example SAM containment member 212 are in view. In the depicted embodiment, the SAM containment member 212 extends from the anchor assembly 200. For example, the SAM containment member 212 comprises an elongate member with a first end that extends from a first portion of the anchor assembly 200 and a second end that extends from a second portion of the anchor assembly 200. In particular embodiments, the SAM containment member 212 is integrally formed as part of the anchor assembly 200. In specific embodiments, the SAM containment member 212, or portions thereof, may be formed separately from the anchor assembly 200 and thereafter attached to the anchor assembly 200.

The SAM containment member 212 can be arranged in a pre-deployed configuration as shown. As described further below, the SAM containment member 212 can be reconfigured to a deployed configuration such that the SAM containment member 212 physically prevents an anterior leaflet of a native mitral valve from obstructing the LVOT. In some embodiments, the SAM containment member 212 is biased to self-reconfigure to the deployed configuration when the SAM containment member 212 is unconstrained. While one particular embodiment of the SAM containment member 212 is depicted, it should be understood that multiple SAM containment member embodiments are envisioned and within the scope of this disclosure.

Figure 6:
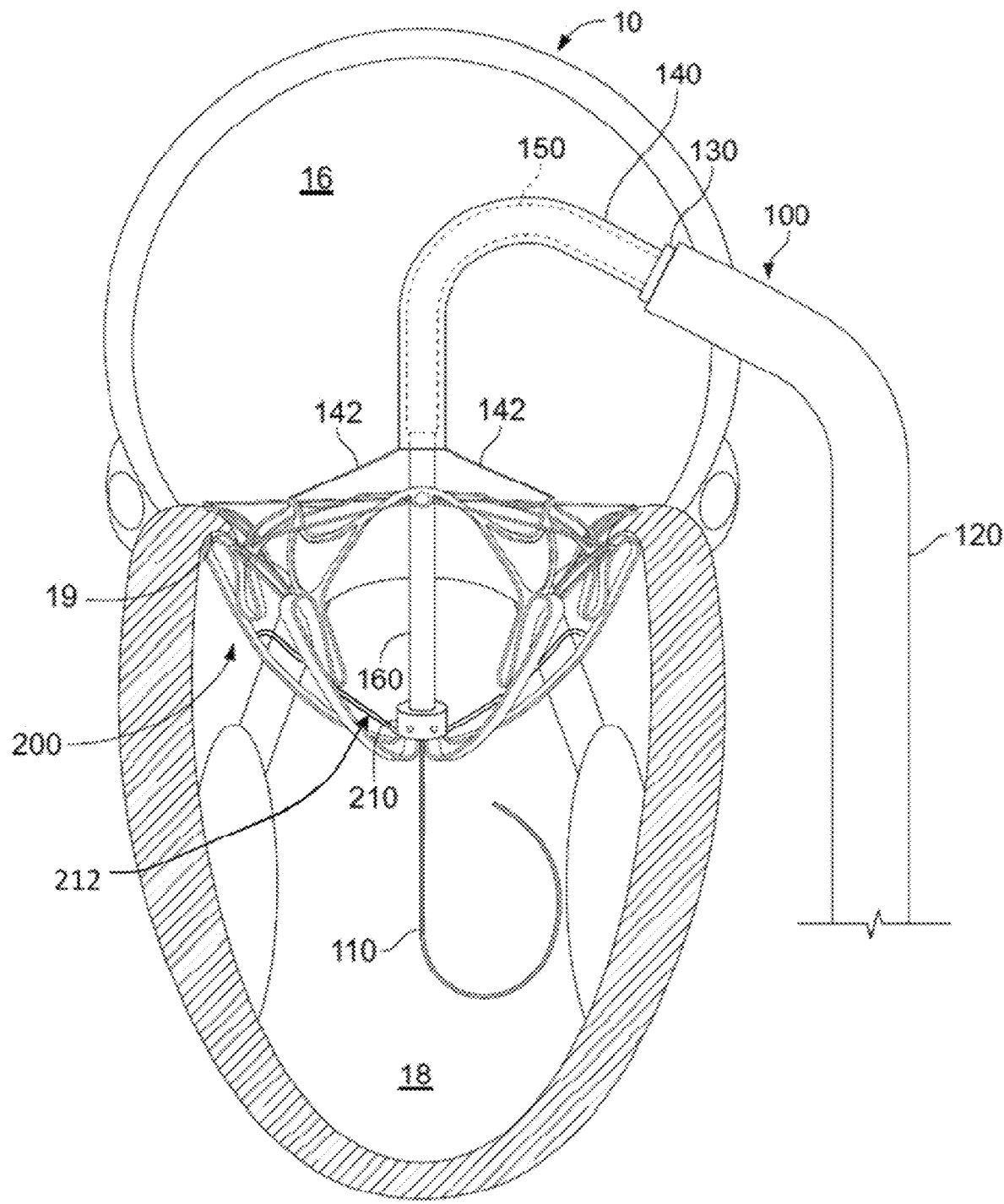
FIG. 6 shows a perspective view of the anchor assembly of FIG. 5 after being retracted so as to position the projections of the anchor assembly in the sub-annular gutter of the native mitral valve.

Referring to FIG. 6, the distal pusher 160 and the proximal control sheath 140 can be simultaneously retracted in relation to the secondary deflectable catheter 150 and the primary deflectable catheter 120. As a result, the anchor feet 220a, 220b, 220c, and 220d become seated in the sub-annular gutter 19. In this position, the anchor feet 220a, 220b, 220c, and 220d are positioned under the systolic and diastolic excursions of the leaflets of the native mitral valve 17, and the other structures of the anchor assembly 200 do not inhibit the movements of the leaflets. Therefore, with the anchor assembly 200 coupled to the structures of the mitral valve 17 as described, the mitral valve 17 can continue to function as it did before the placement of the anchor assembly 200. In addition, the manner in which the anchor assembly 200 interfaces with the native mitral valve 17 does not result in deformation of the native mitral valve 17. With the SAM containment member 212 in its pre-deployed configuration, the SAM containment member 212 does not affect the natural function of the native mitral valve 17. Therefore, the native mitral valve 17 can continue to function as it did before the placement of the anchor assembly 200.

Figure 7:
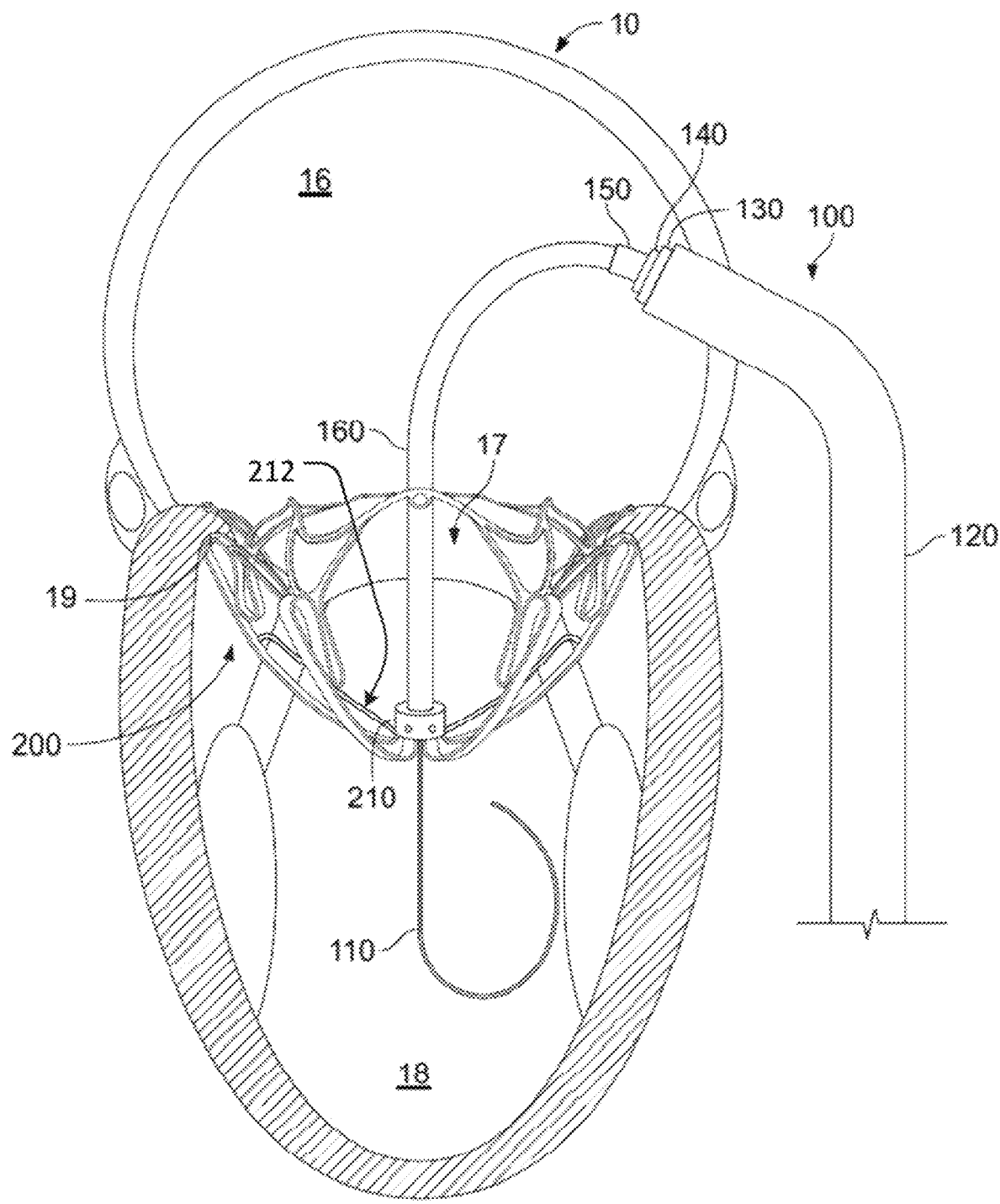
FIG. 7 shows a perspective view of the anchor assembly of FIG. 6 after the retraction of some members of the deployment system.

Referring to FIG. 7, with the anchor assembly 200 engaged within the native mitral valve 17, components of the delivery system 100 can be withdrawn from the anchor assembly 200. For example, the control wire 142 can be detached from the proximal end of the anchor assembly 200. Thereafter, the proximal control sheath 140 can be withdrawn. The secondary deflectable catheter 150 can also be withdrawn. In fact, if so desired, the proximal control sheath 140, the secondary deflectable catheter 150, and the anchor delivery sheath 130 can be completely withdrawn from the primary deflectable catheter 120. In contrast, in some implementations the distal pusher catheter 160 is advantageously left attached to the hub 210 of the anchor assembly 200 (and left attached to the SAM containment member 212 in some implementations). As will be described further below, in some implementations the distal pusher catheter 160 can be used as a rail on which a valve assembly is deployed into the interior of the anchor assembly 200. However, in some implementations the anchor assembly 200 is completely detached from the delivery system 100, and the delivery system 100 is removed from the patient. After a period of minutes, hours, days, weeks, or months, subsequent to the deployment of the anchor assembly 200, a valve assembly can be installed into the anchor assembly 200 to complete the installation of the prosthetic mitral valve.

In the depicted implementation, the SAM containment member 212 is still restrained in its pre-deployed configuration. As described further below, in some embodiments the depicted embodiment of the SAM containment member 212 is deployed after the installation of a valve assembly into the anchor assembly 200. Alternatively, as described further below, in some embodiments of the SAM containment member 212, the SAM containment member 212 is deployed prior to the installation of a valve assembly into the anchor assembly 200.

Figure 8:
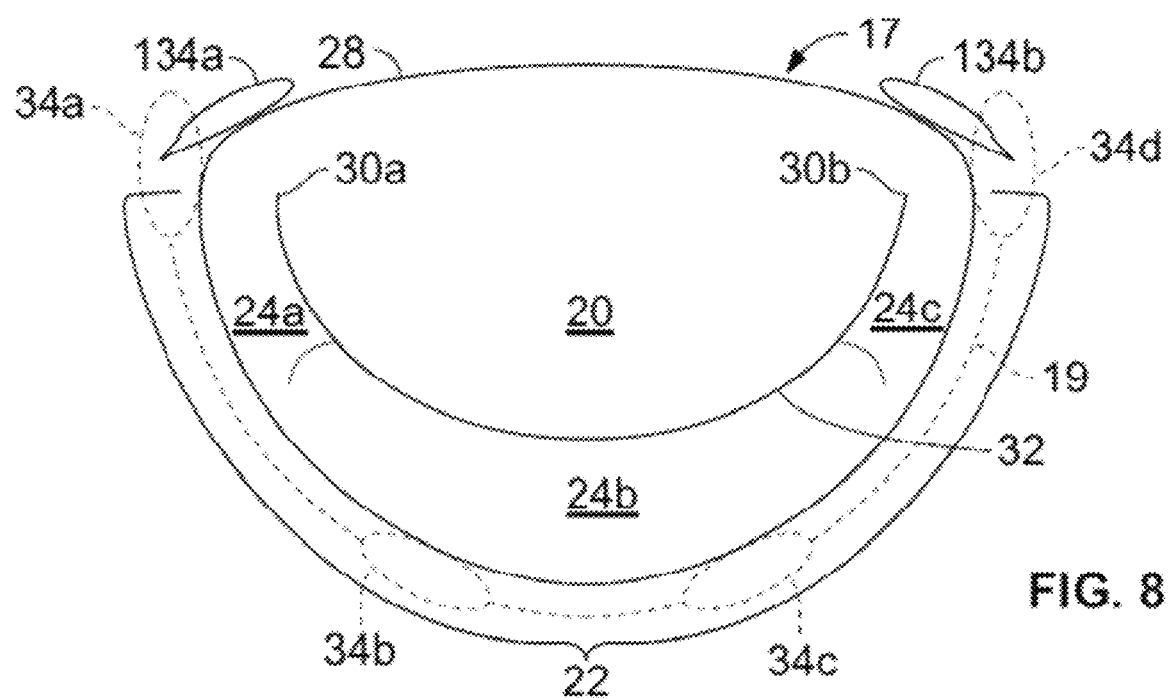
FIG. 8 is a top view of a native mitral valve and depicts a gutter perimeter of the sub-annular gutter of FIG. 7 (without the anchor assembly).

Referring to FIG. 8, the anatomy of the native mitral valve 17 includes some consistent and predictable structural features across patients that can be utilized for engaging the anchor assembly 200 therewith. For example, the native mitral valve 17 includes the aforementioned sub-annular gutter 19. In addition, the native mitral valve 17 includes a D-shaped annulus 28, an anterolateral commissure 30a, a posteromedial commissure 30b, a left fibrous trigone 134a, and a right fibrous trigone 134b. Further, the native mitral valve 17 includes an anterior leaflet 20 and a three-part posterior leaflet 22. The posterior leaflet 22 includes a lateral scallop 24a, a middle scallop 24b, and a medial scallop 24c. The free edges of the posterior leaflet 22 and the anterior leaflet 20 meet along a coaptation line 32.

The D-shaped annulus 28 defines the structure from which the anterior leaflet 20 and posterior leaflet 22 extend and articulate. The left and right fibrous trigones 134a and 134b are located near the left and right ends of the anterior leaflet 20 and generally adjacent the lateral and medial scallops 24a and 24c of the posterior leaflet 22. The sub-annular gutter 19 runs along the annulus 28 between the left and right fibrous trigones 134a and 134b along the posterior leaflet 22.

The regions at or near the high collagen annular trigones 134a and 134b can generally be relied upon to provide strong, stable anchoring locations. The muscle tissue in the regions at or near the trigones 134a and 134b also provides a good tissue ingrowth substrate for added stability and migration resistance of the anchor assembly 200. Therefore, the regions at or near the trigones 134a and 134b define a left anterior anchor zone 34a and a right anterior anchor zone 34b respectively. The left anterior anchor zone 34a and the right anterior anchor zone 34b provide advantageous target locations for placement of the lateral anterior foot 220a and the medial anterior foot 220d respectively.

Figure 9:
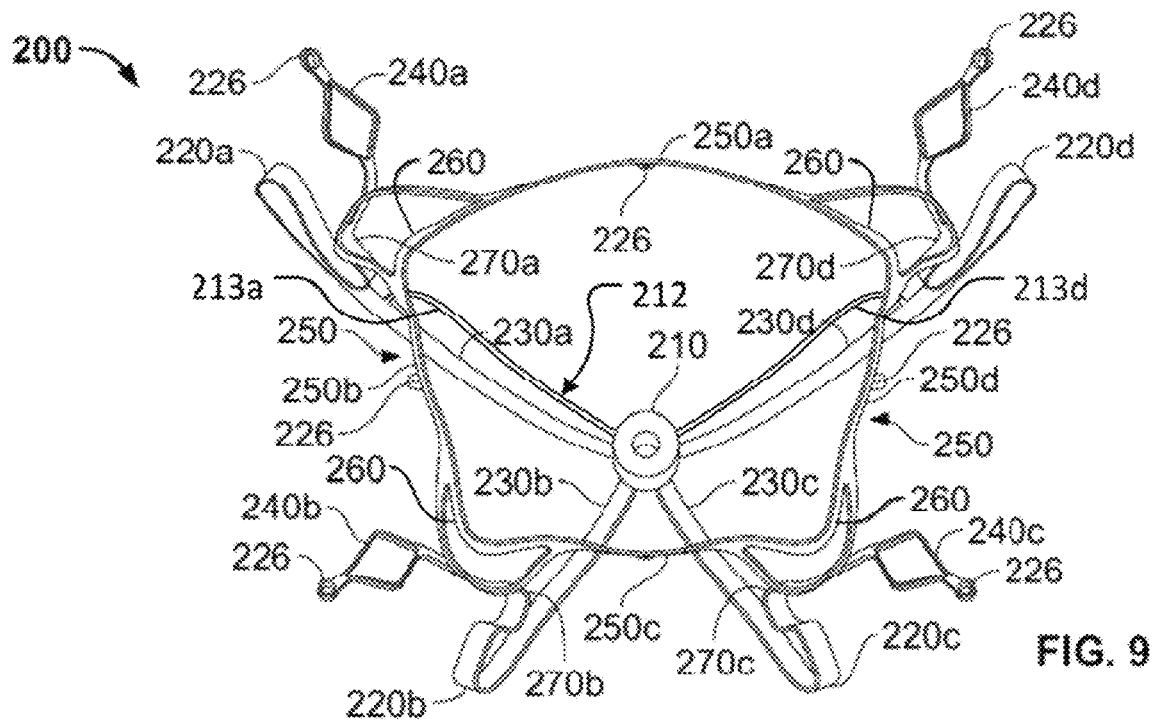
FIG. 9 shows a perspective top view of an example anchor assembly of FIGS. 2-7, including an example SAM containment member in a pre-deployed configuration, in accordance with some embodiments.

Referring also to FIG. 9, the depicted embodiment of the anchor assembly 200 also includes the lateral posterior foot 220b and the medial posterior foot 220c. As previously described, the lateral posterior foot 220b and the medial posterior foot 220c can also be advantageously positioned in the sub-annular gutter 19 in order to provide balanced and atraumatic coupling of the anchor assembly 200 to the native mitral valve 17. Therefore, a left posterior anchor zone 34b and a right anterior anchor zone 34c are defined in the sub-annular gutter 19. The left posterior anchor zone 34b and the right anterior anchor zone 34c can receive the lateral posterior foot 220b and the medial posterior foot 220c respectively. In some implementations, the locations of the left posterior anchor zone 34b and the right anterior anchor zone 34c may vary from the depicted locations while still remaining within the sub-annular gutter 19. It should be understood that the depicted anchor assembly 200 is merely one non-limiting example of the anchor assemblies provided within the scope of this disclosure.

In some embodiments, the anchor assembly 200 includes supra-annular structures and sub-annular structures. For example, the sub-annular structures of the anchor assembly 200 include the aforementioned anchor feet 220a, 220b, 220c, and 220d, the SAM containment member 212, and the hub 210. In some embodiments, as described above, the hub 210 functions as a connection structure for the delivery system 100 (e.g., refer to FIG. 2). In addition, the hub 210 can function as a stabilizing structural component from which a lateral anterior sub-annular support arm 230a, a lateral posterior sub-annular support arm 230b, a medial posterior sub-annular support arm 230c, and a medial anterior sub-annular support arm 230d extend to the anchor feet 220a, 220b, 220c, and 220d respectively.

In the depicted embodiment, the SAM containment member 212 includes a lateral anterior arm 213a and a medial anterior arm 213d. The lateral anterior arm 213a extends from the lateral anterior sub-annular support arm 230a. The medial anterior arm 213d extends from the medial anterior sub-annular support arm 230d. In some embodiments, portions of the SAM containment member 212 may extend from other areas on the anchor assembly 200.

In some embodiments, such as the depicted embodiment, the supra-annular structures of the anchor assembly 200 include: a lateral anterior atrial holding feature 240a, a lateral posterior atrial holding feature 240b, a medial posterior atrial holding feature 240c, and a medial anterior atrial holding feature 240d; an anterior anchor arch 250a, a left anchor arch 250b, a posterior anchor arch 250c, and a right anchor arch 250d; and connection bridges 260. The anterior anchor arch 250a, left anchor arch 250b, posterior anchor arch 250c, and right anchor arch 250d are joined with each other to form an undulating supra-annular ring 250 that acts as a supra-annular structural element for the anchor assembly 200. As will be described further below, the supra-annular ring 250 also defines an opening to a space within the interior of the anchor assembly 200 that is configured to receive and engage with a valve assembly. The atrial holding features 240a, 240b, 240c, and 240d are configured to contact the shelf-like supra-annular tissue surface above the mitral valve annulus, and to thereby stabilize the anchor assembly 200 in supra-annular areas that are generally opposite of the anchor feet 220a, 220b, 220c, and 220d respectively.

In some embodiments, connection bridges 260 provide enhanced stability and fatigue resistance from vertically oriented forces on a companion artificial valve assembly when the valve (not shown) is closed and blocking pressurized blood during systole. The anchor assembly 200 can also include one or more eyelets 226 in frame portions adjacent the arches, which are additional control points for delivery and retrieval of the assembly, or could be used to secure a positional delivery frame.

In some embodiments, such as the depicted embodiment, the supra-annular structures and sub-annular structures of the anchor assembly 200 are interconnected by a lateral anterior inter-annular connection 270a, a lateral posterior inter-annular connection 270b, a medial posterior inter-annular connection 270c, and a medial anterior inter-annular connection 270d. For example, the lateral anterior inter-annular connection 270a connects the lateral anterior anchor foot 220a with the lateral anterior atrial holding feature 240a. In addition, the lateral anterior inter-annular connection 270a connects the lateral anterior anchor foot 220a with the anterior anchor arch 250a and the left anchor arch 250b. In the depicted embodiment, each of the other inter-annular connections 270b, 270c, and 270d interconnect portions of the supra-annular structures and sub-annular structures in manners analogous to that of the lateral anterior inter-annular connection 270a. For example, the lateral anterior inter-annular connection 270b connects the lateral anterior anchor foot 220b with the left anchor arch 250b and the posterior anchor arch 250c; the lateral anterior inter-annular connection 270c connects the lateral anterior anchor foot 220c with the posterior anchor arch 250c and the right anchor arch 250d; and the lateral anterior inter-annular connection 270d connects the lateral anterior anchor foot 220d with the right anchor arch 250d and the anterior anchor arch 250a.

In some embodiments, the elongate members of the anchor assembly 200, including SAM containment member 212, are formed from a single piece of precursor material (e.g., sheet or tube) that is cut, expanded, and connected to the hub 210. For example, some embodiments are fabricated from a tube that is laser-cut (or machined, chemically etched, water-jet cut, etc.) and then expanded and heat-set into its final expanded size and shape. In some embodiments, the anchor assembly 200, including SAM containment member 212, is created compositely from multiple elongate members (e.g., wires or cut members) that are joined together with the hub 210 and each other to form the anchor assembly 200.

The elongate members of the anchor assembly 200 can be comprised of various materials and combinations of materials. In some embodiments, nitinol (NiTi) is used as the material of the elongate members of the anchor assembly 200, but other materials such as stainless steel, L605 steel, polymers, MP35N steel, stainless steels, titanium, colbalt/ chromium alloy, polymeric materials, Pyhnox, Elgiloy, or any other appropriate biocompatible material, and combinations thereof can be used. The super-elastic properties of NiTi make it a particularly good candidate material for the elongate members of the anchor assembly 200 because, for example, NiTi can be heat-set into a desired shape. That is, NiTi can be heat-set so that the anchor assembly 200 tends to self-expand into a desired shape when the anchor assembly 200 is unconstrained, such as when the anchor assembly 200 is deployed out from the anchor delivery sheath 130. A anchor assembly 200 made of NiTi, for example, may have a spring nature that allows the anchor assembly 200 to be elastically collapsed or "crushed" to a low-profile delivery configuration and then to reconfigure to the expanded configuration as shown in FIG. 9. The anchor assembly 200 may be generally conformable, fatigue resistant, and elastic such that the anchor assembly 200 can conform to the topography of the surrounding tissue when the anchor assembly 200 is deployed in a native mitral valve of a patient.

In some embodiments, the diameter or width/thickness of one or more of the elongate members forming the anchor assembly 200 may be within a range of about 0.008" to about 0.015" (about 0.20 mm to about 0.40 mm), or about 0.009" to about 0.030" (about 0.23 mm to about 0.76 mm), or about 0.01" to about 0.06" (about 0.25 mm to about 1.52 mm), or about 0.02" to about 0.10" (about 0.51 mm to about 2.54 mm), or about 0.06" to about 0.20" (about 1.52 mm to about 5.08 mm). In some embodiments, the elongate members forming the anchor assembly 200 may have smaller or larger diameters or widths/thicknesses. In some embodiments, each of the elongate members forming the anchor assembly 200 has essentially the same diameter or width/ thickness. In some embodiments, one or more of the elongate members forming the anchor assembly 200 has a different diameter or width/thickness than one or more of the other elongate members of the anchor assembly 200. In some embodiments, one or more portions of one or more of the elongate members forming the anchor assembly 200 may be tapered, widened, narrowed, curved, radiused, wavy, spiraled, angled, and/or otherwise non-linear and/or not consistent along the entire length of the elongate members of the anchor assembly 200. Such features and techniques can also be incorporated with the valve assemblies of the prosthetic mitral valves provided herein.

In some embodiments, the elongate members forming the anchor assembly 200 may vary in diameter, thickness and/or width so as to facilitate variations in the forces that are exerted by the anchor assembly 200 in specific regions thereof, to increase or decrease the flexibility of the anchor assembly 200 in certain regions, to enhance migration resistance, and/or to control the process of compression (crushability) in preparation for deployment and the process of expansion during deployment of the anchor assembly 200.

In some embodiments, one or more of the elongate members of the elongate members forming the anchor assembly 200 may have a circular cross-section. In some embodiments, one or more of the elongate members forming the anchor assembly 200 may have a rectangular cross-sectional shape, or another cross-sectional shape that is not rectangular. Examples of cross-sectional shapes that the elongate members forming the anchor assembly 200 may have include circular, C-shaped, square, ovular, rectangular, elliptical, triangular, D-shaped, trapezoidal, including irregular cross-sectional shapes formed by a braided or stranded construct, and the like. In some embodiments, one or more of the elongate members forming the anchor assembly 200 may be essentially flat (i.e., such that the width to thickness ratio is about 2:1, about 3:1, about 4:1, about 5:1, or greater than about 5:1). In some examples, one or more of the elongate members forming the anchor assembly 200 may be formed using a center-less grind technique, such that the diameter of the elongate members varies along the length of the elongate members.

The anchor assembly 200 may include features that are directed to enhancing one or more desirable functional performance characteristics of the prosthetic mitral valve devices. For example, some features of the anchor assembly 200 may be directed to enhancing the conformability of the prosthetic mitral valve devices. Such features may facilitate improved performance of the prosthetic mitral valve devices by allowing the devices to conform to irregular tissue topographies and/or dynamically variable tissue topographies, for example. Such conformability characteristics can be advantageous for providing effective and durable performance of the prosthetic mitral valve devices. In some embodiments of the anchor assembly 200, some portions of the anchor assembly 200 are designed to be more conformable than other portions of the same anchor assembly 200. That is, the conformability of a single anchor assembly 200 can be designed to be different at various areas of the anchor assembly 200.

In some embodiments, the anchor assembly 200 includes features for enhanced in vivo radiographic visibility. In some embodiments, portions of the anchor assembly 200, such as one or more of the anchor feet 220a, 220b, 220c, and 220d, and/or SAM containment member 212, may have one or more radiopaque markers attached thereto. In some embodiments, some or all portions of the anchor assembly 200 are coated (e.g., sputter coated) with a radiopaque coating.

Still referring to FIGS. 8 and 9, as described above the anchor feet 220a, 220b, 220c, and 220d are sized and shaped to engage the sub-annular gutter 19 of the mitral valve 17. In some embodiments, the anterior feet 220a and 220d are spaced apart from each other by a distance in a range of about 30 mm to about 45 mm, or about 20 mm to about 35 mm, or about 40 mm to about 55 mm. In some embodiments, the posterior feet 220b and 220c are spaced apart from each other by a distance in a range of about 20 mm to about 30 mm, or about 10 mm to about 25 mm, or about 25 mm to about 40 mm.

In some embodiments, the anchor feet 220a, 220b, 220c, and 220d have a height ranging from about 8 mm to about 12 mm, or more than about 12 mm. In some embodiments, the anchor feet 220a, 220b, 220c, and 220d have a gutter engaging surface area (when fabric covered) ranging from about 6 mm$^2$ to about 24 mm$^2$. In some embodiments, the anchor feet 220a, 220b, 220c, and 220d each have essentially the same gutter engaging surface area. In particular embodiments, one or more of the anchor feet 220a, 220b, 220c, and 220d has a different gutter engaging surface area than one or more of the other anchor feet 220a, 220b, 220c, and 220d. The anchor feet 220a, 220b, 220c, and 220d can have widths ranging within about 1.5 mm to about 4.0 mm or more, and lengths ranging within about 3 mm to about 6 mm or more. The anchor feet 220a, 220b, 220c, and 220d are sized and shaped so that the anchor assembly 200 does not significantly impair the natural function of mitral valve chordae tendineae, the native mitral valve leaflets, and papillary muscles even after the anchor assembly is anchored at the mitral valve site.

As described previously, the anchor assembly 200 is designed to avoid interference with the functioning of the native mitral valve 17. Therefore, the anchor assembly 200 can be implanted within the native mitral valve 17 some time prior to the deployment therein of a replacement valve assembly, without degradation of valve 17 function during the period of time between the anchor implantation and the valve implantation (whether that time is on the order of minutes, or even several days or months). To avoid such interference between the anchor assembly 200 and the native mitral valve 17, the inter-annular connections 270a, 270b, 270c, and 270d pass through the coaptation line 32 approximately. More particularly, the lateral anterior inter-annular connection 270a passes through the coaptation line 32 adjacent to the anterolateral commissure 30a. In like manner, the medial anterior inter-annular connection 270d passes through the coaptation line 32 adjacent to the posteromedial commissure 30b. In some implementations, the lateral posterior inter-annular connection 270b and medial posterior inter-annular connection 270c pass through the native mitral valve 17 in locations that are posteriorly biased from the natural coaptation line 32. The posterior leaflet 22 will tend to compliantly wrap around the lateral posterior inter-annular connection 270b and medial posterior inter-annular connection 270c to facilitate sealing of the mitral valve 17, with the anchor assembly 200 coupled thereto.

Figure 10:
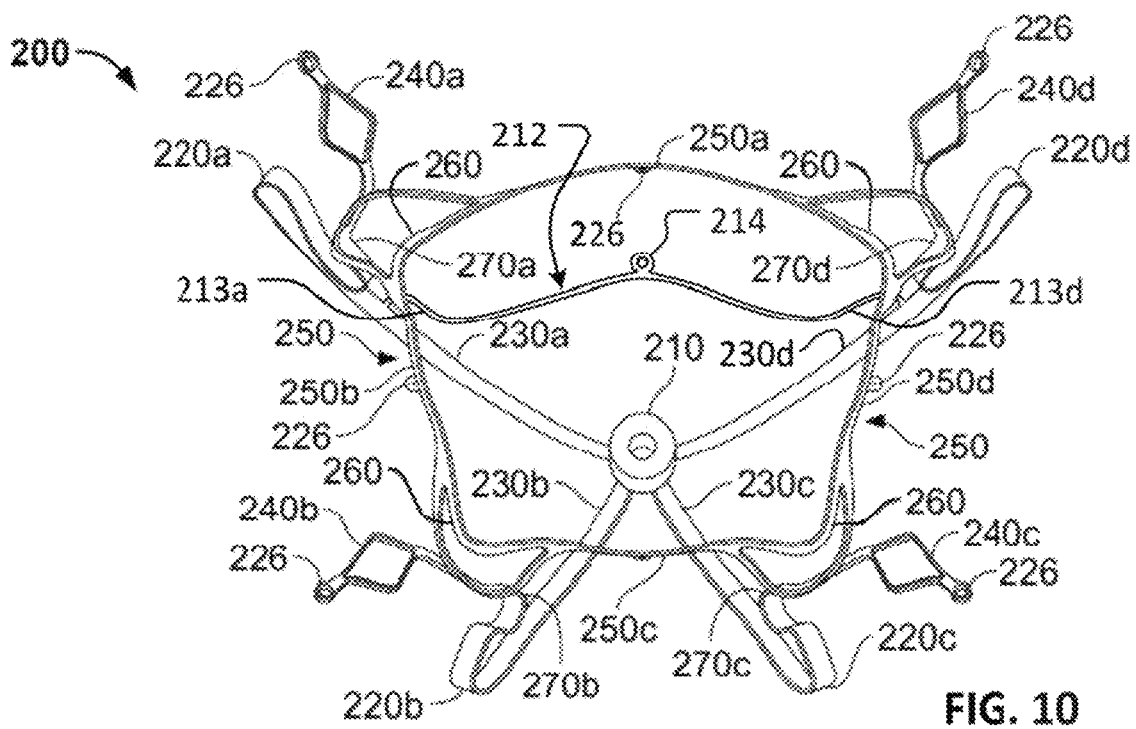
FIG. 10 shows a perspective top view of the example anchor assembly of FIG. 9, with the SAM containment member is a deployed configuration, in accordance with some embodiments.

In reference to FIGS. 9 and 10, the pre-deployed and deployed configurations of the SAM containment member 212 are illustrated respectively. The deployed configuration of the SAM containment member 212 (shown in FIG. 10) reveals that, in this embodiment, the lateral anterior arm 213a and the medial anterior arm 213d are conjoined, and that an attachment element 214 (an eyelet 214 in this embodiment) is disposed near the junction of the lateral anterior arm 213a and the medial anterior arm 213d. As described further below, the eyelet 214 provides an attachment element that can be used to control the configuration and deployment of the SAM containment member 212. In some embodiments, other types of attachment elements 214 (as alternatives to the eyelet 214) can be included on the SAM containment member 212. For example, in some embodiments one or more protrusions, ball ends, recesses, clips, breakable elements, deflectable elements, bends, and the like, and combinations thereof, can be included on the SAM containment member 212 as an attachment element 214.

In the depicted embodiment, the SAM containment member 212 is biased such that it naturally seeks to be arranged in the deployed configuration. Therefore, as described further below, in some embodiments when the SAM containment member 212 is released from being constrained in its pre-deployed configuration, the SAM containment member 212 will naturally reconfigure itself (or "self-reconfigure") into the deployed configuration (or an approximation thereof). In some embodiments, a shape-setting process is used to instill a bias so that the SAM containment member 212 tends seek its deployed configuration. Alternatively or additionally, as described further below, in some embodiments the SAM containment member 212 may be deflected into the deployed configuration by the application of one or more forces during the deployment of the SAM containment member 212.

In some implementations, while the SAM containment member 212 is deployed, the lateral anterior arm 213a and/or the medial anterior arm 213d may engage with the anterior leaflet and/or chordae to reduce the likelihood of SAM. The engagement can be anywhere along the lengths of the lateral anterior arm 213a and/or the medial anterior arm 213d, and at the juncture thereof. For example, in some implementations portions of the lateral anterior arm 213a and/or the medial anterior arm 213*d* that are near to the lateral anterior sub-annular support arm 230*a* and/or the medial anterior sub-annular support arm 230*d* can actually engage the lateral edge of the anterior leaflet and/or chordae to spread or widen the anterior leaflet at the lateral edges thereby restricting its movement and also reducing likelihood of SAM.

Figure 11:
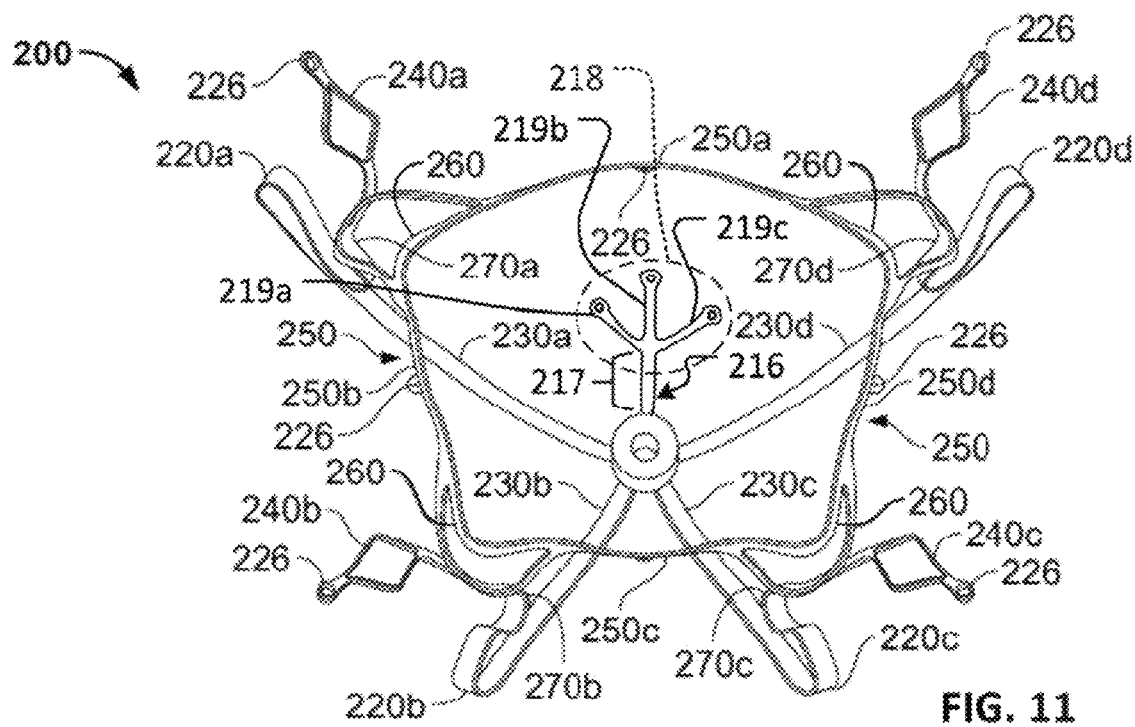
FIG. 11 shows a perspective top view of an example anchor assembly, including another example SAM containment member in a deployed configuration, in accordance with some embodiments.

In reference to FIG. 11, the anchor assembly 200 may additionally or alternately include another example embodiment of a SAM containment member 216. In the depicted embodiment, the SAM containment member 216 is fixedly attached to the hub 210, and extends in a generally anterior and superior direction from the hub 210.

The SAM containment member 216 includes an arm portion 217 attached to the hub 210, and an end portion 218 that extends from the arm portion 217. While in the depicted embodiment the arm portion 217 is a single elongate member, in some embodiments the arm portion 217 comprises two or more elongate members.

In some embodiments, as in the depicted embodiment, the end portion 218 extending from the elongate member arm portion 217 defines a width that is greater than the width of the arm portion 217. As described further below, the end portion 218 is configured to be disposed behind an anterior leaflet when the anchor assembly 200 is engaged with a native mitral valve. As used herein, "behind" an anterior leaflet refers to the aortic side of the native mitral valve leaflet when the leaflet is open.

In the depicted embodiment, the end portion 218 comprises a first elongate member 219*a*, a second elongate member 219*b*, and a third elongate member 219*c* (collectively referred to hereinafter as "three elongate members 219*a-c*"). The three elongate members 219*a-c* fan out from the arm portion 217. The three elongate members 219*a-c* thereby collectively define or encompass a broad area that will make contact with the back of the anterior leaflet of a mitral valve in situ. In some embodiments, one or more interconnecting struts may extend between the three elongate members 219*a-c*. In some embodiments, the fanned out arrangement of the three elongate members 219*a-c* is the natural or unconstrained arrangement of the three elongate members 219*a-c*. As described further below, prior to the deployment of the SAM containment member 216, the three elongate members 219*a-c* may be compressed towards each other for containment within a lumen of a low-profile delivery sheath. Upon emergence from the lumen, the three elongate members 219*a-c* may naturally diverge from each other into the fanned out arrangement as shown.

While the depicted embodiment of the end portion 218 includes three elongate members 219*a-c* that extend from the arm portion 217 in a fanned-out arrangement, various other configurations of the end portion 218 are also envisioned. For example, in some embodiments a single elongate member makes up the end portion 218. Such a single elongate member may be wider, narrower, or the same width as the arm portion 217. In some embodiments, the end portion may have two elongate members arranged in a V-shape or U-shape, and the like. In some embodiments, the end portion may include four or more elongate members. In some embodiments, the end portion may be a looped member, such as a circle, oval, triangle, rectangle, and the like. In some embodiments, the end portion 218 is generally planar. In some embodiments, the end portion 218 is contoured rather than planar. As with the three elongate members 219*a-c* described above, other configurations of the end portion 218 can be compressed for containment within a delivery sheath, and can self-expand into a larger (e.g., broader or wider) deployed configuration upon emergence from the delivery sheath.

While the three elongate members 219*a-c* of the depicted embodiment of the end portion 218 each include bulbous free ends, in some embodiments no such bulbous free ends are included. In the depicted embodiment, the bulbous free ends of the three elongate members 219*a-c* include eyelets. However, in some embodiments no such eyelets are included.

Figure 12:
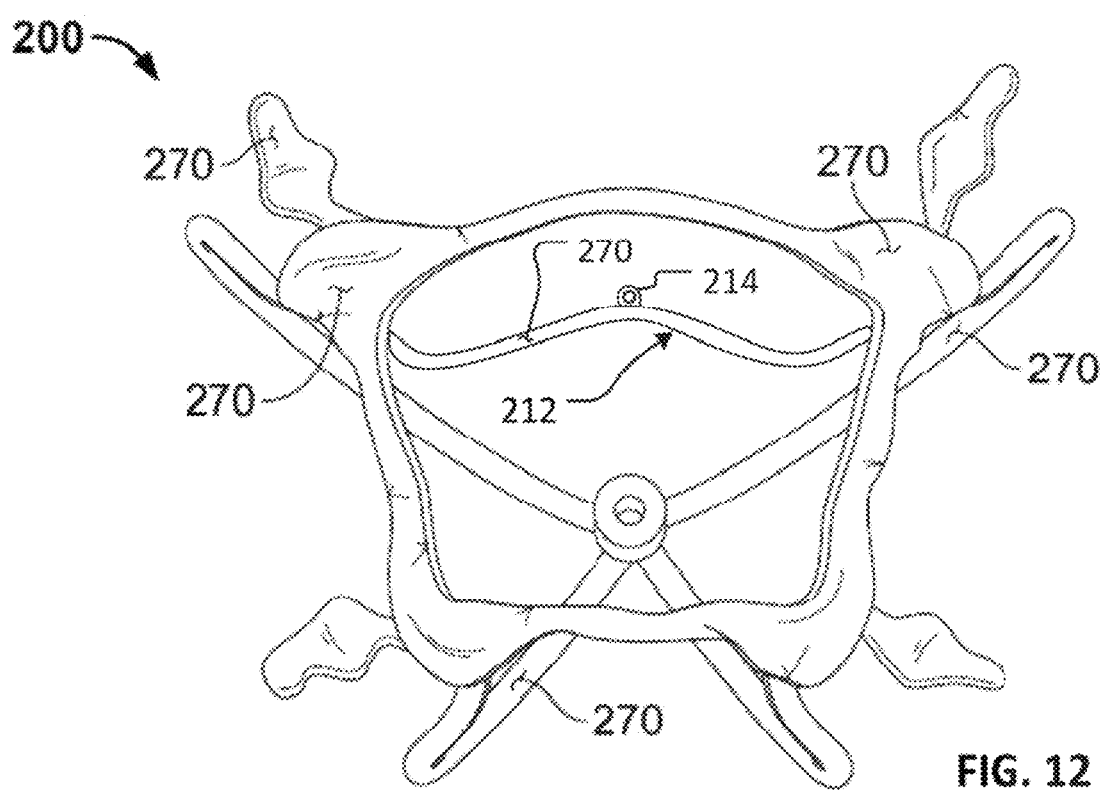
FIG. 12 shows a perspective top view of the anchor assembly of FIG. 10 with a covering material disposed on portions of the anchor frame.

In reference to FIG. 12, in some embodiments the anchor assembly 200 includes a covering material 270 disposed on one or more portions of the anchor assembly 200. The covering material 270 can provide various benefits. For example, in some implementations the covering material 270 can facilitate tissue ingrowth and/or endothelialization, thereby enhancing the migration resistance of the anchor assembly 200 and preventing thrombus formation on blood contact elements. In another example, as described further below, the covering material 270 can be used to facilitate coupling between the anchor assembly 200 and a valve assembly that is received therein. The cover material 270 also prevents or minimizes abrasion and/or fretting between the anchor assembly 200 and valve assembly 300. The cover material 270 also prevents valve outer tissue abrasion related wear, and supports to the cuff material to enhance durability. The covering material 270 may also provide redundant sealing in addition to the cuff material of the valve assembly.

In the depicted embodiment, the covering material 270 is disposed essentially on the entire anchor assembly 200, including the SAM containment member 212 (except for the eyelet 214, although in some embodiments the eyelet 214 may be essentially covered by the covering material 270). In some embodiments, the covering material 270 is disposed on one or more portions of the anchor assembly 200, while one or more other portions of the anchor assembly 200 do not have the covering material 270 disposed thereon. While the depicted embodiment includes the covering material 270, the covering material 270 is not required in all embodiments. In some embodiments, two or more portions of covering material 270, which can be separated and/or distinct from each other, can be disposed on the anchor assembly 200. That is, in some embodiments a particular type of covering material 270 is disposed on some areas of the anchor assembly 200 and a different type of covering material 270 is disposed on other areas of the anchor assembly 200.

In some embodiments, the covering material 270, or portions thereof, comprises a fluoropolymer, such as an expanded polytetrafluoroethylene (ePTFE) polymer. In some embodiments, the covering material 270, or portions thereof, comprises a polyester, a silicone, a urethane, ELAST-EON™ (a silicone and urethane polymer), another biocompatible polymer, DACRON®, polyethylene terephthalate (PET), copolymers, or combinations and subcombinations thereof. In some embodiments, the covering material 270 is manufactured using techniques such as, but not limited to, extrusion, expansion, heat-treating, sintering, knitting, braiding, weaving, chemically treating, and the like. In some embodiments, the covering material 270, or portions thereof, comprises a biological tissue. For example, in some embodiments the covering material 270 can include natural tissues such as, but not limited to, bovine, porcine, ovine, or equine pericardium. In some such embodiments, the tissues are chemically treated using glutaraldehyde, formaldehyde, or triglycidylamine (TGA) solutions, or other suitable tissue crosslinking agents.

In the depicted embodiment, the covering material 270 is disposed on the interior and the exterior of the anchor assembly 200. In some embodiments, the covering material 270 is disposed on the just the exterior of the anchor assembly 200. In some embodiments, the covering material 270 is disposed on the just the interior of the anchor assembly 200. In some embodiments, some portions of the anchor assembly 200 are covered by the covering material 270 in a different manner than other portions of the anchor assembly 200.

In some embodiments, the covering material 270 is attached to at least some portions of the anchor assembly 200 using an adhesive. In some embodiments, epoxy is used as an adhesive to attach the covering material 270 to the anchor assembly 200, or portions thereof. In some embodiments, wrapping, stitching, lashing, banding, and/or clips, and the like can be used to attach the covering material 270 to the anchor assembly 200. In some embodiments, a combination of techniques are used to attach the covering material 270 to the anchor assembly 200.

In some embodiments, the covering material 270, or portions thereof, has a microporous structure that provides a tissue ingrowth scaffold for durable sealing and/or supplemental anchoring strength of the anchor assembly 200. In some embodiments, the covering material 270 is made of a membranous material that inhibits or reduces the passage of blood through the covering material 270. In some embodiments, the covering material 270, or portions thereof, has a material composition and/or configuration that inhibits or prevents tissue ingrowth and/or endothelialization to the covering material 270.

In some embodiments, the covering material 270 can be modified by one or more chemical or physical processes that enhance certain physical properties of the covering material 270. For example, a hydrophilic coating may be applied to the covering material 270 to improve the wettability and echo translucency of the covering material 270. In some embodiments, the covering material 270 may be modified with chemical moieties that promote or inhibit one or more of endothelial cell attachment, endothelial cell migration, endothelial cell proliferation, and resistance to thrombosis. In some embodiments, the covering material 270 may be modified with covalently attached heparin or impregnated with one or more drug substances that are released in situ.

In some embodiments, covering material 270 is pre-perforated to modulate fluid flow through the covering material 270 and/or to affect the propensity for tissue ingrowth to the covering material 270. In some embodiments, the covering material 270 is treated to make the covering material 270 stiffer or to add surface texture. In some embodiments, selected portions of the covering material 270 are so treated, while other portions of the covering material 270 are not so treated. Other covering material 270 material treatment techniques can also be employed to provide beneficial mechanical properties and tissue response interactions. In some embodiments, portions of the covering material 270 have one or more radiopaque markers attached thereto to enhance in vivo radiographic visualization.

Figure 13A:
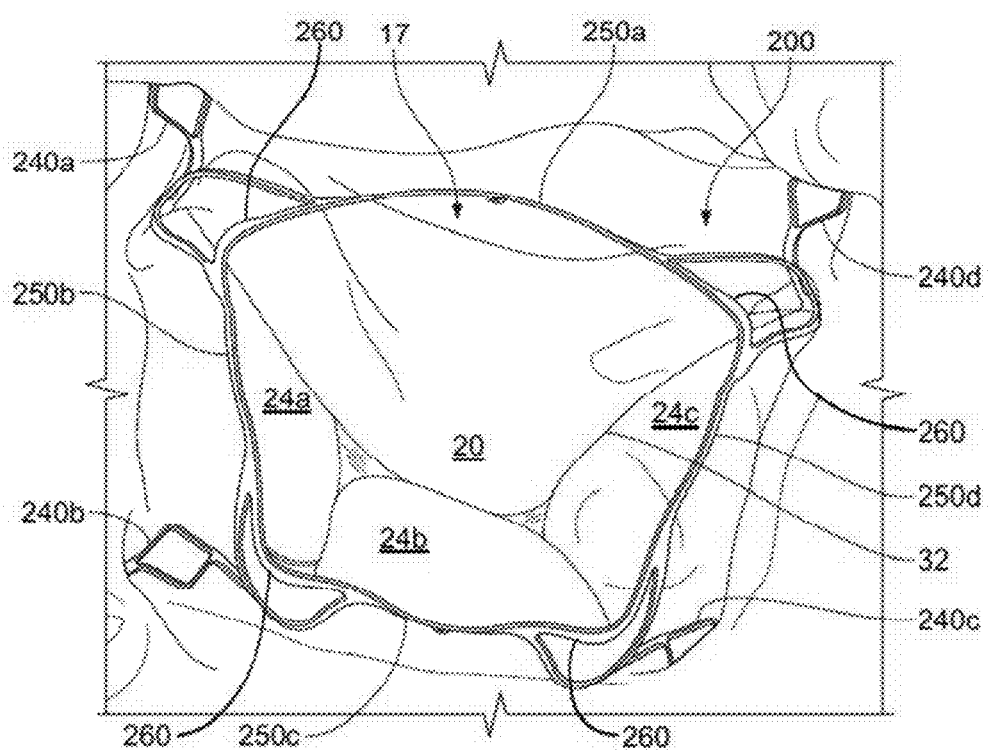
FIG. 13A shows a perspective top view of the anchor assembly of FIG. 10 implanted within a native mitral valve (with the native mitral valve leaflets in a closed state)
Figure 13B:
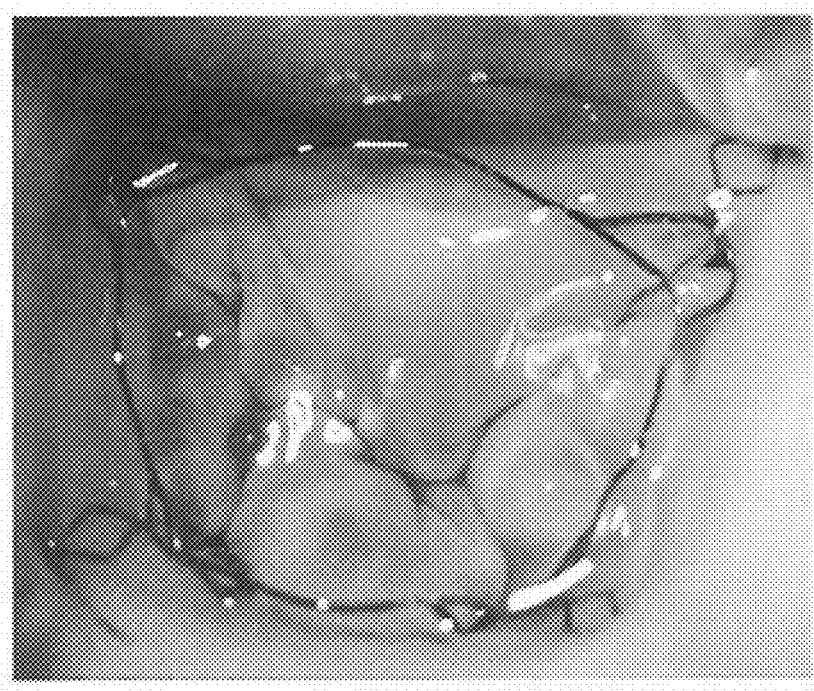
FIG. 13B shows a corresponding anatomical top view of the anchor assembly of FIG. 13A.
Figure 14A:
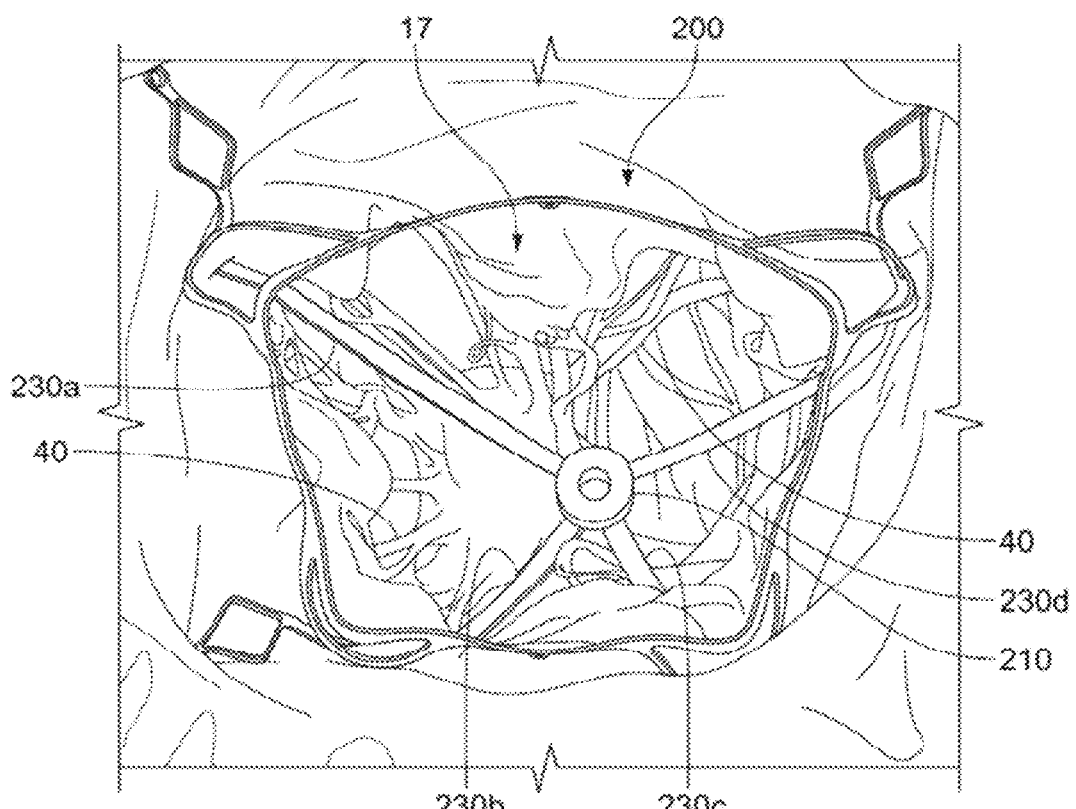
FIG. 14A shows a perspective top view of the anchor assembly of FIG. 10 implanted within the native mitral valve of FIG. 13A (with the native mitral valve leaflets in an open state)
Figure 14B:
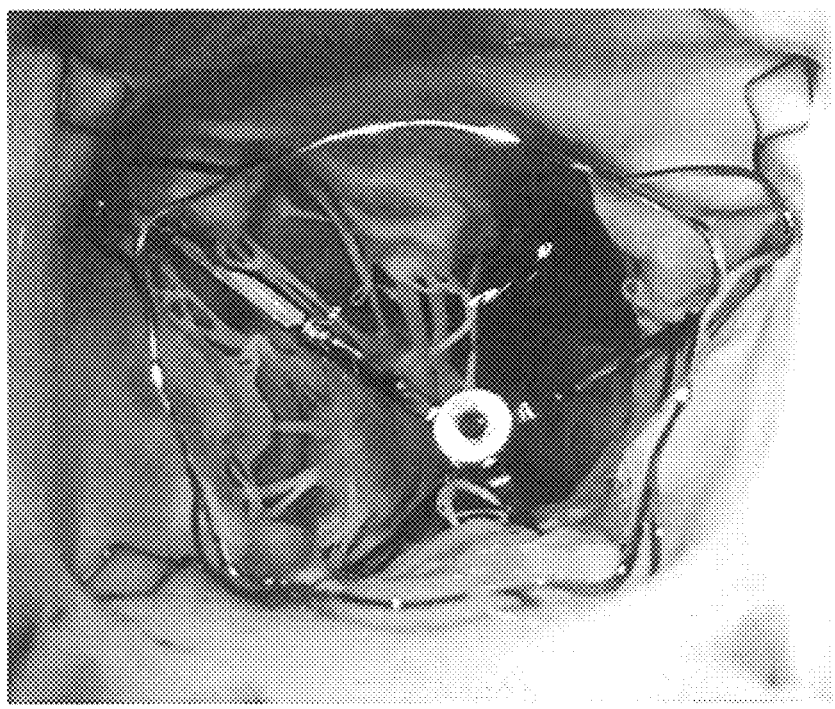
FIG. 14B shows a corresponding anatomical top view of the anchor assembly of FIG. 14A.

Referring now to FIGS. 13A and 14A, the anchor assembly 200 is shown implanted within a native mitral valve 17. FIGS. 13B and 14B are photographs that correspond to FIGS. 13A and 14A respectively. In FIG. 13A, the mitral valve 17 is shown in a closed state. In FIG. 14A, the mitral valve 17 is shown in an open state. These illustrations are from the perspective of the left atrium looking towards the mitral valve 17. For instance, in FIG. 14A chordae tendineae 40 are visible through the open leaflets of the mitral valve 17.

These figures illustrate the supra-annular structures and sub-annular structures of the anchor assembly 200 in their relationships with the native mitral valve 17. For example, the closed state of the native mitral valve 17 in FIG. 13A allows visibility of the supra-annular structures such as the lateral anterior atrial holding feature 240a, the lateral posterior atrial holding feature 240b, the medial posterior atrial holding feature 240c, and the medial anterior atrial holding feature 240d. In addition, the anterior anchor arch 250a, the left anchor arch 250b, the posterior anchor arch 250c, the right anchor arch 250d, and the connection bridges 260 are visible. However, the sub-annular structures are not visible in FIG. 13A because such structures are obstructed from view by the anterior leaflet 20 and the three-part posterior leaflet 24a, 24b, and 24c.

In contrast, in FIG. 14A certain sub-annular structures of the anchor assembly 200 are visible because the native mitral valve 17 is open. For example, sub-annular support arms 230a, 230b, 230c, and 230d and hub 210 are in view through the open mitral valve 17. Nevertheless, the anchor feet 220a, 220b, 220c, and 220d remain out of view because of their location within the sub-annular gutter of the mitral valve 17. In addition, no SAM containment member (which is a sub-annular structure) is visible in this view.

Figure 15:
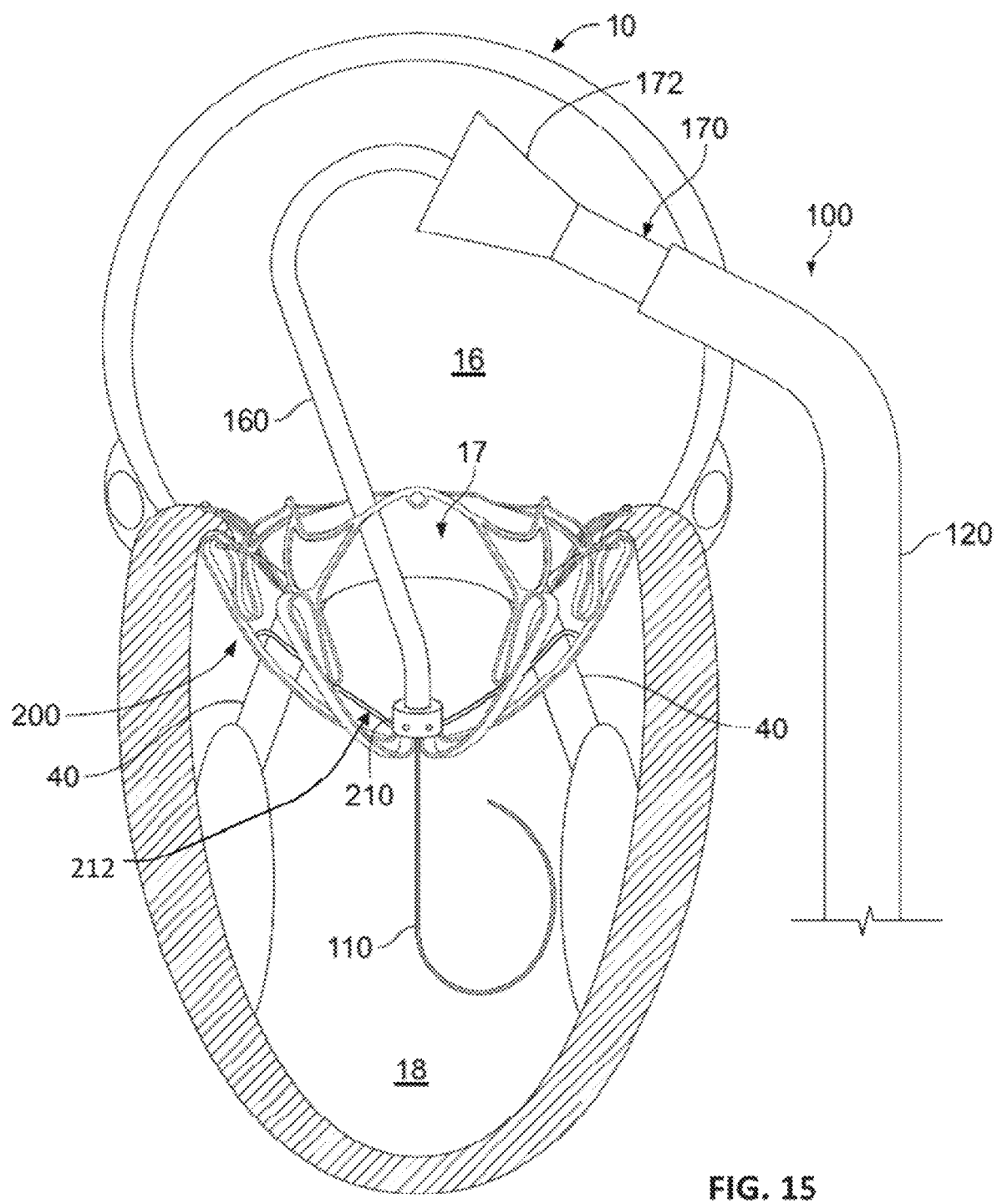
FIG. 15 shows a perspective view of the anchor assembly of FIG. 7 implanted within the native mitral valve and a valve assembly delivery sheath extending into the left atrium.

Referring to FIG. 15, after implantation of the anchor assembly 200 within the native mitral valve 17 (as performed, for example, in accordance with FIGS. 1-7 described above), a valve delivery sheath 170 of the delivery system 100 can be used to deploy a valve assembly within the anchor assembly 200. As described above in reference to FIG. 7, with the distal pusher catheter 160 coupled with the hub 210 of the anchor assembly 200, the distal pusher catheter 160 can be used to guide the valve assembly into the interior of the anchor assembly 200.

In the depicted embodiment, the SAM containment member 212 is constrained in its pre-deployed configuration. However, in some other SAM containment member embodiments (e.g., as described further below in reference to FIGS. 27-33), the SAM containment member may be deployed prior to installation of a valve assembly within the anchor assembly 200. Generally speaking, depending on the SAM containment member embodiment's design, if the SAM containment member may potentially interfere with the function of the anterior leaflet, it may be preferable to wait until the valve is implanted to deploy the SAM containment member. But, if the SAM containment member does not or is unlikely to interfere with the leaflet function, the SAM containment member may be deployed prior to valve implant (which may be beneficial for situations where the anchor is implanted in a separate procedure from the valve implantation).

In some implementations, with the primary deflectable catheter 120 positioned with its distal end in the left atrium 16, the valve delivery sheath 170 is installed into a lumen of the primary deflectable catheter 120 (over the distal pusher catheter 160) and advanced through the primary deflectable catheter 120. As described further below, in some embodiments the valve delivery sheath 170 is preloaded with a prosthetic valve assembly and other components of the delivery system 100. The primary deflectable catheter 120 may be the same catheter that was used to deliver the anchor assembly 200, or it may be a different catheter (but still referred to here as the primary deflectable catheter 120 for simplicity sake).

In some embodiments, the valve delivery sheath 170 can be made from the materials described above in reference to the primary deflectable catheter 120. In some embodiments, the valve delivery sheath 170 has an outer diameter in the range of about 20 Fr to about 28 Fr (about 6.7 mm to about 9.3 mm). In some embodiments, the valve delivery sheath 170 has an outer diameter in the range of about 14 Fr to about 24 Fr (about 4.7 mm to about 8.0 mm).

In the depicted embodiment, the valve delivery sheath 170 includes a flared distal end portion 172. In some embodiments, no such flared distal end portion 172 is included. The flared distal end portion 172 can collapse to a lower profile when constrained within the primary deflectable catheter 120. When the flared distal end portion 172 is expressed from the primary deflectable catheter 120, the flared distal end portion 172 can self-expand to the flared shape. In some embodiments, the material of the flared distal end portion 172 includes pleats or folds, may be a continuous flared end or may be separated into sections such as flower pedals, and may include one or more resilient elements that bias the flared distal end portion 172 to assume the flared configuration in the absence of restraining forces (such as from containment within the primary deflectable catheter 120). The flared distal end portion 172 can be advantageous, for example, for recapturing the valve assembly within the lumen of the valve delivery sheath 170 after the valve assembly has been expressed from the flared distal end portion 172.

In some embodiments, the maximum outer diameter of the flared distal end portion 172 is in a range of about 30 Fr to about 34 Fr (about 10.0 mm to about 11.3 mm). In some embodiments, the maximum outer diameter of the flared distal end portion 172 is in a range of about 32 Fr to about 44 Fr (about 10.7 mm to about 14.7 mm). In some embodiments, the maximum outer diameter of the flared distal end portion 172 is in a range of about 24 Fr to about 30 Fr (about 8.0 mm to about 10.0 mm). In some embodiments, the maximum outer diameter of the flared distal end portion 172 is less than about 24 Fr (about 8.0 mm) or greater than about 44 Fr (about 14.7 mm).

Figure 16:
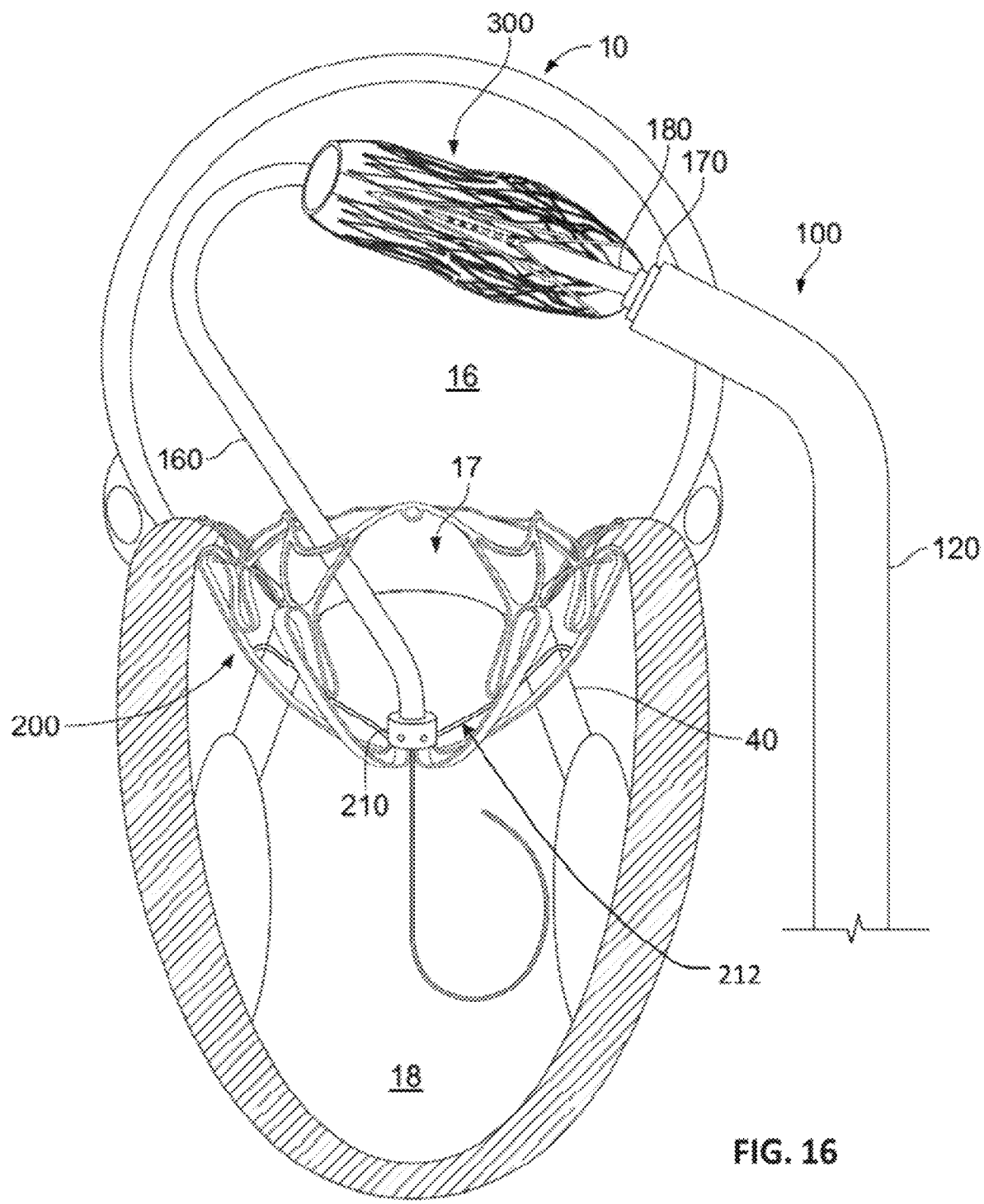
FIG. 16 shows a perspective view of a valve assembly in the left atrium after partial emergence from the valve assembly delivery sheath of FIG. 15. The valve assembly is configured in a first (partially expanded) arrangement.

Referring to FIG. 16, in some implementations the valve delivery sheath 170 can be withdrawn into the primary deflectable catheter 120 while a valve delivery catheter 180 is held substantially stationary to express a valve assembly 300 from a lumen of the valve delivery sheath 170. The valve delivery sheath 170 and the valve delivery catheter 180 are additional components in some embodiments of the example delivery system 100.

The valve assembly 300 can be releasably coupled to the valve delivery catheter 180 and retained in a low-profile configuration. In some embodiments, both the distal and proximal ends of the valve assembly 300 are releasably coupled to the valve delivery catheter 180. In some embodiments, just one of the distal end or the proximal end of the valve assembly 300 is releasably coupled to the valve delivery catheter 180. In particular embodiments, one or more control wires may be included to releasably couple one or more portions of the valve assembly 300 to the valve delivery catheter 180.

Figure 17:
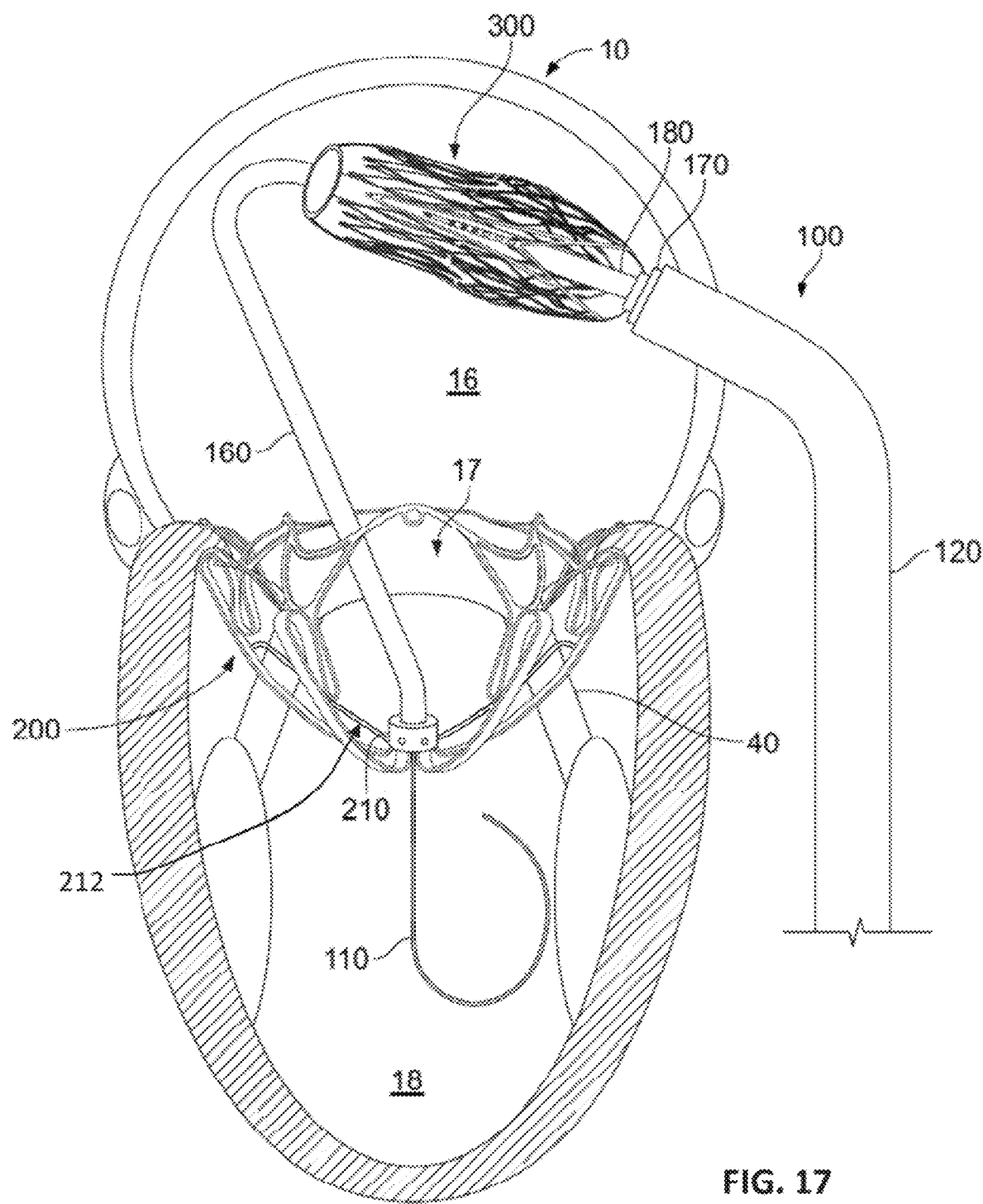
FIG. 17 shows a perspective view of the valve assembly of FIG. 16 with the valve deployment system being manipulated in preparation for the installation of the valve assembly into the anchor assembly.
Figure 18:
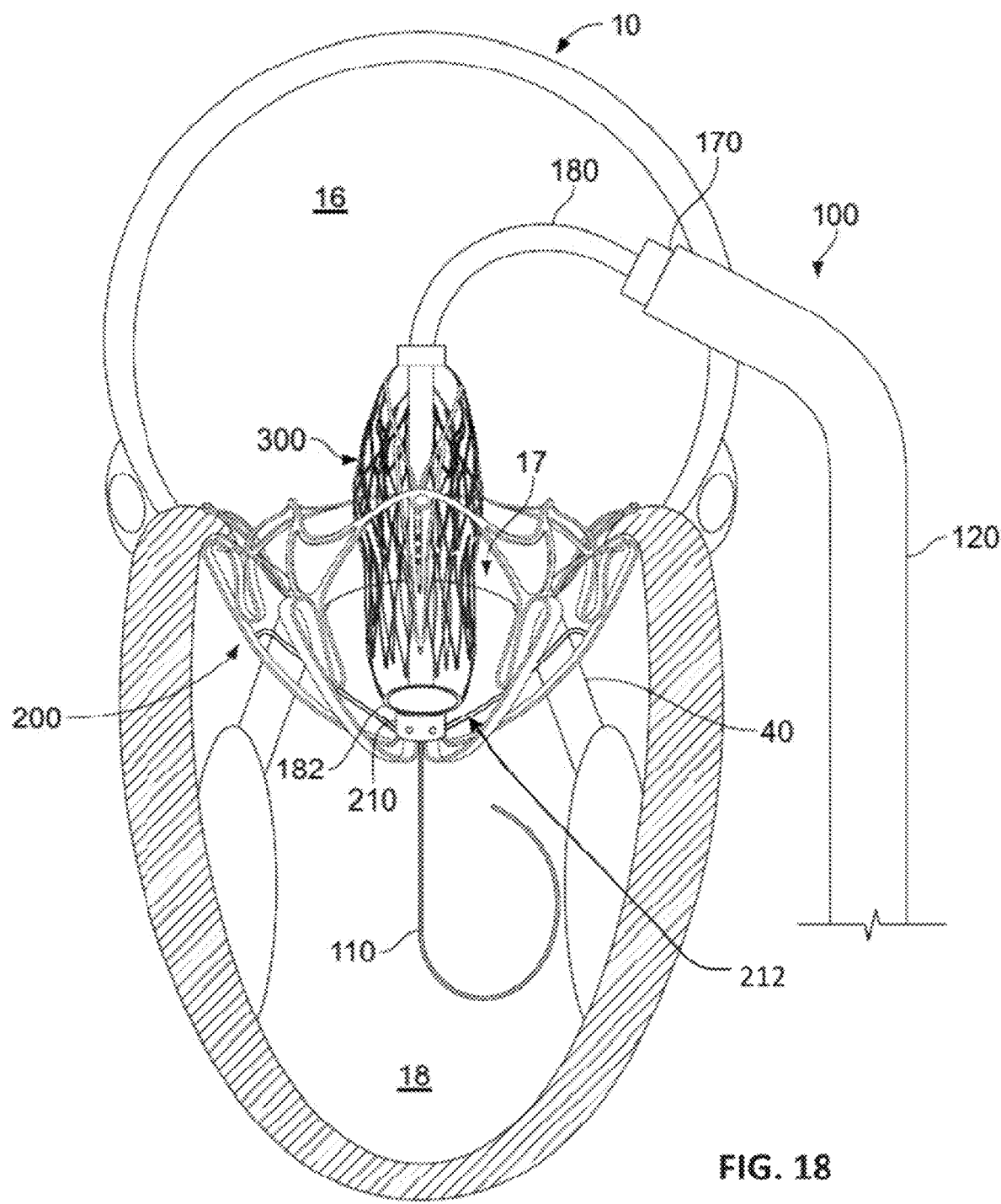
FIG. 18 shows a perspective view of the valve assembly of FIG. 17 (while still in the first (partially expanded) arrangement) being positioned within the anchor assembly.

Referring to FIGS. 17 and 18, the delivery system 100 can be manipulated by a clinician operator to perform a lateral pivot (panning, rotation, etc.) of the valve assembly 300 within the left atrium 16. The rotation of the valve assembly 300 changes the alignment of the valve assembly 300 from being generally axial with the distal end portion of the primary deflectable catheter 120 to being generally axial with the anchor assembly 200 (in preparation for installation of the valve assembly 300 into the interior of the anchor assembly 200).

In some implementations, the aforementioned rotation of the valve assembly 300 can be performed as follows. As shown in FIG. 17, because of the influence from the primary deflectable catheter 120 on the valve delivery catheter 180, the axis of the valve assembly 300 is initially in general alignment with the axis of the distal end portion of the primary deflectable catheter 120. From this arrangement, a simultaneous counter movement between the distal pusher catheter 160 and the valve delivery catheter 180 can be performed by the clinician to rotate the valve assembly 300. That is, as the distal pusher catheter 160 is pulled proximally, the valve delivery catheter 180 is pushed distally. As a result of that counter movement, the valve assembly 300 rotates in a relatively tight radius, as required by the confines of the left atrium 16. Thereafter, the valve delivery catheter 180 can be advanced further so that the valve assembly 300 is coaxially positioned within the interior of the anchor assembly 200 as shown in FIG. 18.

Figure 19:
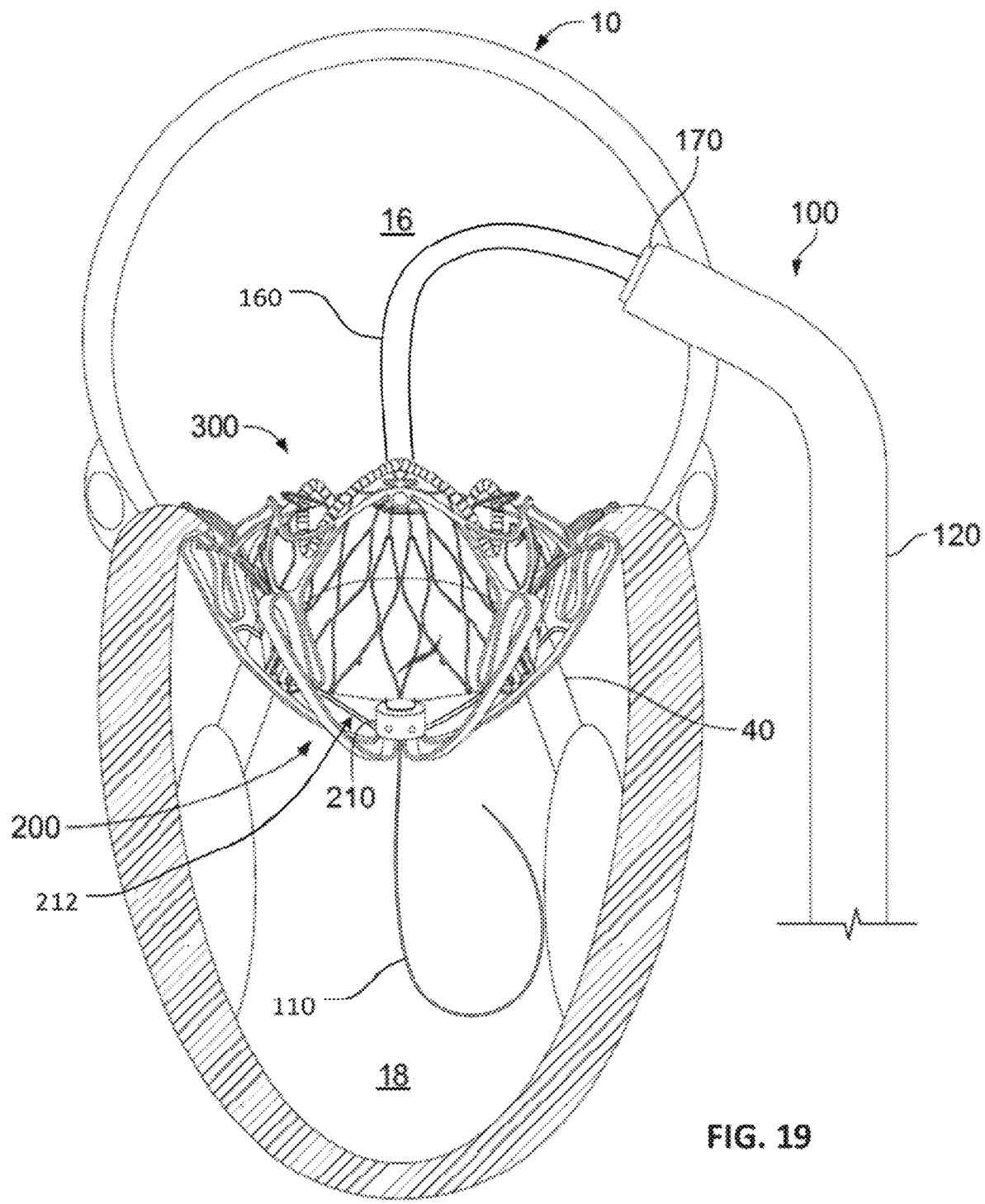
FIG. 19 shows a perspective view of the valve assembly of FIG. 18, with the valve assembly expanded within the anchor assembly and detached from the deployment system, but prior to deployment of the SAM containment member.

Referring now also to FIG. 19, in some embodiments the valve assembly 300 and the anchor assembly 200 become aligned with each other coaxially, linearly (along their axes), and rotationally prior to or during the expansion of the valve assembly 300, resulting in engagement between the valve assembly 300 and the anchor assembly 200.

Coaxial alignment between the valve assembly 300 and the anchor assembly 200, as described above, is achieved by virtue of the valve delivery catheter 180 being slidably disposed over the distal pusher catheter 160. Linear alignment between the valve assembly 300 and the anchor assembly 200 can be achieved by the interaction of a distal end feature 182 of the valve delivery catheter 180 and the hub 210 of the anchor assembly 200. For example, in some embodiments an abutting of the distal end feature 182 and the hub 210 can result in proper linear alignment between the valve assembly 300 and the anchor assembly 200.

Relative rotational alignment between the valve assembly 300 and the anchor assembly 200 (about their axes) can be achieved in various manners. For example, in some embodiments the valve delivery catheter 180 is mechanically keyed to the distal pusher catheter 160 to slidably fix a desired rotational alignment between the valve assembly 300 and the anchor assembly 200. In some embodiments, other types of mechanical features (e.g., pins/holes, protrusions/receptacles, etc.) can be included to facilitate a desired rotational/spin alignment between the valve assembly 300 and the anchor assembly 200. Alternatively, or additionally, radiopaque markers can be included on the valve assembly 300 and on the anchor assembly 200 (including on the SAM containment member) in locations and/or patterns that are indicative of the relative rotational orientation (about their axes) of the valve assembly 300 and the anchor assembly 200. In some embodiments, (e.g., when the valve delivery catheter 180 "torqueable") the valve delivery catheter 180 can be rotated about its axis until the markers are in proper position relative to the anchor assembly 200, prior to final expansion of valve assembly 300. Fluoroscopy can be used to attain a desired relative orientation of the radiopaque markers, and of the valve assembly 300 and the anchor assembly 200 (including on the SAM containment member) correspondingly.

In the depicted implementation, the SAM containment member 212 is still in its pre-deployed configuration. Therefore, the depicted embodiment of the SAM containment member 212 is deployed after the valve assembly 300 is engaged within the anchor assembly 200. However, for some alternative embodiments of the SAM containment member (as described further below) the SAM containment member is deployed prior to the engagement of the valve assembly 300 within the anchor assembly 200.

Figure 20:
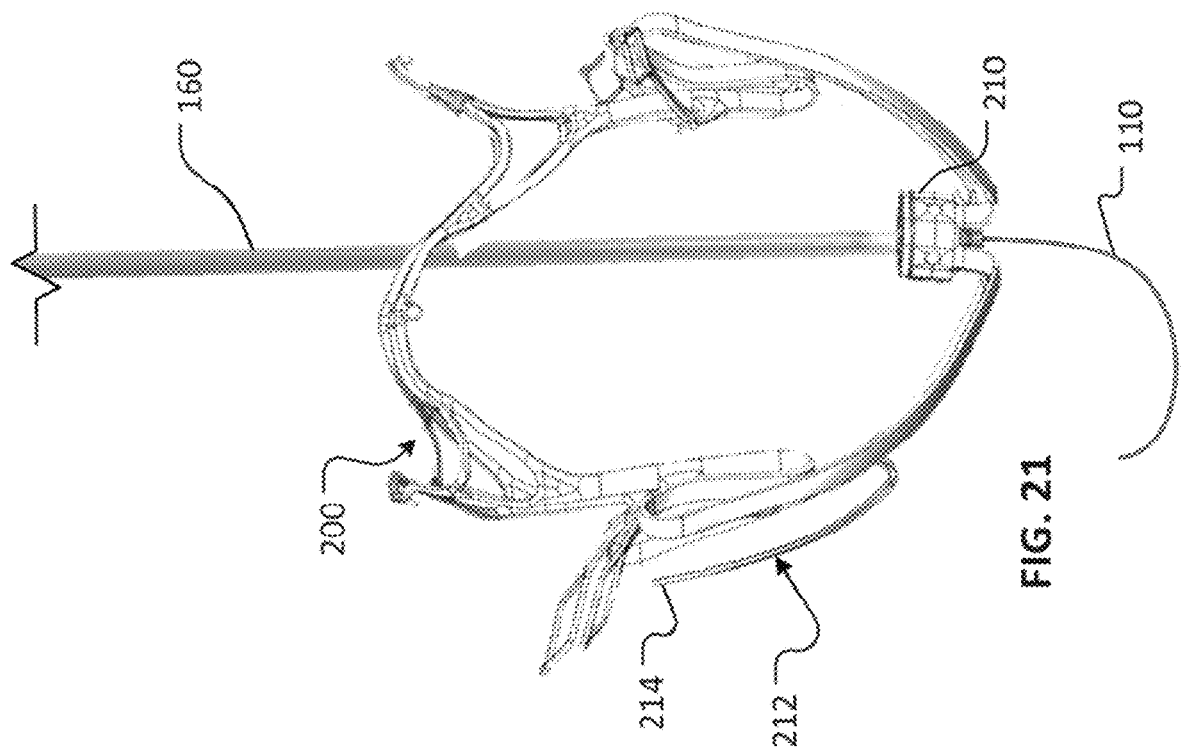
FIG. 20 shows a side view of the anchor assembly of FIG. 9 with a SAM containment member coupled with an example deployment system in a pre-deployed configuration, in accordance with some embodiments.
Figure 21:
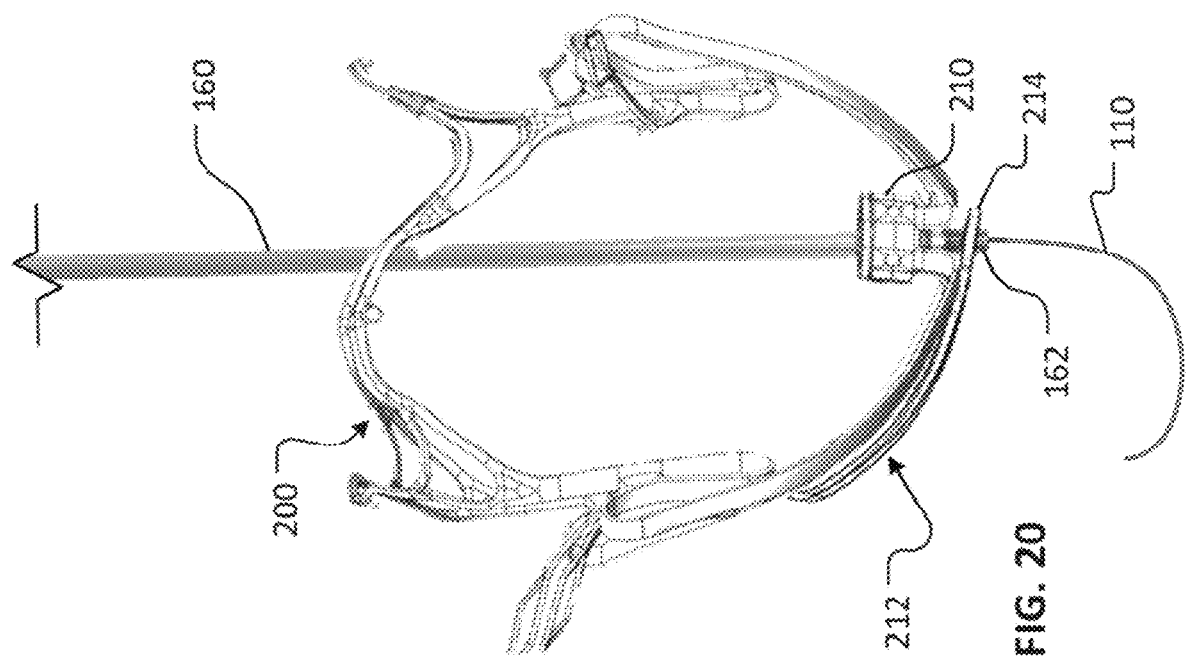
FIG. 21 shows the anchor assembly of FIG. 20 with the SAM containment member in a deployed configuration, in accordance with some embodiments.

Referring to FIGS. 20 and 21, the SAM containment member 212 of the anchor assembly 200 can be configured in a pre-deployed configuration and a deployed configuration. FIG. 20 shows the SAM containment member 212 in the pre-deployed configuration, and FIG. 21 shows the SAM containment member 212 in the deployed configuration. As described further below, in some embodiments the deployment of the SAM containment member 212 takes place after the anchor assembly 200 and after the valve assembly 300 are installed in the native mitral valve (as described above in reference to FIGS. 1-19). Here, for simplicity, the valve assembly 300 is not shown. This technique for deploying the SAM containment member 212 results in the positioning of the SAM containment member 212 anteriorly to (also referred to herein as "behind") the native mitral valve anterior leaflet. Accordingly, the deployed SAM containment member 212 acts as a physical barrier that inhibits and/or prevents the native mitral valve anterior leaflet from obstructing the LVOT.

It is envisioned that the deployment of the SAM containment member 212 can be performed in a controlled manner by the use of various mechanisms and techniques that are all within the scope of this disclosure. Multiple non-limiting examples of such SAM containment and deployment mechanisms and techniques are provided herein.

As described above, in some embodiments the transcatheter mitral valve delivery system 100 includes the distal pusher catheter 160 and the guidewire 110. In some embodiments, the guidewire 110 is slidably disposed within a lumen of the distal pusher catheter 160, and the guidewire 110 can extend distally out from the distal end of the distal pusher catheter 160. As in the depicted embodiment, in some embodiments the guidewire 120 can extend through the eyelet 214 of the SAM containment member 212.

In the example embodiment depicted in FIGS. 20 and 21, the distal pusher catheter 160 includes a threaded distal end 162 out of which the guidewire 110 can distally extend. As depicted, in some embodiments the threaded distal end 162 can be mated with complementary internal threads within the eyelet 214 of the SAM containment member 212. Accordingly, the threaded distal end 162 can be selectively threaded into engagement with the eyelet 214, and selectively unthreaded from engagement with the eyelet 214. Said another way, in some embodiments the distal pusher catheter 160 is releasably engageable with the SAM containment member 212. A clinician that is performing the process of deploying the anchor assembly 200 can thereby control the deployment of the SAM containment member 212. In other words, by turning the distal pusher catheter 160 the clinician can unthread the threaded distal end 162 from the eyelet 214 to release or deploy the SAM containment member 212.

When the threaded distal end 162 is coupled with the eyelet 214, the SAM containment member 212 is restrained in its pre-deployed configuration (FIG. 20). When the threaded distal end 162 is uncoupled from the eyelet 214, the SAM containment member 212 is released from constraint by the distal pusher catheter 160, and the SAM containment member 212 is then free to seek its natural deployed configuration (FIG. 21).

In some implementations, while the SAM containment member 212 is deployed, portions of the SAM containment member 212 may engage with the anterior leaflet and/or chordae to reduce the likelihood of SAM. The engagement can be anywhere along the lengths of the lateral anterior arm 213a and/or the medial anterior arm 213d, and at the juncture thereof (e.g., refer to FIG. 10). For example, in some implementations portions of the lateral anterior arm 213a and/or the medial anterior arm 213d that are near to the lateral anterior sub-annular support arm 230a and/or the medial anterior sub-annular support arm 230d can actually engage the lateral edge of the anterior leaflet and/or chordae to spread or widen the anterior leaflet at the lateral edges, thereby restricting its movement and also reducing likelihood of SAM.

Figure 23:
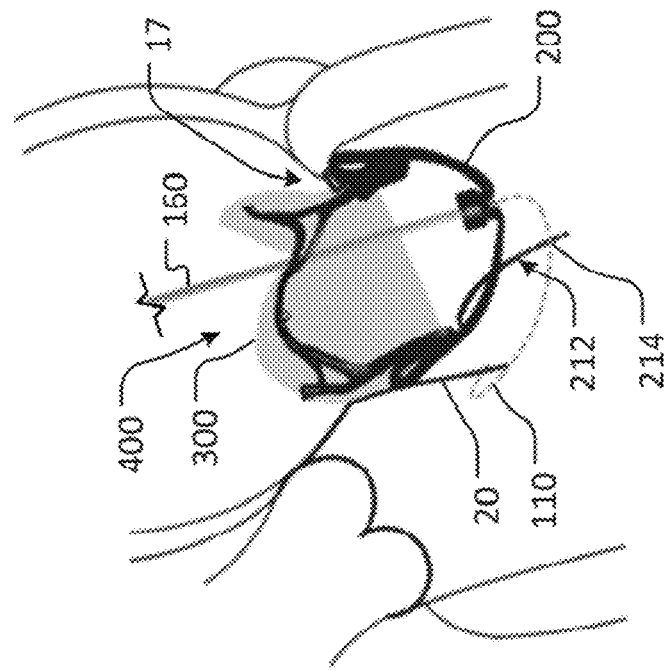
FIG. 23 shows another schematic side view of the native mitral valve coupled with the anchor assembly as in FIG. 22, and the deployment system of FIG. 20, with the SAM containment member in a second partially-deployed configuration, in accordance with some embodiments.
Figure 22:
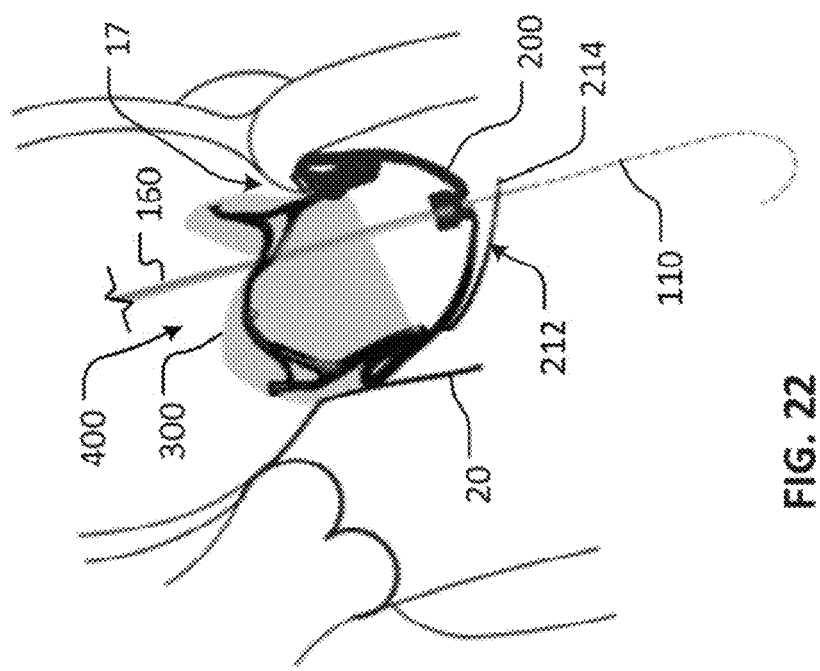
FIG. 22 shows a schematic side view of a native mitral valve coupled with the anchor assembly of FIG. 9, and the deployment system of FIG. 20, with the SAM containment member in a first partially-deployed configuration, in accordance with some embodiments.
Figure 24:
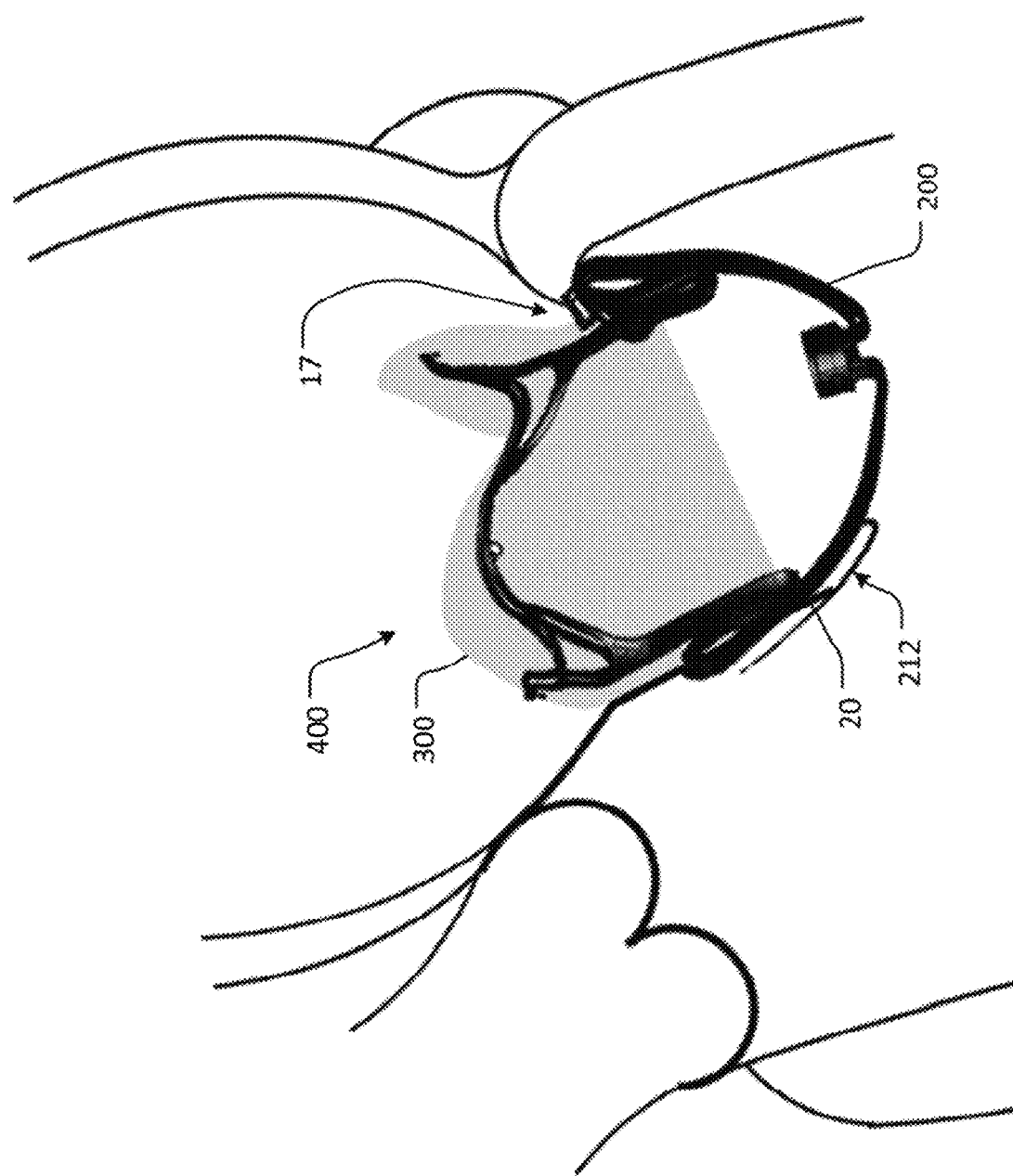
FIG. 24 shows another schematic side view of the native mitral valve coupled with the anchor assembly as in FIGS. 22 and 23, with the SAM containment member in a deployed configuration, in accordance with some embodiments.

Referring to FIGS. 22-24, the deployment process of the SAM containment member 212, while the prosthetic mitral valve 400 is engaged with the native mitral valve 17 (as described above), will now be described further. FIG. 22 shows the position of the SAM containment member 212 after detachment from the distal pusher catheter 160 but prior to substantial movement of the SAM containment member 212 from its constrained pre-deployed configuration. FIG. 23 depicts the interim position of the SAM containment member 212 as it is moving to (or self-deflecting to) its natural deployed configuration. FIG. 24 shows the position of the SAM containment member 212 in its deployed configuration where the SAM containment member 212 is at least partially disposed behind anterior leaflet 20 (i.e., on the aortic side of anterior leaflet 20). Therefore, this series of figures depicts the deployment process (or "self-reconfiguring" process) of the SAM containment member 212 post-decoupling from the distal pusher catheter 160.

These figures include depictions of the prosthetic mitral valve 400 (including the anchor assembly 200 that is coupled or mated with the valve assembly 300), the distal pusher catheter 160 and the guidewire 110 (which are component members of a delivery system), the native mitral valve 17 of a patient, and the anterior leaflet 20 of the native mitral valve 17. It should be noted that in this implementation, the deployment of the SAM containment member 212 is taking place after the prosthetic mitral valve 400 (including the anchor assembly 200 coupled or mated with the valve assembly 300) is engaged in an operative position with the native mitral valve 17. Alternatively, in some implementations the deployment of the SAM containment member 212 can take place after the engagement of the anchor assembly 200 with the native mitral valve 17, but prior to the coupling/mating of the valve assembly 300 with the anchor assembly 200.

In some embodiments, the guidewire 110 is engaged with an attachment element of the SAM containment member 212. For example, in the depicted embodiment the guidewire 110 is threaded through the eyelet 214 of the SAM containment member 212. Accordingly, after detachment of the distal pusher catheter 160 from the SAM containment member 212, the guidewire 110 remains slidably engaged with the SAM containment member 212.

In some implementations, the fact that the guidewire 110 can remain engaged with the SAM containment member 212 after detachment from the distal pusher catheter 160 enables the guidewire 110 to be used to exert some control over the deployment of the SAM containment member 212. For example, by constructing the guidewire 110 to have two or more portions of differing lateral flexibility, the self-reconfiguration of the SAM containment member 212 can be at least partially controlled or influenced by the longitudinal positioning of the guidewire 110. In one such example, the guidewire 110 has a distal tip portion that is more laterally flexible than a stiffer portion that is proximal from the distal tip portion. Accordingly, when the stiffer portion of the guidewire 110 is engaged with the SAM containment member 212, the guidewire 110 restrains or partially restrains the SAM containment member 212 from moving to its fully deployed configuration. However, when the guidewire 110 is pulled back (proximally) so that the more laterally flexible portion of the guidewire 110 becomes engaged with the SAM containment member 212, then the bias of the SAM containment member 212 to self-reconfigure to its natural deployed configuration may overcome the lateral resistance from the guidewire 110. Therefore, by a clinician's selective positioning of the guidewire 110 relative to the SAM containment member 212, the deployment of the SAM containment member 212 can be at least partially controlled by the clinician.

As seen in FIG. 23, in some implementations as the SAM containment member 212 begins to reconfigure (or is partially reconfigured), the guidewire 110 may be thereby deflected into a position that advantageously contacts the back of the native anterior leaflet 20. As a result, the guidewire 110 may serve to draw or restrain the anterior leaflet 20 radially inward towards the prosthetic mitral valve 400, thus facilitating the capture of the anterior leaflet 20 during the deployment of the SAM containment member 212.

As seen in FIG. 24, when the SAM containment member 212 is configured in its deployed configuration, at least a portion of the SAM containment member 212 is disposed behind the anterior leaflet 20 of the native mitral valve 17. In some implementations, the anterior leaflet 20 is loosely contained in the space defined between the SAM containment member 212 and an exterior surface of the valve assembly 300. Accordingly, the potential for systolic anterior motion (SAM) of the anterior leaflet 20 is managed or controlled. That is, the anterior leaflet 20 is restrained from causing LVOT obstruction or the creation of high LVOT pressure gradients by the positioning of the SAM containment member 212 behind the anterior leaflet 20.

Figure 26:
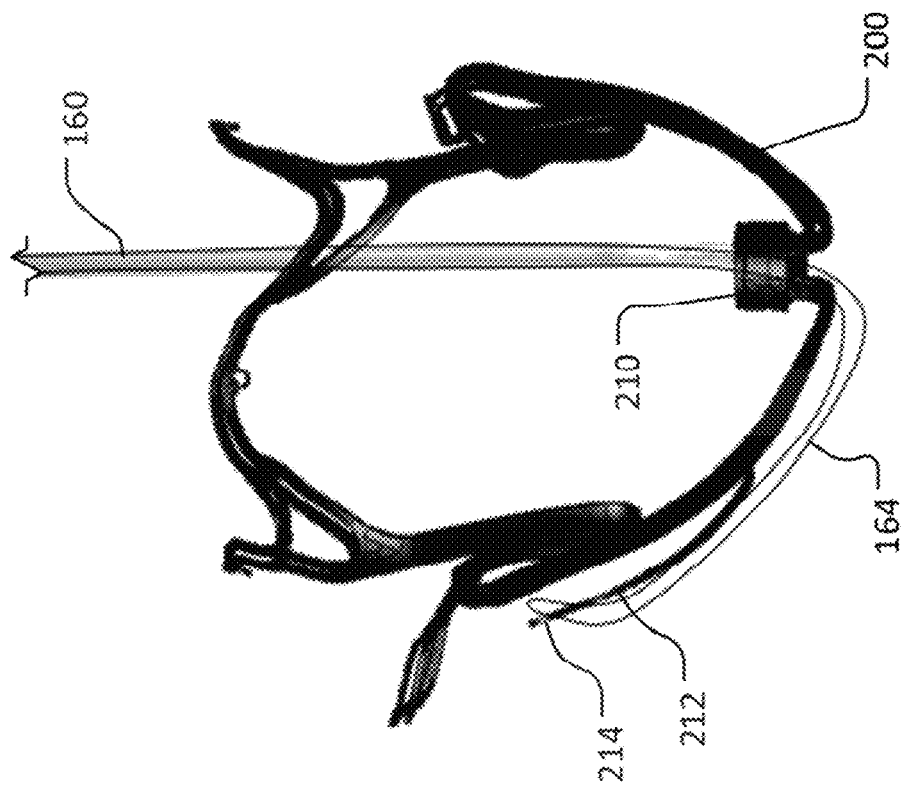
FIG. 26 shows the anchor assembly of FIG. 25 with the SAM containment member in a deployed configuration while still coupled with the deployment system, in accordance with some embodiments.
Figure 25:
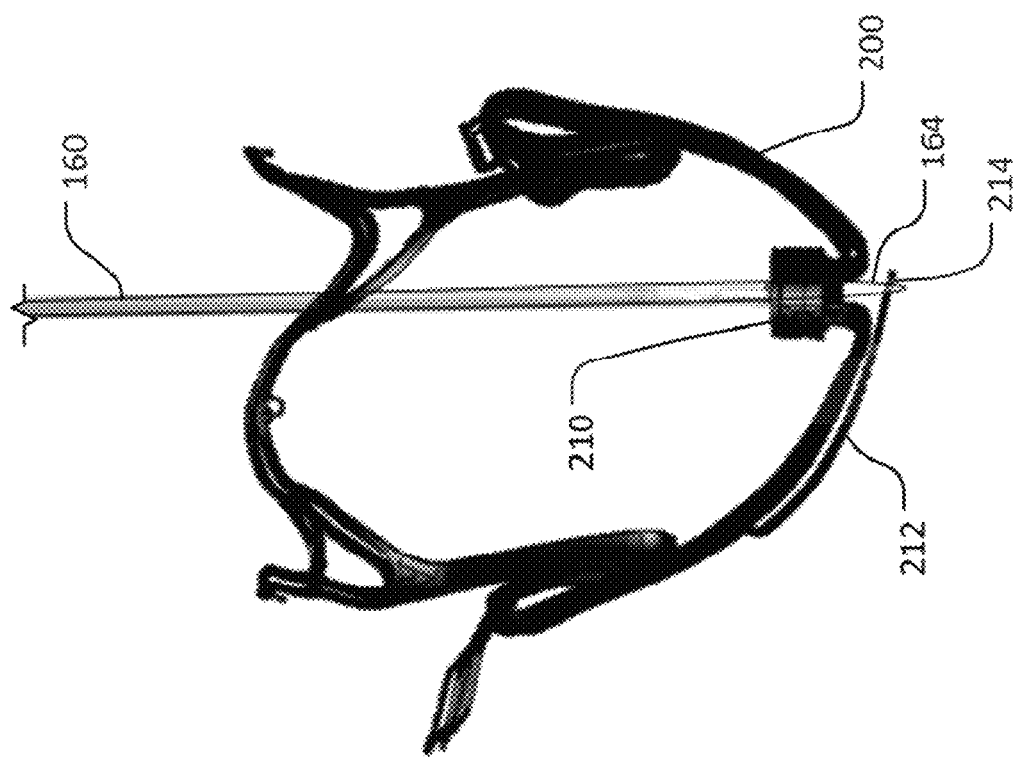
FIG. 25 shows a side view of the anchor assembly of FIG. 9 with a SAM containment member coupled with another example deployment system in a pre-deployed configuration, in accordance with some embodiments.

Referring to FIGS. 25 and 26, in some embodiments a control wire 164 of a delivery system 100 (e.g., refer to FIGS. 1-7 and 15-19) can be detachably coupled with the SAM containment member 212 so that a clinician can control the deployment of the SAM containment member 212. For example, in some embodiments the control wire 164 is coupled with an attachment element of the SAM containment member 212 (such as by threading the control wire 164 through the eyelet 214, in some embodiments).

In some embodiments, the control wire 164 is slidably disposed within a lumen of the distal pusher catheter 160. In particular embodiments, the control wire 164 is disposed exterior to the distal pusher catheter 160.

In some embodiments, the two ends of the control wire 164 can be positioned external to the patient such that the clinician operator can longitudinally adjust the position of the control wire 164, to thereby control the deployment positioning of the SAM containment member 212 (as depicted by comparing FIG. 25 with FIG. 26). For example, while both ends of the control wire 164 can be pulled and/or restrained proximally to position the SAM containment member 212 in its pre-deployed configuration (FIG. 25), one or both ends of the control wire 164 can also be moved or allowed to move distally to facilitate or encourage reconfiguration of the SAM containment member 212 to its deployed configuration (FIG. 26).

It should be understood that, using the control wire 164, the clinician can precisely control the deployment of the SAM containment member 212. For example, the clinician can thereby control the pace of the reconfiguration of the SAM containment member 212. Further, after the SAM containment member 212 has been deployed or partially deployed, the clinician can reverse-deploy the SAM containment member 212 (that is, pull the control wire 164 proximally so that the SAM containment member 212 returns partially or fully to the pre-deployed configuration). In this manner, the deployment process of the SAM containment member 212 is reversible and repeatable (as long as the control wire 164 remains coupled with the SAM containment member 212).

When the clinician operator deems that the SAM containment member 212 has been satisfactorily configured (e.g., such that at least a portion of the SAM containment member 212 is positioned behind the anterior leaflet), the clinician can then pull one end of the control wire 164 while releasing the other end of the control wire 164. By continuing to pull on the one end of the control wire 164, the control wire 164 can be eventually detached (e.g., unthreaded) from the SAM containment member 212.

Figure 34:
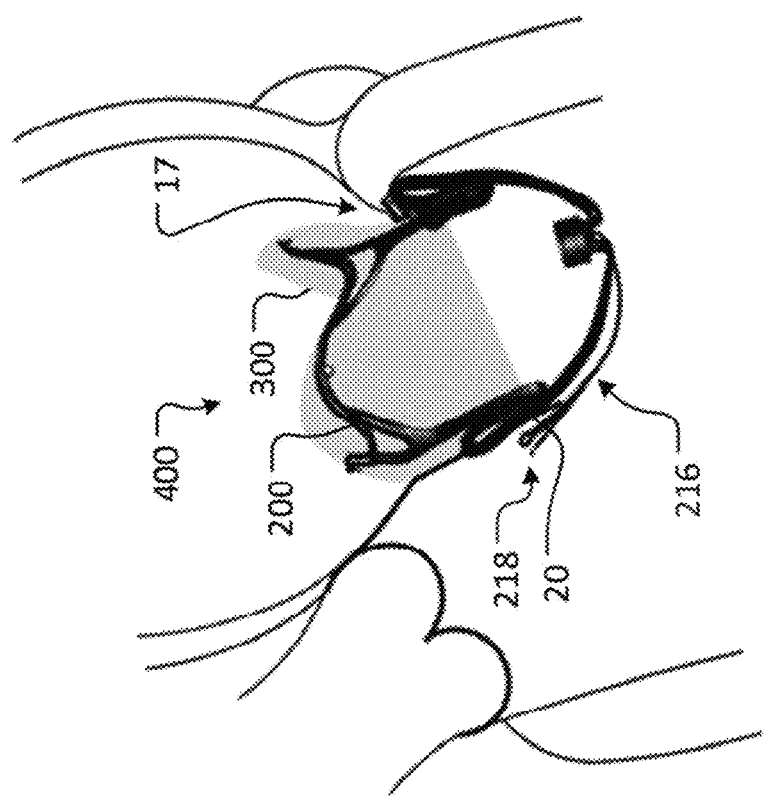
FIG. 34 shows another schematic side view of the native mitral valve coupled with the anchor assembly as in FIG. 29, with the SAM containment member in a fully deployed configuration, in accordance with some embodiments.

Referring to FIGS. 27-34, in some implementations a SAM containment member 216 (refer to FIG. 11) can be deployed while the anchor assembly 200 is engaged with the native mitral valve 17 (as described above). It should be understood that, in some implementations, the deployment process of the SAM containment member 216 can take place prior to the deployment of the valve assembly 300 (e.g., as depicted in FIG. 34). Alternatively, in some implementations the deployment process of the SAM containment member 216 can take place after the valve assembly 300 is mated with the anchor assembly 200. The embodiment depicted in FIGS. 27-34 is well suited for deployment prior to the artificial valve assembly 300 implementation, as its design, which emanates from the hub 210 has little impact on the normal function of the anterior leaflet, and allows the anterior leaflet to continue to function essentially normally prior to the implantation of the valve assembly 300.

Figure 28:
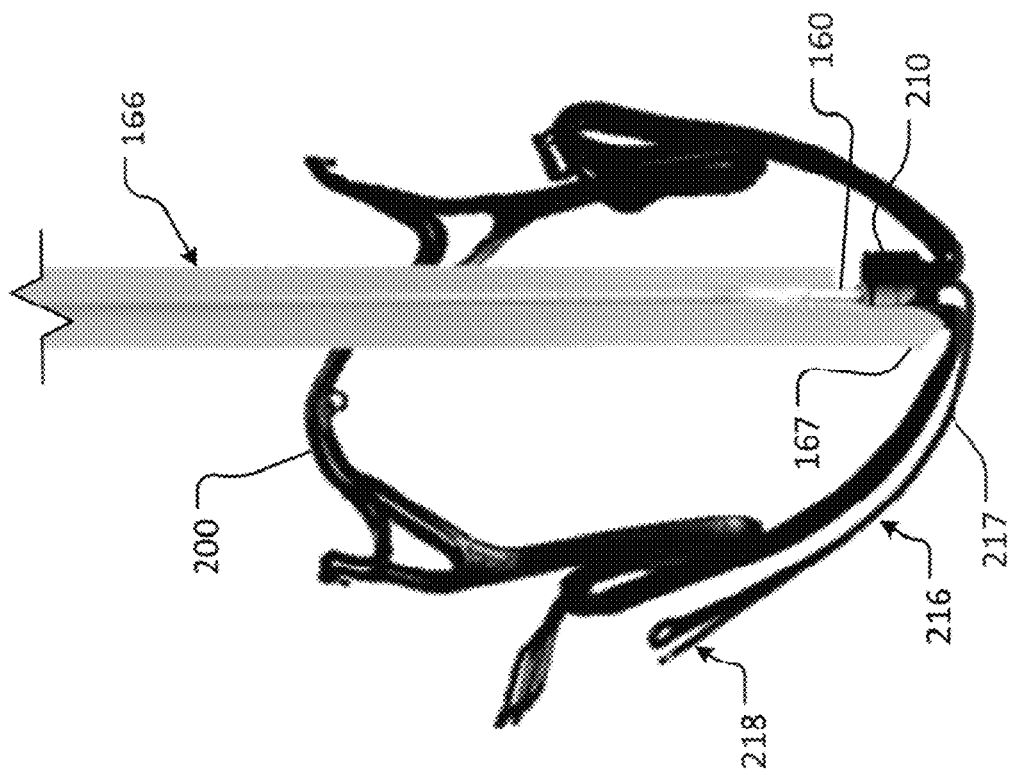
FIG. 28 shows the anchor assembly of FIG. 27 with the SAM containment member in a deployed configuration, in accordance with some embodiments.
Figure 27:
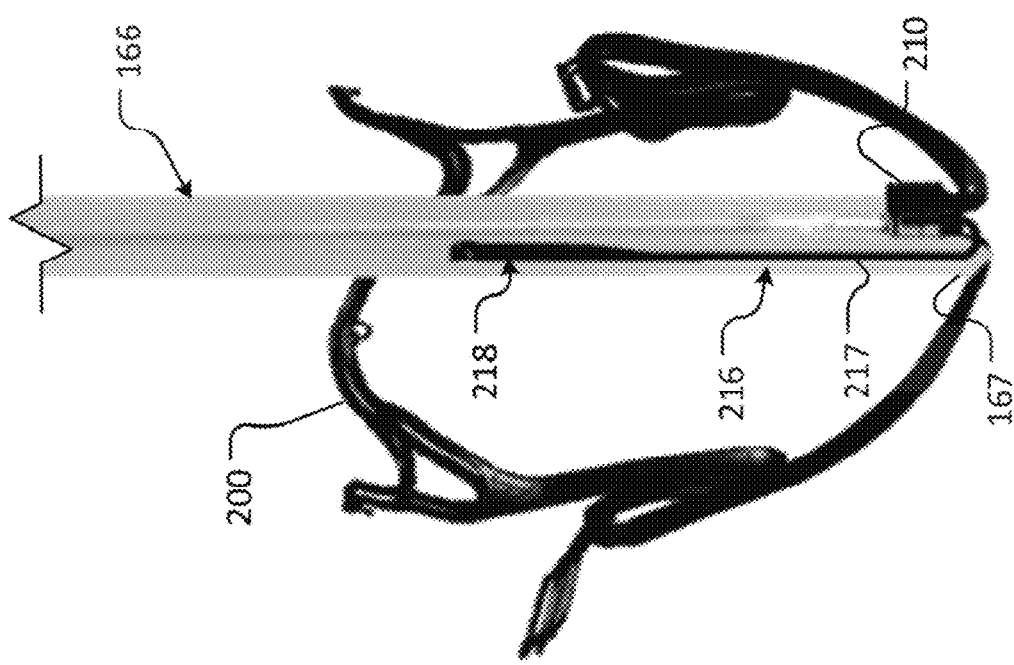
FIG. 27 shows a side view of the anchor assembly of FIG. 11 with a SAM containment member coupled with another example deployment system in a pre-deployed configuration, in accordance with some embodiments.
Figure 30:
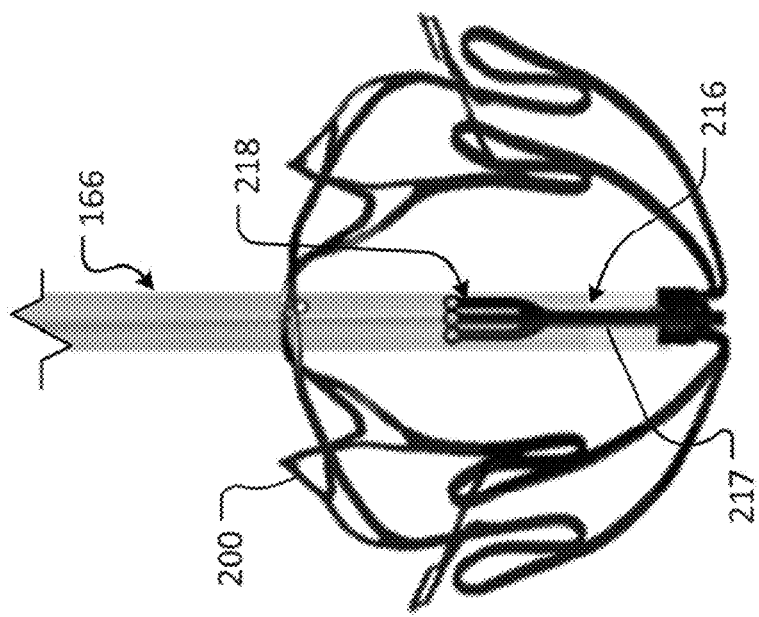
FIG. 30 shows an anterior side view of the anchor assembly of FIG. 11 and the deployment system of FIG. 27 with the SAM containment member in a pre-deployed configuration as in FIG. 29, in accordance with some embodiments.
Figure 29:
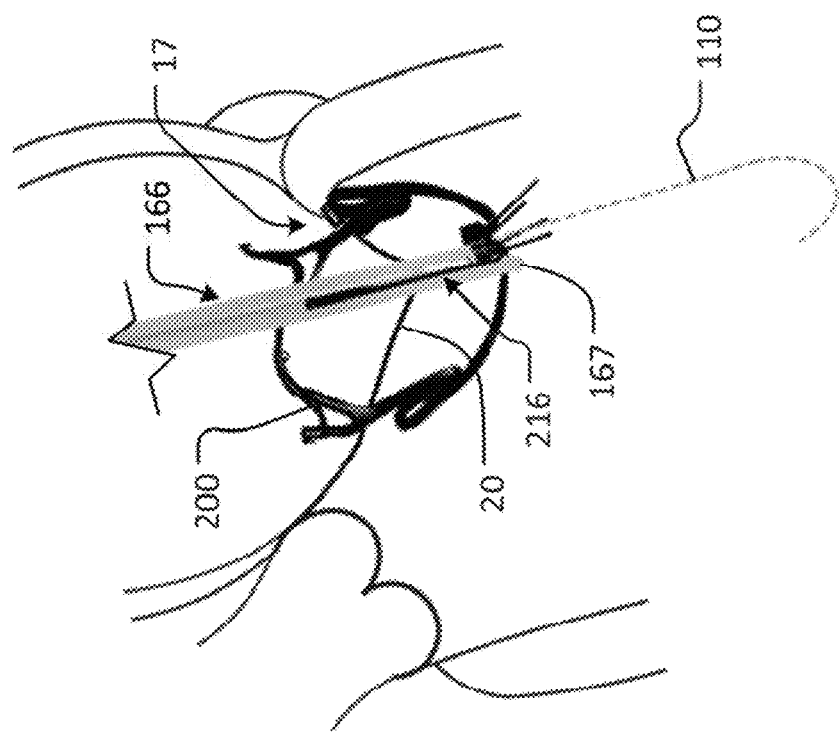
FIG. 29 shows a schematic side view of a native mitral valve coupled with the anchor assembly of FIG. 11, and the deployment system of FIG. 27, with the SAM containment member in a pre-deployed configuration, in accordance with some embodiments.
Figure 32:
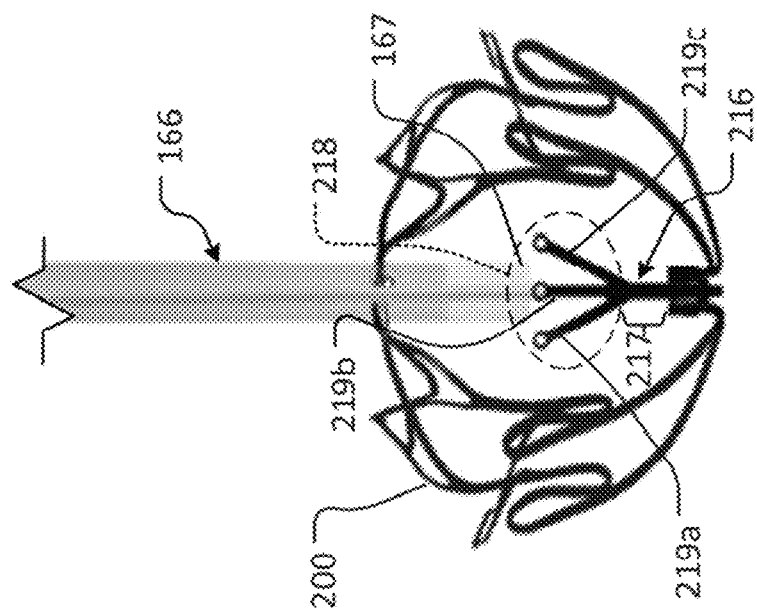
FIG. 32 shows a front view of the anchor assembly of FIG. 11 and the deployment system of FIG. 27 with the SAM containment member in a partially-deployed configuration as in FIG. 31, in accordance with some embodiments.
Figure 31:
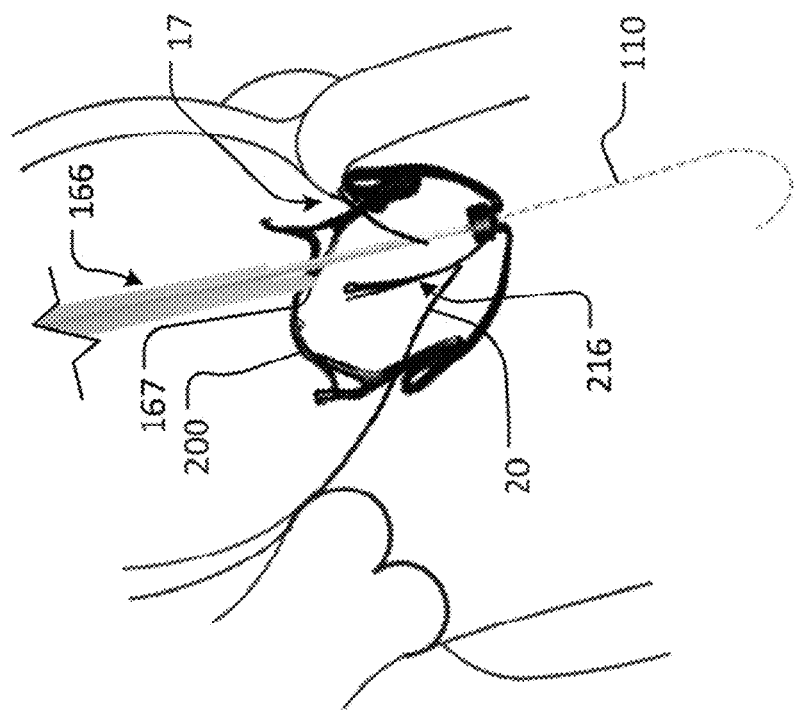
FIG. 31 shows another schematic side view of the native mitral valve coupled with the anchor assembly as in FIG. 29, and the deployment system of FIG. 27, with the SAM containment member in a partially-deployed configuration, in accordance with some embodiments.
Figure 33:
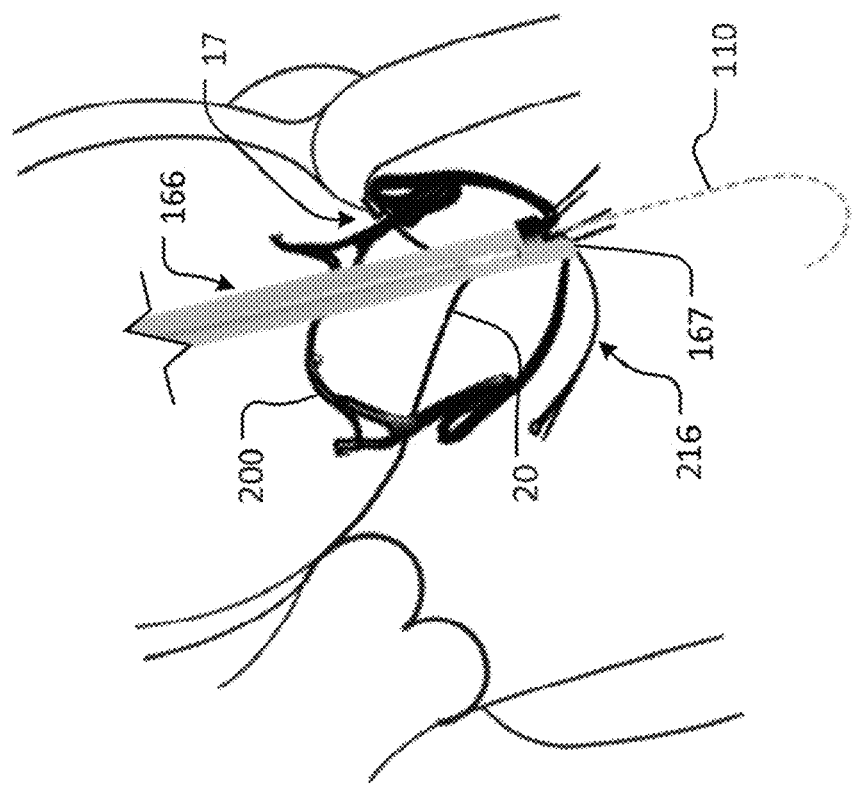
FIG. 33 shows another schematic side view of the native mitral valve coupled with the anchor assembly as in FIG. 29, and the deployment system of FIG. 27, with the SAM containment member in a partially-deployed configuration, in accordance with some embodiments.

FIGS. 27, 29, and 30 show the position of the SAM containment member 216 in its pre-deployed configuration within a sheath 166. FIGS. 31 and 32 show the position of the SAM containment member 216 in its partially-deployed configuration after emergence from the sheath 166, but prior to receiving a deformation force from the sheath 166. FIGS. 28, 33, and 34 show the position of the SAM containment member 216 in its deployed configuration after being deformed thereto by a deformation force applied via the sheath 166.

The SAM containment member 216 comprises an elongate element arm portion 217 (attached to the hub 210 of the anchor assembly 200) and an end portion 218 that extends from the arm portion 217. In some embodiments, the end portion 218 extending from the elongate member arm portion 217 defines a width that is greater than the width of the arm portion 217. As described further below, the end portion 218 is configured to be disposed behind an anterior leaflet when the anchor assembly 200 is engaged with a native mitral valve.

As shown in FIGS. 27, 29, and 30, in some embodiments the SAM containment member 216 can be arranged in a pre-deployed configuration where it is slidably disposed within a lumen of a sheath 166 in a low-profile configuration suitable for transcatheter delivery. In some embodiments, the distal pusher catheter 160 is also slidably disposed within the sheath 166. With the SAM containment member 216 constrained in this pre-deployed configuration, the anchor assembly 200 can be expanded and engaged within the native mitral valve 17 as depicted in FIG. 29.

In some implementations, after the engagement of the anchor assembly 200 with the native mitral valve 17, the deployment process of the SAM containment member 216 can be performed. First, as shown in FIGS. 31 and 32, the sheath 166 can be pulled proximally by a clinician operator to allow the SAM containment member 216 to emerge from containment within the sheath 166. When the sheath 166 is pulled back, in some embodiments the natural bias of the SAM containment member 216 causes the SAM containment member 216 to deflect radially away from its previous position within the sheath 166. Additionally, due to the removal of the diametrically constraining sheath 166, in some embodiments the end portion 218 expands to the natural unconstrained configuration of the end portion 218. For example, in the depicted embodiment the three elongate members 219a-c fan out laterally to define a width that is greater than the width of the arm portion 217.

In some embodiments, the next step of the deployment process of the SAM containment member 216 comprises further radial deflection of the SAM containment member 216, so that the end portion 218 becomes disposed behind the anterior leaflet 20. This step is depicted in FIGS. 28 and 33, and can be performed under fluoroscopy (as can some or all of the other deployment steps described herein).

In some implementations, this step of further radial deflection of the SAM containment member 216 is performed at least in part by the application of a force from the sheath 166 to the arm portion 217. That is, in some embodiments the sheath 166 includes a distal end 167 that is configured to interface with the arm portion 217, and to apply a force thereto that results in radial deflection of the SAM containment member 216. For example, in some embodiments when the clinician operator pushes the sheath 166 distally, the distal end 167 presses on the arm portion 217 to cause a radial deflection of the SAM containment member 216.

In some embodiments, the deflection of the SAM containment member 216 so that the end portion 218 becomes disposed behind the anterior leaflet 20 occurs by plastic deformation of the SAM containment member 216 as a result of the forces applied thereto by the sheath 166. In various embodiments, the deflection of the SAM containment member 216 so that the end portion 218 becomes disposed behind the anterior leaflet 20 occurs by the natural bias of the SAM containment member 216 after the SAM containment member 216 is allowed to emerge from the sheath 166, and without additional forces applied by the sheath 166. In particular embodiments, the deflection of the SAM containment member 216 so that the end portion 218 becomes disposed behind the anterior leaflet 20 is achieved by a combination of the natural bias of the SAM containment member 216 after the SAM containment member 216 is allowed to emerge from the sheath 166, and further urging thereof as a result of the forces applied to the arm portion 217 by the sheath 166.

In some implementations, after the deployment of the SAM containment member 216 so that the end portion 218 becomes disposed behind the anterior leaflet 20, the valve assembly 300 is then deployed to mate with the anchor assembly 200 as depicted in FIG. 34. Alternatively, in some implementations the SAM containment member 216 is deployed so that the end portion 218 becomes disposed behind the anterior leaflet 20 after the valve assembly 300 has been deployed to mate with the anchor assembly 200. In some implementations, the anterior leaflet 20 is loosely contained in the space defined between the SAM containment member 216 and an exterior surface of the valve assembly 300. In some implementations, the anterior leaflet 20 is snuggly contained or lightly compressed in the space defined between the SAM containment member 216 and an exterior surface of the valve assembly 300.

Figure 35:
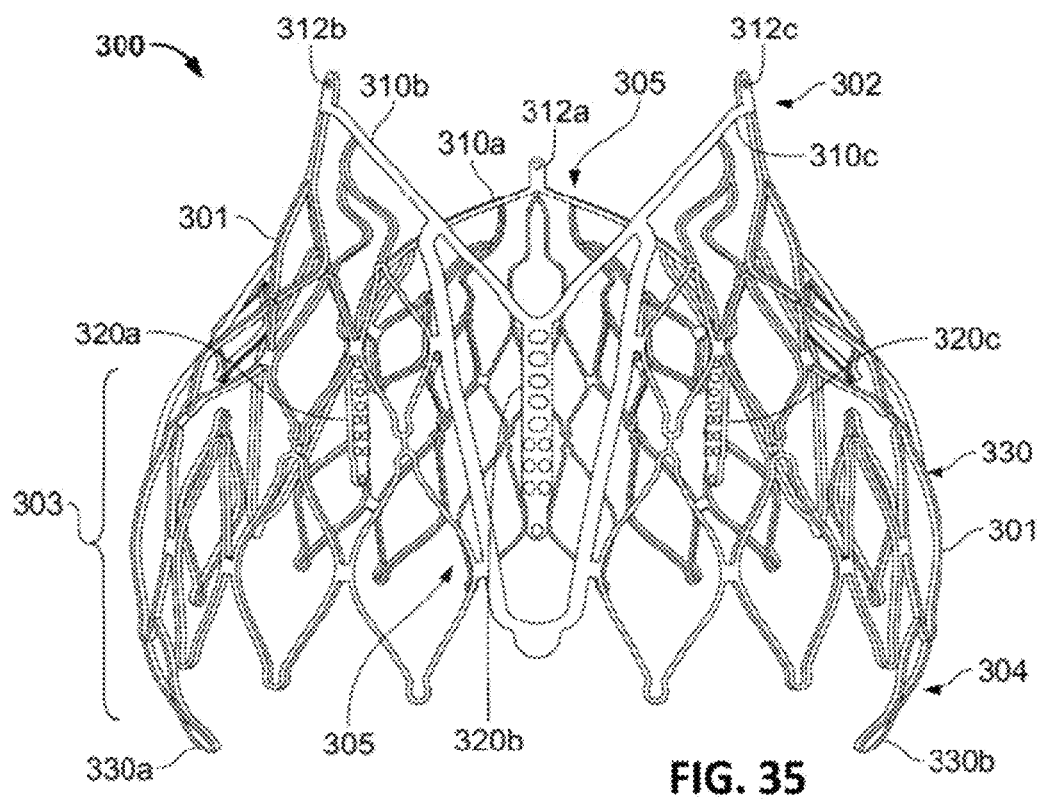
FIG. 35 shows an anterior side view of a valve frame of a valve assembly of FIGS. 16-19, in accordance with some embodiments.
Figure 36:
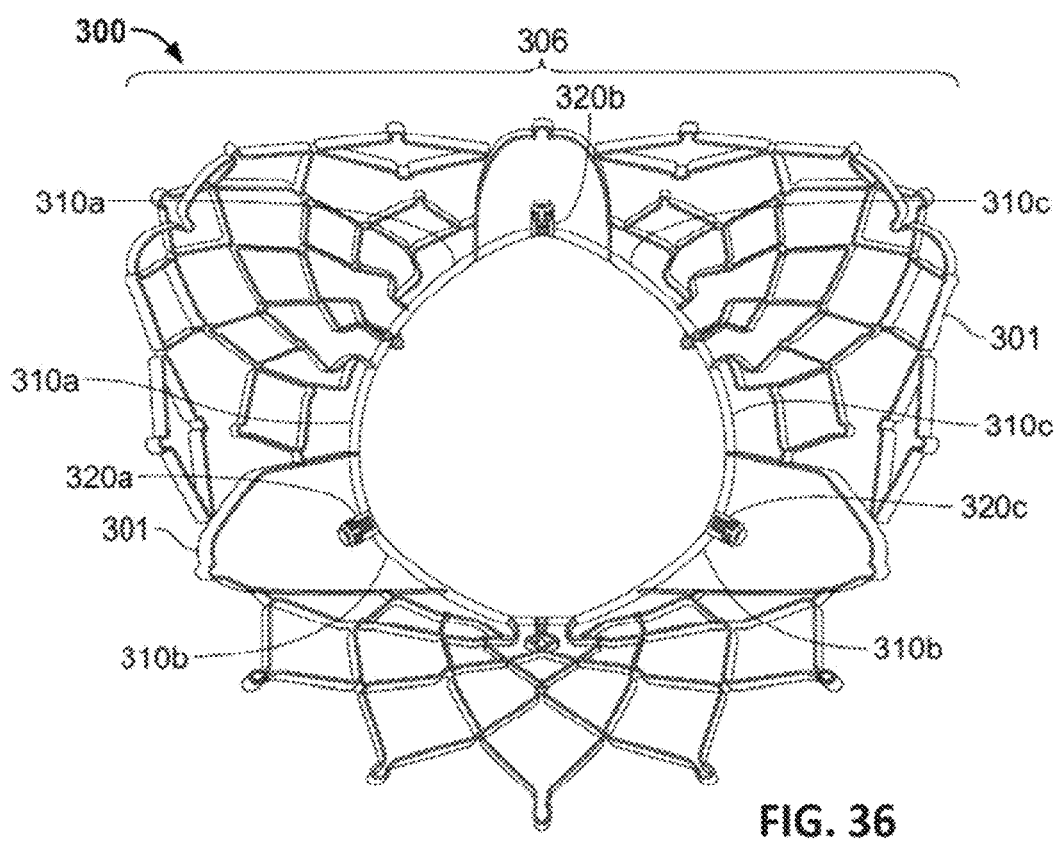
FIG. 36 shows a bottom view of the valve frame of FIG. 35.

Referring to FIGS. 35 and 36, an example valve assembly 300 is shown without any covering or valve/occluder leaflets. Hence, a valve assembly frame 301 of the valve assembly 300 is shown. FIG. 35 shows an anterior side view of the valve assembly frame 301, and FIG. 36 shows a bottom view of the valve assembly frame 301. The valve assembly 300 can be constructed using any of the various materials and manufacturing techniques described above in reference to the anchor frame 200 (e.g., refer to FIG. 9). It should be understood that the depicted valve assembly 300 is merely one non-limiting example of the valve assemblies provided within the scope of this disclosure.

The valve assembly 300 includes a proximal end portion 302 and a distal end portion 304. The valve assembly includes a flared external skirt portion 303 and defines an interior orifice portion 305. When the valve assembly 300 is implanted in a native mitral valve, the proximal end portion 302 is located supra-annular (in the left atrium) and the distal end portion 304 is located sub-annular (in the left ventricle). The proximal end portion 302 defines the generally circular entrance orifice of the valve assembly 300, as described further below.

In the depicted embodiment, the valve assembly 300 generally flares outward along a distal direction. Said differently, the distal end portion 304 is flared outward in comparison to the proximal end portion 302. Accordingly, the proximal end portion 302 defines a smaller outer profile in comparison to the distal end portion 304. However, some regions of the distal end portion 304 bow inwardly. In particular, for example, a posteromedial commissural corner 330a and anterolateral commissural corner 330b of the valve assembly 300 may bow inwardly. It should be understood that the outward flare of the distal end portion 304 in comparison to the proximal end portion 302 is merely one example configuration for a profile of the valve assembly 300. In some embodiments, for example, a shoulder (a portion of the valve assembly 300 having the largest outer periphery) is located proximal of the middle of the valve assembly 300.

The valve assembly 300 also includes an anterior side 306 between the posteromedial commissural corner 330a and anterolateral commissural corner 330b. When the valve assembly 300 is implanted in a native mitral valve, the anterior side 306 faces the anterior leaflet of the native mitral valve. The anterior side 306 of the distal end portion 304 defines a generally flat surface, whereas the other sides of the distal end portion 304 are rounded. Hence, the periphery of the distal end portion 304 is generally D-shaped. The D-shaped periphery of the distal end portion 304 provides the valve assembly 300 with an advantageous outer profile for interfacing and sealing with the native mitral valve. As described further below, sealing is attained by coaptation between the D-shaped periphery of the distal end portion 304 and the leaflets of the native mitral valve, and, in some embodiments, between the D-shaped periphery in the region of the skirt 303 with the native valve annulus.

In the depicted embodiment, the proximal end portion 302 of the valve assembly 300 includes three atrial leaflet arches 310a, 310b, and 310c that together define an undulating ring at the proximal end portion 302. Each of the leaflet arches 310a, 310b, and 310c includes an apex having an attachment hole 312a, 312b, and 312c respectively. In some embodiments, the attachment holes 312a, 312b, and 312c are used for coupling the proximal end of the valve assembly 300 to a delivery catheter (e.g., valve delivery catheter 180 of FIGS. 16-18).

The valve assembly 300 also includes three commissural posts 320a, 320b, and 320c that each extend distally from the intersections of the three leaflet arches 310a, 310b, and 310c. The commissural posts 320a, 320b, and 320c are disposed at about 120° apart from each other. The commissural posts 320a, 320b, and 320c each have a series of holes that can be used for attachment of leaflets, such as by suturing. The three leaflet arches 310a, 310b, and 310c and the three commissural posts 320a, 320b, and 320c are areas on the valve assembly 300 to which three prosthetic valve leaflets become attached to comprise a tri-leaflet occluder (e.g., refer to FIGS. 38-41).

As best seen in FIG. 36, the three leaflet arches 310a, 310b, and 310c and the commissural posts 320a, 320b, and 320c define a generally cylindrical frame for the tri-leaflet occluder construct. As such, the valve assembly 300 provides a proven and advantageous frame configuration for the tri-leaflet occluder. The tri-leaflet occluder provides open flow during diastole and occlusion of flow during systole.

Referring to FIG. 37, an exploded depiction of an example prosthetic mitral valve 400 includes an anchor assembly 200 and a valve assembly 300. This figure provides a posterior side view of the anchor assembly 200 and the valve assembly 300.

The valve assembly 300 includes a covering 340. The covering 340 can be made of any of the materials and constructed using any of the techniques described above in reference to covering 270. Additionally, in some embodiments the covering 340 can comprise natural tissues such as, but not limited to, bovine, porcine, ovine, or equine pericardium. In some such embodiments, the tissues are chemically cross-linked using glutaraldehyde, formaldehyde, or triglycidyl amine solution, or other suitable crosslinking agents.

When the valve assembly 300 and the anchor assembly 200 are coupled together, the valve assembly 300 is geometrically interlocked within the interior of the anchor assembly 200 (e.g., in some embodiments by virtue of the tapered shape of the valve assembly 300 within the supra-annular ring and interior space of the anchor assembly 200). In particular, in some embodiments the valve assembly 300 is contained within the interior space between the supra-annular ring 250 and the sub-annular support arms 230a, 230b, 230c, and 230d. As described above, the interlocked arrangement between the valve assembly 300 and the anchor assembly 200 is accomplished by positioning a valve assembly 300 in a low-profile configuration within the interior of the anchor assembly 200 and then allowing expansion of the valve assembly 300 within the interior of the anchor assembly 200 (e.g., refer to FIGS. 18 and 19).

Figure 38:
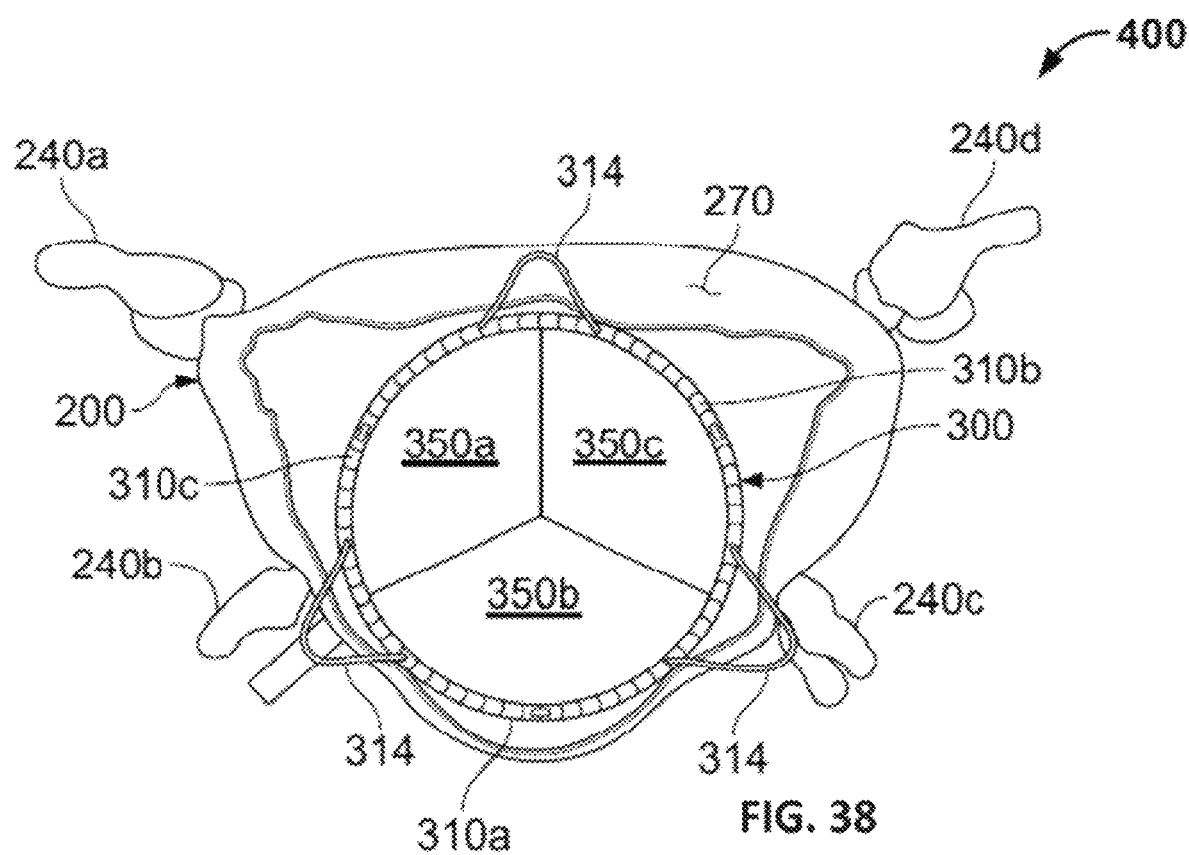
FIG. 38 is a top view of an example prosthetic mitral valve system that includes a valve assembly engaged with an anchor assembly, in accordance with some embodiments.
Figure 39:
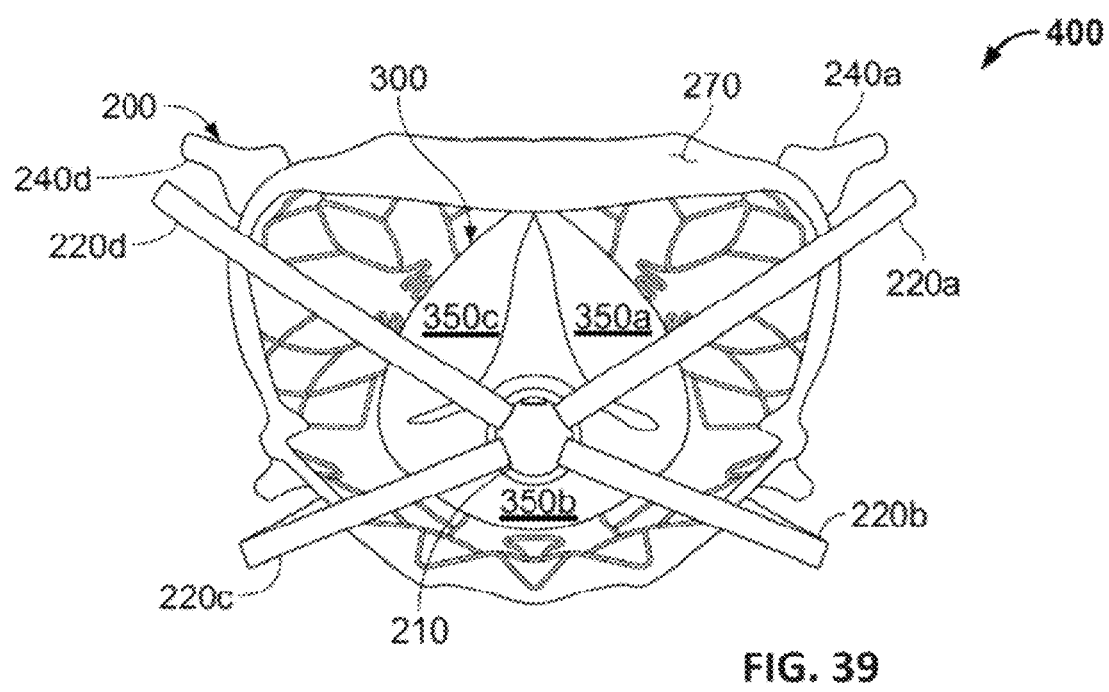
FIG. 39 is a bottom view of the example prosthetic mitral valve system of FIG. 38.

Referring to FIGS. 38 and 39, a deployed configuration of the example prosthetic mitral valve 400 includes the valve assembly 300 engaged within the anchor assembly 200. FIG. 38 shows a top (atrial) view of the prosthetic mitral valve 400, and FIG. 39 shows a bottom (ventricle) view of the prosthetic mitral valve 400.

In some embodiments, such as the depicted embodiment, valve assembly 300 includes three leaflets 350a, 350b, and 350c that perform the occluding function of the prosthetic mitral valve 400. The cusps of the three leaflets 350a, 350b, and 350c are fixed to the three atrial leaflet arches 310a, 310b, and 310c, and to the three commissural posts 320a, 320b, and 320c (refer to FIGS. 35 and 36). The free edges of the three leaflets 350a, 350b, and 350c can seal by coaptation with each other during systole and open during diastole.

The three leaflets 350a, 350b, and 350c can be comprised of natural or synthetic materials. For example, the three leaflets 350a, 350b, and 350c can be comprised of any of the materials described above in reference to the covering 340, including the natural tissues such as, but not limited to, bovine, porcine, ovine, or equine pericardium. In some such embodiments, the tissues are chemically cross-linked using glutaraldehyde, formaldehyde, or triglycidyl amine solution, or other suitable crosslinking agents. In some embodiments, the leaflets 350a, 350b, and 350c have a thickness in a range of about 0.005" to about 0.020" (about 0.13 mm to about 0.51 mm), or about 0.008" to about 0.012" (about 0.20 mm to about 0.31 mm). In some embodiments, the leaflets 350a, 350b, and 350c have a thickness that is less than about 0.005" (about 0.13 mm) or greater than about 0.020" (about 0.51 mm).

In some embodiments, the occluding function of the prosthetic mitral valve 400 can be performed using configurations other than a tri-leaflet occluder. For example, bi-leaflet, quad-leaflet, or mechanical valve constructs can be used in some embodiments.

In some embodiments, a SAM containment member is included as part of the anchor assembly 200 (e.g., refer to FIGS. 10 and 11). In the depicted embodiment, no SAM containment member is included.

Figure 40:
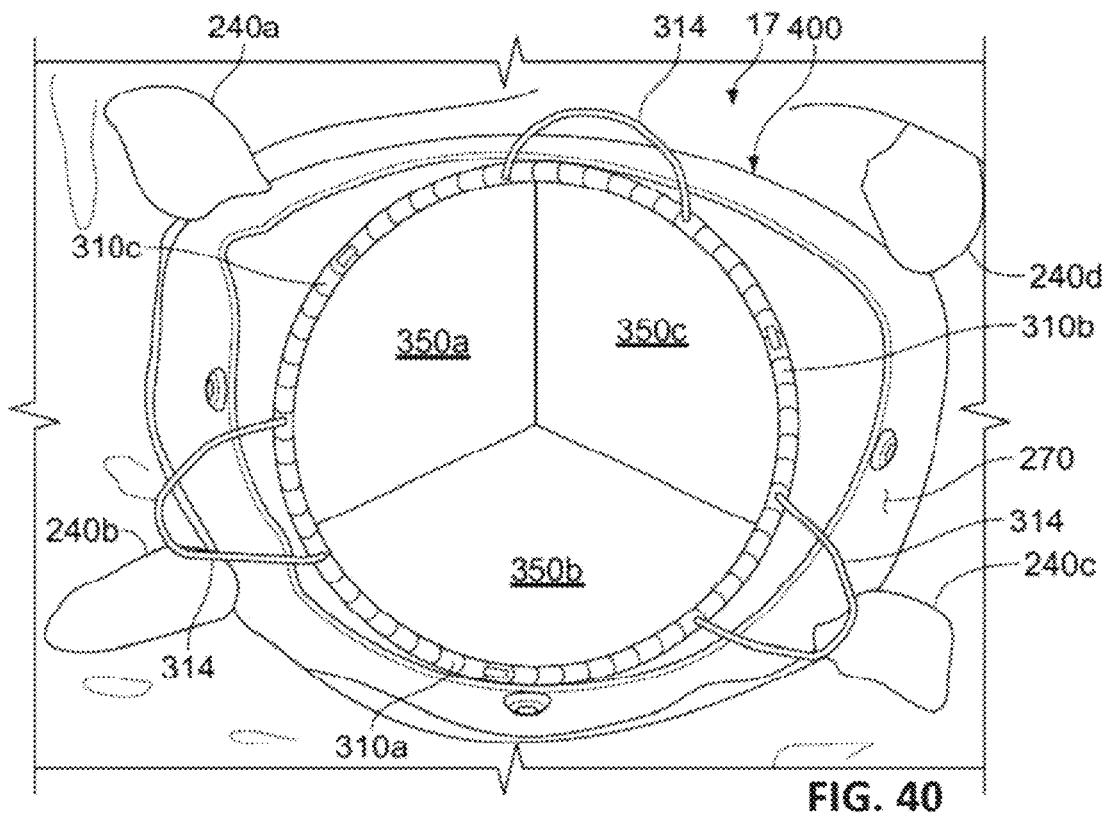
FIG. 40 shows a top view of the prosthetic mitral valve system of FIG. 38 implanted within a native mitral valve. The occluder portion of prosthetic mitral valve system is shown in a closed state.
Figure 41:
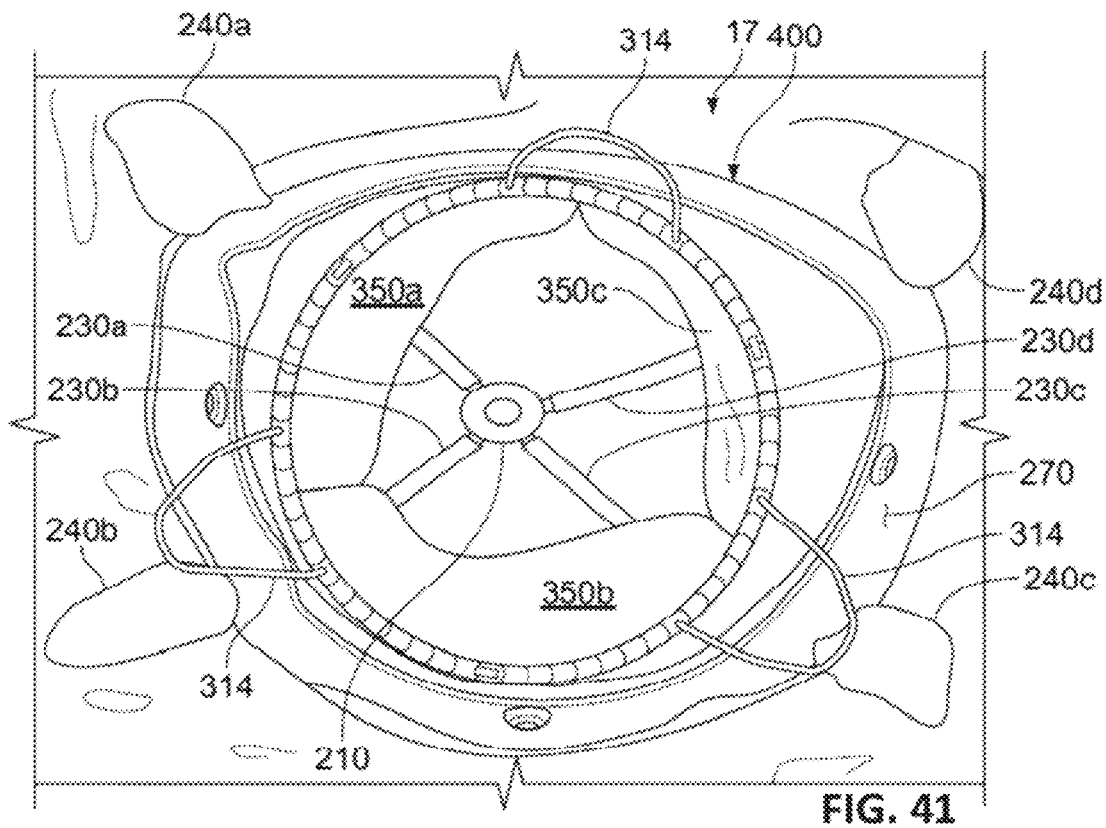
FIG. 41 shows a top view of the prosthetic mitral valve system of FIG. 38 implanted within a native mitral valve. The occluder portion of the prosthetic mitral valve system is shown in an open state.

Referring to FIGS. 40 and 41, the prosthetic mitral valve 400 is shown implanted within a native mitral valve 17. In FIG. 40, the prosthetic mitral valve 400 is shown in a closed state (occluded). In FIG. 41, the prosthetic mitral valve 400 is shown in an open state. These illustrations are from the perspective of the left atrium looking towards the mitral valve 17. For instance, in FIG. 41 the hub 210 and the sub-annular support arms 230a, 230b, 230c, and 230d of the anchor assembly 200 are visible through the open leaflets 350a, 350b, and 350c of the prosthetic mitral valve 400, whereas in FIG. 40 the hub 210 and the sub-annular support arms 230a, 230b, 230c, and 230d are not visible because the closed leaflets 350a, 350b, and 350c block the hub 210 from view.

A number of embodiments of the invention have been described. Nevertheless, it will be understood that various modifications may be made without departing from the scope of the invention. Accordingly, other embodiments are within the scope of the following claims.

What is claimed is:

1. A prosthetic mitral valve system comprising:
   a valve assembly comprising an expandable valve frame and leaflets attached to the expandable valve frame; and
   an anchor assembly comprising an expandable anchor frame, the anchor assembly configured to couple with the expandable valve frame, the expandable anchor frame comprising:
   a containment member that is configured to be at least partially disposed behind an anterior leaflet of a native mitral valve when the expandable anchor frame is engaged with the native mitral valve;
   a hub member located at an end of the expandable anchor frame; and
   a plurality of elongate members attached to and extending from the hub member, each elongate member including a sub-annular projection configured to engage tissue proximate to an annulus of the native mitral valve when the expandable anchor frame is in an expanded configuration, wherein the containment member is attached to and extends between two adjacent elongate members.

2. The prosthetic mitral valve system of claim 1, wherein the expandable valve frame of the valve assembly is configured to be in a collapsed condition positioned inwardly of the expandable anchor frame of the anchor assembly when the expandable anchor frame is engaged with the native mitral valve, and the expandable valve frame of the valve assembly is configured to subsequently expand when positioned inwardly of the expandable anchor frame of the anchor assembly so as to couple the anchor assembly and the valve assembly.

3. The prosthetic mitral valve system of claim 2, wherein a space is defined between an outwardly facing periphery of the valve assembly and the containment member that is configured to loosely contain the anterior leaflet when the prosthetic mitral valve system is engaged with the native mitral valve.

4. The prosthetic mitral valve system of claim 1, wherein the containment member further comprises an attachment element.

5. The prosthetic mitral valve system of claim 4, further comprising a delivery system for deploying the anchor assembly, wherein the delivery system comprises a catheter with a threaded distal end portion that is configured to threadedly engage with a complimentarily threaded eyelet defined by the attachment element.

6. The prosthetic mitral valve system of claim 4, further comprising a delivery system for deploying the anchor assembly, wherein the delivery system comprises a control wire configured to engage with the attachment element.

7. The prosthetic mitral valve system of claim 1, wherein the expandable anchor frame includes a single containment member.

8. A prosthetic mitral valve system comprising:
an expandable frame with leaflets coupled thereto, wherein the expandable frame comprises:
a containment member that is configured to be at least partially disposed behind an anterior leaflet of a native mitral valve when the expandable frame is engaged with the native mitral valve, the containment member comprising an attachment element;
a hub member located at an end of the expandable frame; and
a plurality of elongate members attached to and extending from the hub member, each elongate member including a sub-annular projection configured to engage tissue proximate to an annulus of the native mitral valve when the expandable frame is engaged with the native mitral valve,
wherein the containment member is attached to and extends between two adjacent elongate members; and
a delivery system for transcatheter deployment of the expandable frame within the native mitral valve, wherein the delivery system is releasably coupleable with the attachment element.

9. The prosthetic mitral valve system of claim 8, wherein the attachment element comprises an eyelet.

10. The prosthetic mitral valve system of claim 9, wherein the eyelet includes eyelet threads, and wherein the delivery system comprises a member with threads that are complementary with the eyelet threads.

11. The prosthetic mitral valve system of claim 9, wherein the delivery system comprises a control wire that engages with the eyelet.

12. The prosthetic mitral valve system of claim 8, wherein the expandable frame includes a single containment member, and the expandable frame is an expandable anchor frame;
and wherein the leaflets are mounted to an expandable valve frame of a valve assembly, the expandable valve frame being configured to be in a collapsed condition positioned inwardly of the expandable anchor frame when the expandable anchor frame is engaged with the native mitral valve, and the expandable valve frame of the valve assembly is configured to subsequently expand when positioned inwardly of the expandable anchor frame so as to couple the expandable anchor frame and the leaflets of the valve assembly.

13. An anchor assembly of a prosthetic mitral valve system, the anchor assembly comprising:
an expandable anchor frame that is adjustable between a radially compressed delivery condition and a radially expanded deployed condition in which the expandable anchor frame is configured to engage with a native mitral valve, the anchor assembly configured to mate with a valve assembly of a prosthetic mitral valve system, wherein the expandable anchor frame comprises:
a containment member that is configured to be at least partially disposed behind an anterior leaflet of the native mitral valve when the expandable anchor frame is engaged with the native mitral valve;
a hub member located at an end of the expandable anchor frame; and
a plurality of elongate members attached to and extending from the hub member, each elongate member including a sub-annular projection configured to engage tissue proximate to an annulus of the native mitral valve when the expandable anchor frame is in an expanded configuration, wherein the containment member is attached to and extends between two adjacent elongate members.

14. The anchor assembly of claim 13, wherein the containment member further comprises an attachment element configured to releasably engage with a portion of a delivery system.

15. The anchor assembly of claim 14, wherein the attachment element comprises an eyelet.

16. The anchor assembly of claim 13, wherein the expandable anchor frame includes a single containment member.

* * * * *